United States Patent [19]

Doran et al.

[11] Patent Number: 5,635,617
[45] Date of Patent: Jun. 3, 1997

[54] METHODS AND COMPOSITIONS COMPRISING THE AGFA GENE FOR DETECTION OF SALMONELLA

[75] Inventors: James L. Doran, Brentwood Bay; William W. Kay, Victoria; S. Karen Collinson, Brentwood Bay; Sharon C. Clouthier, Naniamo, all of Canada

[73] Assignee: University of Victoria Innovation & Development Corp., Victoria, Canada

[21] Appl. No.: 233,788

[22] Filed: Apr. 26, 1994

Related U.S. Application Data

[63] Continuation-in-part of Ser. No. 54,452, Apr. 26, 1993, abandoned.
[51] Int. Cl.$^6$ .............................. C07H 21/02; C07H 21/04
[52] U.S. Cl. .................................. 536/23.7; 536/23.1
[58] Field of Search .............................. 536/23.7, 23.2, 536/24.33, 23.1

[56] References Cited

U.S. PATENT DOCUMENTS

| | | | |
|---|---|---|---|
| 4,443,549 | 4/1984 | Sadowski | 436/548 |
| 4,689,295 | 8/1987 | Taber et al. | 435/6 |
| 5,043,264 | 8/1991 | Jikuya et al. | 435/6 |
| 5,147,778 | 9/1992 | Nietupski et al. | 435/6 |

FOREIGN PATENT DOCUMENTS

| | | | |
|---|---|---|---|
| 114 668 A2 | 8/1984 | European Pat. Off. | C12Q 1/68 |
| 355 989 A2 | 2/1990 | European Pat. Off. | C12Q 1/68 |
| 383 509 A2 | 8/1990 | European Pat. Off. | C12Q 1/68 |
| 2234587 | 2/1991 | United Kingdom | G01N 33/569 |
| WO86/00993 | 2/1986 | WIPO | G01N 33/569 |
| WO86/01805 | 3/1986 | WIPO | C07K 15/00 |
| WO86/04352 | 7/1986 | WIPO | C12N 11/14 |
| WO88/03957 | 6/1988 | WIPO | C12Q 1/68 |
| WO89/01162 | 2/1989 | WIPO | G01N 33/569 |
| WO89/05359 | 6/1989 | WIPO | C12Q 1/68 |
| WO90/00624 | 1/1990 | WIPO | C12Q 1/68 |
| WO91/19003 | 12/1991 | WIPO | C12Q 1/04 |
| WO92/01056 | 1/1992 | WIPO | C12N 15/31 |
| WO92/06197 | 4/1992 | WIPO | C12N 15/31 |
| WO92/06198 | 4/1992 | WIPO | C12N 15/31 |
| WO93/04202 | 3/1993 | WIPO | C12Q 1/68 |
| WO93/20231 | 10/1993 | WIPO | C12Q 1/68 |

OTHER PUBLICATIONS

Doran et al J. Clin. Microbiol 31: 2263–2273 (1993).

Collinson et al., "Aggregative Fimbriae of *Salmonella enteritidis*," in Abstracts of the 22nd Annual Western Branch Meeting of the Canadian Society for Microbiology, Abstract #I–10, Nov. 14–16, Vancouver B.C., 1991.

Clouthier et al., "Characterization of three fimbrial genes, sefA, B, and C of *Salmonella enteritidis*," in Abstracts of the 22nd Annual Western Branch Meeting of the Canadian Society for Microbiology, Abstract #I–9, Nov. 14–16, Vancouver B.C., 1991.

Müller et al., "Type 1 Fimbriae of *Salmonella enteritidis*, "*Journal of Bacteriology* 173(15):4765–4772, 1991.

Collinson et al., "Purification and Characterization of Thin, Aggregative Fimbriae from *Salmonella enteritidis*," *Journal of Bacteriology* 173(15): 4773–4781, 1991.

Collinson et al., "Thin, Aggregative Fimbriae Mediate Binding of *Salmonella enteritidis* to Fibronectin," *Journal of Bacteriology* 175(1): 12–18, 1993.

Collinson, S. K., L. Emödy, P Doig, K.–H. Müller, T. Trust and W. Kay. 1992. "Thin, Aggregative Fimbriae Mediate Binding of *Salmonella enteritidis* to Fibronectin." Abstacts of the 92 General Meeting of the American Society for Microbiology, May 26–30, p. 27, B–401, New Orleans, LA.

Müller et al., "Fimbriation Genes of *Salmonella enteritidis*," *Journal of Bacteriology* 171(9): 4648–4654, 1989.

Feutrier et al., "Cloning and Expression of a *Salmonella enteritidis* Fimbrin Gene in *Escherichia coli*," *Journal of Bacteriology* 170(9): 4216–4222, 1988.

Feutrier et al., "Purification and Characterization of Fimbriae from *Salmonella enteritidis*," *Journal of Bacteriology* 168(1): 221–227, 1986.

Feutrier et al., "Novel Type 1 Fimbriae of *Salmonella Enteritidis*," in David L. Larke et al. (eds.), *Protein–Carbohydrate Interactions in Biological Systems*, Academic Press, 1986, pp. 103–107.

Thorns et al., "Detection of a Novel fimbrial Structure on the Surface of *Salmonella enteritidis* by Using a Monoclonal Antibody," *Journal of Clinical Microbiology* 28(11): 2409–2414, 1990.

Thorns et al., "Characterisation of monoclonal antibodies against a fimbrial structure of *Salmonella enteritidis* and certain other serogroup D salmonellae and their application as serotyping reagents," *Research in Veterinary Science* 53: 300–308, 1992.

Central Veterinary Laboratory, "A New Latex Agglutination Test Kit for the Identification OF *Salmonella Enteritidis*," SEFEX Product Advertisement.

Widenhorn et al., "Genetic Regulation of the Tricarboxylate Transport Operon (tctI) of *Salmonella typhimurium*," *Journal of Bacteriology* 171(8): 4436–4441, 1989.

Widenhorn et al., "Expression of the Divergent Tricaryboxylate Transport Operon (tctI) of *Salmonella typhimurium*," *Journal of Bacteriology* 170(7): 3223–3227, 1988.

Widenhorn et al., "Cloning and Properties of the *Salmonella typhimurium* tricarboxylate Transport Operon in *Escherichia coli*," *Journal of Bacteriology* 170(2): 883–888,1988.

Sweet et al., "Tricarboxylate–binding Proteins of *Salmonella typhimurium*," *Journal of Biological Chemistry* 259(3): 1586–1592, 1984.

(List continued on next page.)

*Primary Examiner*—Eggerton A. Campbell
*Attorney, Agent, or Firm*—Seed and Berry LLP

[57] ABSTRACT

An isolated nucleic acid molecule comprising the agfA gene of Salmonella. Methods and compositions suitable for diagnostic tests utilizing the isolated gene, and protein therefrom, to give highly specific diagnostic assays to Salmonella, and/or enteropathogenic bacteria of the family Enterobacteriaceae.

5 Claims, 22 Drawing Sheets

OTHER PUBLICATIONS

Somers and kay, "Genetic Fine Structure of the Tricarboxylate transport (tct) Locus of *Salmonella typhimurium*," *Mol. Gen. Genet.* 190: 20–26, 1983.

Sweet et al., "Purification and properties of a citrate-binding transport component, the C protien of *Salmonella typhimurium*," *Canadian Journal of Biochemistry* 57: 710–715, 1979.

Andrews, "A Review Of Culture Methods And Their Relation To Rapid Methods For The Detection Of Salmonella In Foods," *Food Technology* 39(3): 77–82, 1985.

Rubin, "Nucleic Acid Probes for the Identification of Salmonella," in Alberto J.L. Macario et al. (eds.), *Gene Probes for Bacteria*, Academic Press, 1990, pp. 323–352.

Blackburn, "Rapid and alternative methods for the detection of salmonellas in foods," *Journal of Applied Bacteriology* 75: 199–214, 1993.

Mattingly et al., "Use of Monoclonal Antibodies For The Detection of Salmonella In Foods," *Food technology* 39(3): 90–94, 1985.

Cox, "Salmonella Methodology Update," *Poultry Science* 67: 921–927, 1988.

Swaminathan et al., "Enzyme Immunoassay For Salmonella: One-Day Testing Is Now A Reality, " *Food Technology* 39(3): 83–89, 1985.

Fitts, "Development Of A DNA-DNA Hybridization Test For The Presence of Salmonella In Foods," *Food Technology* 39(3): 94–102, 1985.

Flowers, "Comparison of Rapid Salmonella Screening Methods And The Conventional Culture Method," *Food Technology* 39(3): 103–108, 1985.

Hartman and Minnich, "Automation for Rapid Identification of Salmonellae in Foods," *Journal of Food Protection* 44(5): 385–393, 1981.

Thomason, "Current Status of Immunofluorescent Methodology for Salmonellae," *Journal of Food Protection* 44(5) 381–384, 1981.

Tompkins et al, "Cloned, Random Chromosomal Sequences as Probes to Identify Salmonella Species," *Journal of Infectious Diseases* 154(1): 156–162, 1986.

Fitts et al., "DNA-DNA Hybridization Assay for Detection of Salmonella spp. in Foods," *Applied and Environmental Microbiology* 46: 1146–1151, 1983.

Ibrahim et al., "Rapid Detection of Salmonellae by Immunoassays with Titanous Hydroxide as the Solid Phase, " *Applied and Environmental Microbiology* 50(3): 670–675, 1985.

Rahn et al., "Amplification of an invA gene sequence of *Salmonella typhimurium* by polymerase chain reaction as a specific method of detection of Salmonella," *Molecular and Cellular Probes* 6: 271–279, 1992.

Chan et al., "Comparative Study of Colorimetric DNA Hybridization Method and Conventional Culture Procedure for Detection of Salmonella in Foods," *Journal Assoc. Off. Anal. Chem.* 73(3): 419–424, 1990.

Flowers et al., "DNA Hybridization Assay for Detection of Salmonella in Foods: Collaborative Study," *J. Assoc. Off. Anal. Chem.* 70(3): 521–529, 1987.

Aabo et al., "Salmonella identification by the polymerase chain reaction," *Molecular and Cellular Probes* 7: 171–178, 1993.

Spierings et al., "Characterization of the *Salmonella typhimurium* phoE gene and development of Salmonella-specific DNA probes," *Gene* 122: 45–52, 1992.

Widjojoatmodjo et al., "The Magnetic Immuno Polymerase Chain Reaction Assay for Direct Detection of Salmonellae in Fecal Samples," *Journal of Clinical Microbiology* 30(12): 3195–3199, 1992.

Cano et al., "Detection of salmonellas by DNA hybridization with a fluorescent alkaline phosphatase substrate," *Journal of Applied Bacteriology* 72: 393–399, 1992.

Knight et al., "Direct Detection of Salmonella spp. in Estuaries by Using a DNA Probe," *Applied and Environmental Microbiology* 56(4): 1059–1066, 1990.

Gopo et al., "Development of a Salmonella-specific biotinylated DNA probe for rapid routine identification of Salmonella," *Molecular and Cellular Probes* 2: 271–279, 1988.

Olsen et al., "Isolation of a Salmonella-specific DNA hybridization probe," *APMIS* 99: 114–120, 1991.

Widjojoatmodjo et al., "Evaluation of the Magnetic Immuno PCR Assay for Rapid Detections of Salmonella," *European Journal of Clinical Moicrobiology and Infectious Disease* 10(11): 935–938, 1991.

Halbrook et al., "Rapid detection of salmonella in foods—a convenient two-day procedure," *Letters in Applied Microbiology* 8: 139–142, 1989.

Krysinski and Heimsch, "Use of Enzyme-Labeled Antibodies to Detect Salmonella in Foods," *Applied and Environmental Microbiology* 33(4): 947–954, 1977.

Minnich et al., "Enzyme Immunoassay for Detection of Salmonellae in Foods," *Applied and Environmental Microbiology* 43(4): 877–883, 1982.

Anderson and Hartman, "Direct Immunoassay for Detection of Salmonellae in Foods and Feeds," *Applied and Environmental Microbiology* 49(5): 1124–1127, 1985.

Cherrington and Huis in't Veld, "Comparison of classical isolation protocols with a 24 h screen to detect viable salmonellas in faeces," *Journal of Applied Bacteriology* 75: 65–68, 1993.

Feldsine et al., "Polyclonal Enzyme Immunoassay Method for Detection of Motile and Non–Motile Salmonella in Foods: Collaborative Study," *Journal of AOAC International* 75(6): 1032–1044, 1992.

Ibrahim et al., "Immobilization of Microorganisms for Detection by Solid–Phase Immunoassays," *Journal of Clinical Microbiology* 22(3): 361–365, 1985.

Ibrahim and Lyons, "Detection of Salmonellae in Foods with an Enzyme Immunometric Assay," *Journal of Food Protection* 50(1): 59–61, 1987.

Mattingly, "An Enzyme Immunoassay for the Detection of All Salmonella Using a Combination of a Myeloma Protein and a Hybridoma Antibody," *Journal of Immunological Methods* 73: 147–156, 1984.

Smith et al., "M467: A Murine IgA Myeloma Protein That Binds a Bacterial Protein. I. Recognition of Common Antigenic Determinants on Salmonella Flagellins," *Journal of Immunology* 123(4): 1715–1720, 1979.

Brooks et al., "Experimental enzyme–linked amperometric immunosensors for the detection of salmonellas in foods," *Journal of Applied Bacteriology* 73: 189–196, 1992.

Robison et al., "Enzyme Immunoassay in Which a Myeloma Protein Is Used for Detection of Salmonellae," *Applied and Environmental Microbiology* 45(6): 1816–1821, 1983.

Lee et al., "Enzyme–Linked Immunosorbent Assay for *Salmonella typhimurium* in Food: Feasibility of 1–Day Salmonella Detection," *Applied and Environmental Microbiology* 56(6): 1541–1546, 1990.

Flint and Hartley, "Evaluation of the TECRA immunocapture ELISA for the detection of *Salmonella typhimurium* in foods," *Letters in Applied Microbiology* 17: 4–6, 1993.

Isomaki et al., "Serological Diagnosis of Salmonella Infections By Enzyme Immunoassay," *Lancet* (Jun. 24): 1411–1414, 1989.

D'Aoust and Sewell, "Detection of Salmonella by the Enzyme Immunoassay (EIA) Technique," *Journal of Food Science* 51(2): 484–488, 1986.

Emswiler-Rose et al., "An Enzyme Immunoassay Technique for Detection of Salmonellae in Meat and Poultry Products," *Journal of Food Science* 49: 1018–1020, 1984.

Mattingly and Gehle, "An Improved Enzyme Immunoassay for the Detection of Salmonella," *Journal of Food Science* 49: 807–809, 1984.

Todd et al., "Development of an enzyme–linked antibody hydrophobic grid membrane filter method for the detection of Salmonella in foods," *Food Microbiology* 10: 87–99, 1993.

Todd et al., "Evaluation of Salmonella antisera for an optimum enzyme–linked antibody detection of Salmonella using hydrophobic grid membrane filters," *Food Microbiology* 8: 311–324, 1991.

van Zijderveld, "Comparison of Four Different Enzyme–Linked Immunosorbent Assays for Serological Diagnosis of *Salmonella enteritidis* Infections in Experimentally Infected Chickens," *Journal of Clinical Microbiology* 30(10): 2560–2566, 1992.

Araj and das Chugh, "Detection of Salmonella spp. in Clinical Specimens by Capture Enzyme–Linked Immunosorbent Assay," *Journal of Clinical Microbiology* 25: 2150–2153, 1987.

Baay and Huis in't Veld, "Alternative antigens reduce cross–reactions in an ELISA for the detection of *Salmonella enteritidis* in poultry," *Journal of Applied Bacteriology* 74: 243–247, 1993.

Clark et al., "Detection of Salmonella in Foods using a Novel Coloured Latex Test," *Food and Agricultural Immunology* 1: 3–9, 1989.

Benge, "Detection of Salmonella Species in Faeces by Latex Agglutination in Enrichment Broth," *European Journal Clinical Microbiol. Infect. Dis.* 8(4): 294–298, 1989.

Dadrast et al., "Egg yolk antibody detection in identification of salmonella infected poultry," *Veterinary Record* 126: 219, 1990.

Lane et al., "Detection of Food Pathogens Using the Phage Rapid Identification Assay System," Vitek Systems Inc. and Bactomatic Inc.

Van Poucke, "Salmonella–TEK, a Rapid Screening Method for Salmonella Species in Food," *Applied and Environmental Microbiology* 56(4): 924–927, 1990.

Lambiri et al., "Comparison of the TECRA Salmonella Immunoassay with the conventional culture method," *Letters in Applied Microbiology* 11: 182–184, 1990.

Humbert et al., "Rapid detection of Salmonella from poultry meat products using the '1.2. Test®," *Letters in Applied Microbiology* 19:245–249, 1990.

Karlsson et al., "Application and Usefulness of Enzyme Immunoassay for Diagnosis of *Salmonella typhimurium* Infection," *Scandinavian Journal of Infectious Disease* 12: 41–47, 1980.

Kerr et al., "A comparison of three salmonella antigen–capture ELISAs and culture for veterinary diagnostic specimens," *Journal of Applied Bacteriology* 75: 164–167, 1993.

D'Aoust and Sewell, "Detection of Salmonella with the BioEnzabead™ Enzyme Immunoassay Technique," *Journal of Food Protection* 51(7): 538–541, 1988.

Nath et al., "Evaluation of Enrichment Protocols for the 1–2Test™ for Salmonella Detection in Naturally Contaminated Foods & Feeds," *Journal of Food Protection* 52(7): 498–499, 1989.

Oggel et al., "Modified 1–2 Test™ System as a Rapid Screening Method for Detection of Salmonella in Foods and Feeds," *Journal of Food Protection* 53(8): 656–658, 1990.

Flowers et al., "Visual Immunoassay for Detection of Salmonella in Foods: Collaborative Study," *Journal Assoc. Off. Anal. Chem.* 71(5): 973–980, 1988.

Curiale et al., "Comparison of Colorimetric Monoclonal Enzyme Immunoassay Screening Methods for Detection of Salmonella in Foods," *Journal Assoc. Off. Anal. Chem.* 73(1): 43–50, 1990.

Curiale et al., "Detection of Salmonellae and Other Enterobacteriaceae by Commercial Deoxyribonucleic Acid Hybridization and Enzyme Immunoassay Kits," *Journal of Food Protection* 53(12): 1037–1046, 1990.

Bouvet and Jeanjean, "Evaluation of Two Colored Latex Kits, the Wellcolex Colour Salmonella Test and the Wellcox Colour Shigella Test, for Serological Grouping of Salmonella and Shigella Species," *Journal of Clinical Microbiology* 30(8): 2184–2186, 1992.

International BioProducts, Inc., "Executive Summary: Comparison Guide For The AOAC Accepted Rapid Methods,".

International BioProducts, Inc., "Executive Summary: Comparison Guide For The Visual Immunoassay And The 1–2 Test,".

BioControl Systems, Inc., "1–2 Test®," *Technical Bulletin*, Dec. 1993.

Biocontrol Systems, Inc., "Assurance® EIA: Providing Unique Advantages for Rapid Bacterial Detection,".

"Unique™ Salmonella," *TECRA™ Technical Bulletin* (7).

Gene–Trak Systems, "Colorimetric Gene–Trak® Salmonella Assay," 1993.

Gene–Trak Systems Corporation, "Gene–Trak® Salmonella Assay: Colorimetric protoco Overview," 1993.

Dynatech Laboratories, Inc., "Q–Trol Salmonella: Salmonella Microelisa® –92 & Microelisa® –32 Detection Kit," Catalog Nos. 007–040–0460 (92 Test) & 007–040–0440 (32 Test), 1988.

Dynatech Laboratories, Inc., "Q–Trol Salmonella: Salmonella Detection Kit," Catalog No. 007–040–0410.

"1–2 Test®—Modified per Oggel: Directions for Use,".

Pro–Lab Diagnostics, "A Vision of the Future from Pro–Lab Diagnostics," *Advertisement*, 1994.

AMPCOR, Inc., "DipStick Salmonella Color Change Test Kit: For Detection of Salmonella sp. in fecal specimens," *Advertisement*.

Murex, "Wellcolex Colour Shigella: Colour latex test for the detection and species identification of Shigella," *Informational Brochure*, ZC51.

Murex, "Wellcolex Colour Salmonella: Colour latex test for the detection and serogroup identification of Salmonella," *Informational Brochure*, ZC50.

Krusell and Skovgaard, "Evaluation of a new semi–automated screening method for the detection of Salmonella in foods within 24 h," *International Journal of Food Microbiology* 20: 123–130, 1993.

Incstar Corporation, "Salmonella Fluoro–Kit™ Delayed Direct Fluorescent Antibody Test," *Instruction Manual*, Catalog No. 1903, 1991.

LAB M, "Microbial Confirmation Strips," *Instruction Manual and Informational Brochure*.

International BioProducts, Inc., "BioPro™ Salmonella Visual Immunoassay: A Final Action AOAC Approved Method for the Rapid Detection of Salmonella," *Informational Brochure*.

Organon Teknika Corporation, "Salmonella–Tek™ ELISA Test System: For the detection of Salmonella antigen in foods," *Instruction Manual*: 1993.

AMPCOR, "Dipstick Salmonella," *Instruction Manual*, Catalog No. 300–150, 1991.

Pro–Lab Diagnostics, "Vision Antisera," *Instruction Manual*, 1993.

Wellmark Diagnostics Ltd., "Wellcolex," *Advertisement*.

Wellmark Diagnostics Ltd., "Salmonella Agglutinating Sera For Slide and Tube Agglutination Tests," *Informational Brochure*.

Mansfield and Forsythe, "Immunomagnetic separation as an alternative to enrichment broth for Salmonella detection," *Letters in Applied Microbiology* 16: 122–125, 1993.

Torensma et al., "Monoclonal Antibodies That Detect Live Salmonellae," *Applied and Environmental Microbiology* 58(12): 3868–3872, 1992.

Holbrook et al., "Comparative evaluation of the Oxoid Salmonella Rapid Test with three other rapid salmonella methods," *Letters in Applied Microbiology* 9: 161–164, 1989.

Izat et al., "Comparison of the DNA Probe to Culture Methods for the Detection of Salmonella on Poultry Carcasses and Processing Waters," *Journal of Food Protection* 52(8) 564–570, 1989.

Scholl et al., "Clinical Application of Novel Sample Processing Technology for the Identification of Salmonellae by Using DNA Probes," *Journal of Clinical Microbiology* 28(2): 237–241, 1990.

Rose et al., "Evaluation of a Colorimetric DNA Hybridization Test for Detection of Salmonellae in Meat and Poultry Products," *Journal of Food Protection* 54(2): 127–130, 1991.

Gast and Beard, "Research Note: Detection of Salmonella Serogroup D–Specific Antibodies in the Yolks of Eggs Laid by Hens Infected with *Salmonella enteritidis*," *Poultry Science* 70: 1273–1276, 1991.

Lu et al., "Characterization and application of a murine monoclonal antibody that reacts specifically with the serogroup $D_1$ *Salmonella*," *FEMS Microbiology Letters* 80: 135–140, 1991.

McRill et al., "Application of the Peroxidase–Antiperoxidase Immunoassay to the Identification of Salmonellae from Pure Culture and Animal Tissue," *Journal of Clinical Microbiology* 20(2): 281–284, 1984.

Mohit et al., "A Simple Single–Step Immunoimmobilisation Method For The Detection Of Salmonella In The Presence Of Large Numbers Of Other Bacteria," *Journal of Medical Microbiology* 8: 173–176, 1975.

Appelmelk et al., "An Enzyme–Linked Immunosorbent Assay (ELISA) for the Measurement of Antibodies to Different Parts of the Gram–Negative Lipopolysaccharide Core Region," *Journal of Immunological Methods* 82: 199–207, 1985.

Choi et al., "Sandwich capture ELISA by a murine monoclonal antibody against a genus–specific LPS epitope for the detection of different common serotypes of salmonellas," *Journal of Applied Bacteriology* 72: 134–138, 1992.

Ibrahim et al., "Immunological relationships between Salmonella flagella and their potential application for salmonellae detection by immunoassay," *Med. Microbiol. Immunol.* 174: 87–99, 1985.

Aleixo et al., "Enzyme Immunoassay: Binding of Salmonella Antigens to Activated Microtiter Plates," *Journal of Immunoassay* 6(4): 391–407, 1985.

Vermunt et al., "Isolation of salmonellas by immunomagnetic separation," *Journal of Applied Bacteriology* 72: 112–118, 1992.

Gruenewald et al., "Identification of Salmonella Somatic and Flagellar Antigens by Modified Serological Methods," *Applied and Environmental Microbiology* 56(1): 24–30, 1990.

Pilantanapak et al., "Biotinylated probes for epidemiological studies of drug resistance in *Salmonella krefeld*," *Journal of Antimicrobial Chemotherapy* 25:593–603, 1990.

Qadri et al., "Sandwich Enzyme Immunoassay for Detection of *Salmonella typhi*," *Journal of Immunoassay* 11(2): 251–270, 1990.

Luk et al., "Epitope Mapping of Four Monoclonal Antibodies Recognizing the Hexose Core Domain of Salmonella Lipopolysaccharide," *Journal of Biological Chemistry* 266 (34): 23215–23225, 1991.

Greunewald et al., "Identification of Salmonella Somatic and Flagellar Antigens by Modified Serological Methods," *Applied and Environmental Microbiology* 56(1): 24–30, 1990.

Appassakij et al., "Enzyme–Linked Immunosorbent Assay for Detection of *Salmonella typhi* Protein Antigen," *Journal of Clinical Microbiology* 25(2): 273–277, 1987.

Muthukkumar and Muthukkaruppan, "Detection of porin antigen in serum for early diagnosis of mouse infections with *Salmonella typhimurium*," *FEMS Microbiology Immunology* 89: 147–154, 1992.

Luk and Lindberg, "Anti–Salmonella Lipopolysaccharide Monoclonal Antibodies: Characterization of Salmonella BO–, CO–, DO–, and EO–Specific Clones and Their Diagnostic Usefulness," *Journal of Clinical Microbiology* 29(11): 2424–2433, 1991.

Luk et al., "Characterisation and application of a murine monoclonal antibody specific for the serogroup $C_2$ Salmonella," *J. Med. Microbiol.* 26: 115–119, 1988.

Williams and Whittemore, "Serological Response of Chickens to *Salmonella thompson* and *Salmonella pullorum* Infections," *Journal of Clinical Microbiology* 9(1): 108–114, 1979.

Ekpo et al., "Monoclonal Antibodies to 52–Kilodalton Protein of *Salmonella typhi*," *Journal of Clinical Microbiology* 28(8): 1818–1821, 1990.

Lim, "A one–step two–particle latex immunoassay for the detection of *Salmonella typhi* endotoxin," *Journal of Immunological Methods* 135: 257–261, 1990.

Bettelheim and Maskill, "Investigation by Enzyme–Linked Immunosorbent Assay of Salmonella H Antigen–Antibody Reactions," *Journal of Clinical Microbiology* 21(5): 772–774, 1985.

Lim and Choy, "A spectrophotometric method for evaluating a latex agglutination assay of *Salmonella typhi* lipopolysaccharide," *Journal of Immunological Methods* 115: 269–274, 1988.

Chaicumpa et al., "Diagnosis of Typhoid Fever by Detection of *Salmonella typhi* Antigen in Urine," *Journal of Clinical Microbiology* 30(9): 2513–2515, 1992.

Caldwell et al., "Somatic and Flagellar Immunofluorescence of Salmonella," *Journal of Bacteriology* 92(4): 1177–1187, 1966.

Pai et al., "Characterization of monoclonal antibodies to the outer membrane protein (OmpD) of *Salmonella typhimurium*," *Canadian Journal of Microbiology* 38: 1102–1107, 1992.

Colwell et al., "Monoclonal Antibodies to Salmonella Lipopolysaccharide: Anti–O–Polysaccharide Antibodies Protect C3H Mice Against Challenge with Virulent *Salmonella typhimurium*," *Journal of Immunology* 133(2): 950–957, 1984.

Kang et al., "Evaluation of modified passive haemagglutination assay for Vi antibody estimation in *Salmonella typhi* infections," *Journal of Clinical Pathology* 45:740–741, 1992.

Luk and Lindberg, "Rapid and sensitive detection of Salmonella (O:6,7) by immunomagnetic monoclonal antibody–based assay," *Journal of Immunological Methods* 137: 1–8, 1991.

Smith et al., "Detection of *Salmonella dublin* mammary gland infection in carrier cows, using an enzyme–linked immunosorbent assay for antibody in milk or serum," *Am. J. Vet. Res.* 50(8): 1352–1360, 1989.

Ibrahim et al., "Production of Potent Salmonella H Antisera by Immunization with Polymeric Flagellins," *Journal of Clinical Microbiology* 22(3): 347–351, 1985.

Ekwall et al, "Specific Identification of Salmonella Serogroup E Antigen O3 by Immunofluorescence and Coaggulation with Antiserum Elicited by a Synthetic Trisaccharide–Bovine Serum Albumin Glycoconjugate," *Journal of Clinical Microbiology* 19(5): 699–702, 1984.

Maxwell, "Serological Diagnosis of Salmonella Infections," *Lancet* (Aug. 19): 456, 1989.

Barclay and Scott, "Serological Relationships between *Escherichia coli* and Salmonella Smooth–and Rough–Mutant Lipopolysaccharides as Revealed by Enzyme–Linked Immunosorbent Assay for Human Immunoglobulin G Anti-endotoxin Antibodies," *Infection and Immunity* 55(11): 2706–2714, 1987.

Durham et al., "Stability of Immunofluorescence Reactions Produced by Polyclonal and Monoclonal Antibodiy Conjugates for Rabies Virus," *Journal of Clinical Microbiology* 24(2): 301–303, 1986.

Turpin et al., "An ion–exchange based extraction method for the detection of salmonellas in soil," *Journal of Applied Bacteriology* 74: 181–190, 1993.

Hariharan et al., "Competitive Enzyme–Linked Immunosorbent Assay for Cholera–Related Enterotoxins in *Salmonella typhimurium*," *Journal of Clinical Microbiology* 24(2): 298–300, 1986.

Chart et al., "Serological response of chickens to *Salmonella enteritidis* infections," *Epidemiol. Infect.* 104: 63–71, 1990.

Stanley et al., "Molecular phylogenetic typing of pandemic isolates of *Salmonella enteritidis*," *FEMS Microbiology Letters* 90:153–160, 1992.

Rubin et al., "Development of a DNA Probe to Detect *Salmonella typhi*," *Journal of Clinical Microbiology* 22(4): 600–605, 1985.

Gibert et al., "Distribution of insertion sequence IS200 in Salmonella and Shigella," *Journal of General Microbiology* 136: 2555–2560, 1990.

Altwegg et al., "Ribosomal RNA Gene Restriction Patterns Provide Increased Sensitivity for Typing *Salmonella typhi* Strains," *Journal of Infectious Disease* 160(1): 145–149, 1989.

McLeod and Barrow, "Lipopolysaccharide–specific IgG in egg yolk from two chicken flocks infected with *Salmonella enteritidis*," *Letters in Applied Microbiology* 13: 294–297, 1991.

Kay, W. W. F. "Transport of carboxylic acids," pp. 385–411. In B. P. Rosen (eds.), Bacterial Transport. Marcel Dekker, New York, 1978.

Somers et al., "Fluorocitrate Resistant Tricarboxylate Transport Mutants of *Salmonella typhimurium*," *Mol. Gen. Genet.* 181: 338–345, 1981.

Kay and Cameron, "Transport of $C_4$–Dicarboxylic Acids in *Salmonella typhimurium*," *Archives of Biochemistry and Biophysics* 190(1): 281–289, 1978.

Ashton et al., "Citrate transport in *Salmonella typhimurium*: studies with 2–fluoro–L–erythro citrate as a substrate," *Canadian Journal of Biochemistry* 58(10): 797–803, 1980.

Kay et al., "Tricarboxylate Transport Systems: the tct Operon in *Salmonella typhimurium*," *Microbiology*: 34–37, 1984.

Kay and Cameron, "Citrate Transport in *Salmonella typhimurium*," *Archives of Biochemistry and Biophysics* 190(1): 270–280, 1978.

Tomas and Kay, "Tricarboxylate transport in a $Cit^+$ *Escherichia coli*: evidence for the role of an outer membrane protein," *Canadian Journal of Microbiology* 30: 916–921, 1984.

FIGURE 2A

```
                20                    40                    60                    80
GGGGATGTTGTGTAAAGATAAAAAAATAGTGATCCTTGTTTTTTTTCTTAAATTTTTAAAATGGCGTGAGTATATTAGCATCC
          100                   120   sefA          140            -10            *
GCACAGATAAATTGTGCGAATGCTAATAGTTGATTTTTGGAGATTTTGTAAT ATG CGT AAA TCA GCA TCT GCA GTA
*         *        **   IHF           SD   SefA     Met arg lys ser ala ser ala val
160                       180                        200                         220
GCA GTT CTT GCT TTA ATT GCA TGT GGC AGT GCC CAC GCA GCT GGC TTT GTT GGT AAC AAA GCA
ala val leu ala leu ile ala cys gly ser ala his ala ala gly phe val gly asn lys ala
                      240                       260                        280
GTG GTT CAG GCA GCG GTT ACT ATT GCA GCT CAG AAT ACA ACA TCA GCC AAC TGG AGT CAG GAT
val val gln ala ala val thr ile ala ala gln asn thr thr ser ala asn trp ser gln asp
                    300                       320                        340
CCT GGC TTT ACA GGG CCT GCT GTT GCT GCT GGT CAG AAA GTT GGT ACT CTC AGC ATT ACT GCT
pro gly phe thr gly pro ala val ala ala gly gln lys val gly thr leu ser ile thr ala
             360                        380                        400
ACT GGT CCA CAT AAC TCA GTA TCT ATT GCA GGT AAA GGG GCT TCG GTA TCT GGT GGT GTA GCC
thr gly pro his asn ser val ser ile ala gly lys gly ala ser val ser gly gly val ala
             420                        440                        460
ACT GTC CCG TTC GTT GAT GGA CAA GGA CAG CCT GTT TTC CGT GGG CGT ATT CAG GGA GCC AAT
thr val pro phe val asp gly gln gly gln pro val phe arg gly arg ile gln gly ala asn
         480                        500                        520
ATT AAT GAC CAA GCA AAT ACT GGA ATT GAC GGG CTT GCA GGT TGG CGA GTT GCC AGC TCT CAA
ile asn asp gln ala asn thr gly ile asp gly leu ala gly trp arg val ala ser ser gln
         540                        560                        580                  600
GAA ACG CTA AAT GTC CCT GTC ACA ACC TTT GGT AAA TCG ACC CTG CCA GCA GGT ACT TTC ACT
glu thr leu asn val pro val thr thr phe gly lys ser thr leu pro ala gly thr phe thr
                620
GCG ACC TTC TAC GTT CAG CAG TAT CAA AAC TAA
ala thr phe tyr val gln gln tyr gln asn XXX 640                   660                    680                    700
TTTAATTTTAAACTTTATAAATGCCCTCAATATGAGGGCATTTGGATAATTTTATTATTTTAAAAATATCTATTTTGAATAGATA
     720              740     sefB       760                         780
GGTTTTATGCTTCCATGCAAAAACTTAAAGAGGGATT    ATG TAT ATT TTG AAT AAA TTT ATA CGT AGA ACT
                                  SD  SefB Met tyr ile leu asn lys phe ile arg arg thr
                800                        820                        840
GTT ATC TTT TTC TTT TTT TGC TAC CTT CCA ATT GCT TCT TCG GAA AGT AAA AAA ATT GAG CAA
val ile phe phe phe phe cys tyr leu pro ile ala ser ser glu ser lys lys ile glu gln
         860                        880                        900
CCA TTA TTA ACA CAA AAA TAT TAT GGC CTA AGA TTG GGC ACT ACA CGT GTT ATT TAT AAA GAA
pro leu leu thr gln lys tyr tyr gly leu arg leu gly thr thr arg val ile tyr lys glu
         920                        940                        960
GAT GCT CCA TCA ACA AGT TTT TGG ATT ATG AAT GAA AAA GAA TAT CCA ATC CTT GTT CAA ACT
asp ala pro ser thr ser phe trp ile met asn glu lys glu tyr pro ile leu val gln thr
     980                       1000                       1020
CAA GTA TAT AAT GAT GAT AAA TCA TCA AAA GCT CCA TTT ATT GTA ACA CCA CCT ATT TTG AAA
gln val tyr asn asp asp lys ser ser lys ala pro phe ile val thr pro pro ile leu lys
1040                       1060                       1080                       1100
GTT GAA AGT AAT GCG CGA ACA AGA TTG AAG GTA ATA CCA ACA AGT AAT CTA TTC AAT AAA AAT
val glu ser asn ala arg thr arg leu lys val ile pro thr ser asn leu phe asn lys asn
                       1120                       1140                       1160
GAG GAG TCT TTG TAT TGG TTG TGT GTA AAA GGA GTC CCA CCA CTA AAT GAT AAT GAA AGC AAT
glu glu ser leu tyr trp leu cys val lys gly val pro pro leu asn asp asn glu ser asn
                       1180                       1200                       1220
AAT AAA AAC AAC ATA ACT ACG AAT CTT AAT GTG AAT GTG GTT ACG AAT AGT TGT ATT AAA TTA
asn lys asn asn ile thr thr asn leu asn val asn val thr asn ser cys ile lys leu
                  1240                       1260                       1280
ATT TAT AGG CCT AAA ACT ATA GAC TTA ACG ACA ATG GAG ATT GCA GAT AAA TTA AAG TTA GAG
ile tyr arg pro lys thr ile asp leu thr thr met glu ile ala asp lys leu lys leu glu
             1300                       1320                       1340
AGA AAA GGA AAT AGT ATA GTT ATA AAG AAT CCA ACA TCA TCA TAT GTG AAT ATT GCA AAT ATT
arg lys gly asn ser ile val ile lys asn pro thr ser ser tyr val asn ile ala asn ile
         1360                       1380                       1400
AAA TCT GGT AAT TTA AGT TTT AAT ATT CCA AAT GGA TAT ATT GAG CCA TTT GGA TAT GCT CAA
lys ser gly asn leu ser phe asn ile pro asn gly tyr ile glu pro phe gly tyr ala gln
      1420                      1440                       1460                      1480
TTA CCT GGT GGA GTA CAT AGT AAA ATA ACT TTG ACT ATT TTG GAT GAT AAC GGC GCT GAA ATT
leu pro gly gly val his ser lys ile thr leu thr ile leu asp asp asn gly ala glu ile
ATA AGA GAT TAT TAG
ile arg asp tyr XXX
```

FIGURE 2B

```
     1500  sefC           1520                        1540                         1560
TTTAAGGTGTAAACAAATG AAG AAA ACC ACA ATT ACT CTA TTT GTT TTA ACC AGT GTA TTT CAC TCT
     SD  SefC  Met lys lys thr thr ile thr leu phe val leu thr ser val phe his ser
                   1580                         1600                         1620
GGA AAT GTT TTC TCC AGA CAA TAT AAT TTC GAC TAT GGA AGT TTG AGT CTT CCT CCC GGT GAG
gly asn val phe ser arg gln tyr asn phe asp tyr gly ser leu ser leu pro pro gly glu
              1640                         1660                         1680
AAT GCA TCT TTT CTA AGT GTT GAA ACG CTT CCT GGT AAT TAT GTT GTT GAT GTA TAT TTG AAT
asn ala ser phe leu ser val glu thr leu pro gly asn tyr val val asp val tyr leu asn
         1700                         1720                         1740
AAT CAG TTA AAA GAA ACT ACT GAG TTG TAT TTC AAA TCA ATG ACT CAG ACT CTA GAA CCA TGC
asn gln leu lys glu thr thr glu leu tyr phe lys ser met thr gln thr leu glu pro cys
    1760                         1780                         1800
TTA ACA AAA GAA AAA CTT ATA AAG TAT GGG ATC GCC ATC CAG GAG CTT CAT GGG TTG CAG TTT
leu thr lys glu lys leu ile lys tyr gly ile ala ile gln glu leu his gly leu gln phe
1820                         1840                         1860
GAT AAT GAA CAA TGC GTT CTC TTA GAG CAT TCT CCT CTT AAA TAT ACT TAT AAC GCG GCT AAC
asp asn glu gln cys val leu leu glu his ser pro leu lys tyr thr tyr asn ala ala asn
   1880                         1900                         1920                    1940
CAA AGT TTG CTT TTA AAT GCA CCA TCT AAA ATT CTA TCT CCA ATA GAC AGT GAA ATT GCT GAT
gln ser leu leu leu asn ala pro ser lys ile leu ser pro ile asp ser glu ile ala asp
              1960                         1980                         2000
GAA AAT ATC TGG GAT GAT GGC ATT AAC GCT TTT CTT TTA AAT TAC AGA GCT AAT TAT TTG CAT
glu asn ile trp asp asp gly ile asn ala phe leu leu asn tyr arg ala asn tyr leu his
         2020                         2040                         2060
TCT AAG GTT GGA GGA GAA GAT TCA TAC TTT GGT CAA ATT CAA CCT GGT TTT AAT TTT GGT CCC
ser lys val gly gly glu asp ser tyr phe gly gln ile gln pro gly phe asn phe gly pro
    2080                         2100                         2120
TGG CGG CTA AGG AAT CTA TCA TCT TGG CAA AAC TTG TCA AGC GAA AAA AAA TTT GAA TCA GCA
trp arg leu arg asn leu ser ser trp gln asn leu ser ser glu lys lys phe glu ser ala
2140                         2160                         2180
TAT ATT TAT GCT GAG CGA GGT TTA AAA AAA ATA AAG AGC AAA CTA ACA GTT GGG GAC AAA TAT
tyr ile tyr ala glu arg gly leu lys lys ile lys ser lys leu thr val gly asp lys tyr
  2200                         2220                         2240
ACC AGT GCA GAT TTA TTC GAT AGC GTA CCA TTT AGA GGC TTT TCT TTA AAT AAA GAT GAA AGT
thr ser ala asp leu phe asp ser val pro phe arg gly phe ser leu asn lys asp glu ser
    2260                         2280                         2300
ATG ATA CCT TTC TCA CAG AGA ACA TAT TAT CCA ACA ATA CGT GGT ATT GCG AAA ACC AAT GCG
met ile pro phe ser gln arg thr tyr tyr pro thr ile arg gly ile ala lys thr asn ala
2320                         2340                         2360                    2380
ACT GTA GAA GTA AGA CAA AAT GGA TAC TTG ATA TAT TCT ACT TCA GTC CCC CCC GGG CAA TTC
thr val glu val arg gln asn gly tyr leu ile tyr ser thr ser val pro pro gly gln phe
              2400                         2420                         2440
GAG ATA GGT AGA GAA CAA ATT GCT GAT CTT GGT GTT GGG GTT GGG GTT CTT GAT GTT AGC ATT
glu ile gly arg glu gln ile ala asp leu gly val gly val gly val leu asp val ser ile
         2460                         2480                         2500
TAT GAA AAA AAT GGG CAG GTC CAA AAC TAT ACA GTG CCA TAT TCA ACT CCT GTA TTA TCT TTG
tyr glu lys asn gly gln val gln asn tyr thr val pro tyr ser thr pro val leu ser leu
    2520                         2540                         2560
CCT GAT GGA TAT TCT AAA TAT AGT GTA ACT ATT GGT AGA TAC AGG GAG GTT AAC AAT GAT TAT
pro asp gly tyr ser lys tyr ser val thr ile gly arg tyr arg glu val asn asn asp tyr
2580                         2600                         2620
ATC GAT CCT GTT TTT TTT GAA GGG ACT TAT ATA TAT GGT CTG CCT TAT GGG TTT ACT TTA TTT
ile asp pro val phe phe glu gly thr tyr ile tyr gly leu pro tyr gly phe thr leu phe
  2640                         2660                         2680
GGT GGA GTG CAA TGG GTA AAT ATT TAT AAT TCA TAT GCC ATA GGC GCA AGT AAA GAT ATT GGT
gly gly val gln trp val asn ile tyr asn ser tyr ala ile gly ala ser lys asp ile gly
    2700                         2720                         2740
GAG TAT GGT GCT CTG TCT TTT GAC TGG AAA ACA TCT GTT TCG AAG ACT GAT ACA TCC AAT GAA
glu tyr gly ala leu ser phe asp trp lys thr ser val ser lys thr asp thr ser asn glu
2760                         2780                         2800                    2820
AAT GGT CAT GCA TAT GGG ATT AGA TAC AAT AAA AAT ATC GCT CAG ACA AAC ACC GAA GTA TCT
asn gly his ala tyr gly ile arg tyr asn lys asn ile ala gln thr asn thr glu val ser
              2840                         2860                         2880
TTG GCT AGT CAT TAC TAT TAT TCG AAA AAT TAT AGA ACT TTT TCT GAA GCA ATT CAT AGT AGC
leu ala ser his tyr tyr tyr ser lys asn tyr arg thr phe ser glu ala ile his ser ser
         2900                         2920                         2940
GAG CAT GAT GAA TTT TAC GAT AAA AAT AAG AAA TCA ACA ACC TCT ATG TTA TTA AGT CAG GCA
glu his asp glu phe tyr asp lys asn lys lys ser thr thr ser met leu leu ser gln ala
    2960                         2980                         3000
TTA GGA TCT CTG GGT TCT GTT AAC TTA AGC TAC AAT TAT GAT AAA TAT TGG AAA CAT GAA GGT
leu gly ser leu gly ser val asn leu ser tyr asn tyr asp lys tyr trp lys his glu gly
3020                         3040                         3060
AAA AAA TCA ATA ATT GCT AGT TAT GGG AAG AAT TTA AAT GGT GTT TCG TTA TCG CTT TCA TAT
lys lys ser ile ile ala ser tyr gly lys asn leu asn gly val ser leu ser leu ser tyr
```

FIGURE 2C

```
          3080                    3100                      3120
ACG AAA AGT ACA TCA AAG ATT AGT GAA GAA AAT GAA GAT TTA TTC AGT TTT CTA CTC AGT GTA
thr lys ser thr ser lys ile ser glu glu asn glu asp leu phe ser phe leu leu ser val
     3140                    3160                      3180                      3200
CCT TTG CAA AAA CTT ACA AAT CAT GAA ATG TAT GCT ACA TAT CAA AAC TCA TCC TCT TCA AAG
pro leu gln lys leu thr asn his glu met tyr ala thr tyr gln asn ser ser ser ser lys
                        3220                      3240                      3260
CAT GAT ATG AAT CAT GAT TTA GGT ATT ACT GGT GTG GCA TTT AAT AGC CAA TTG ACA TGG CAA
his asp met asn his asp leu gly ile thr gly val ala phe asn ser gln leu thr trp gln
                   3280                      3300                      3320
GCA AGA GGG CAA ATA GAA GAT AAA TCG AAA AAT CAA AAG GCT ACA TTT TTA AAT GCT TCT TGG
ala arg gly gln ile glu asp lys ser lys asn gln lys ala thr phe leu asn ala ser trp
                   3340                      3360                      3380
CGA GGT ACT TAT GGG GAG ATC GGA GCA AAC TAT AGT CAT AAT GAA ATA AAT CGT GAT ATT GGG
arg gly thr tyr gly glu ile gly ala asn tyr ser his asn glu ile asn arg asp ile gly
                   3400                      3420                      3440
ATG AAT GTT TCT GGT GGG GTG ATT GCT CAT TCA TCA GGA ATT ACG TTT GGT CAG AGT ATA TCG
met asn val ser gly gly val ile ala his ser ser gly ile thr phe gly gln ser ile ser
                   3460                      3480                      3500
GAT ACT GCT GCA CTG GTA GAG GCT AAA GGT GTA AGT GGG GCA AAA GTT CTG GGC CTA CCA GGT
asp thr ala ala leu val glu ala lys gly val ser gly ala lys val leu gly leu pro gly
              3520                      3540                      3560
GTT AGA ACC GAT TTT AGA GGC TAT ACA ATA TCC AGT TAT CTT ACT CCA TAT ATG AAT AAC TTC
val arg thr asp phe arg gly tyr thr ile ser ser tyr leu thr pro tyr met asn asn phe
     3580                    3600                      3620                      3640
ATA TCT ATA GAT CCA ACA ACG TTA CCA ATA AAT ACG GAT ATT AGG CAA ACT GAT ATT CAA GTA
ile ser ile asp pro thr thr leu pro ile asn thr asp ile arg gln thr asp ile gln val
                   3660                      3680                      3700
GTT CCT ACC GAA GGT GCT ATT GTA AAA GCT GTA TAT AAA ACA AGC GTG GGT ACT AAT GCA TTA
val pro thr glu gly ala ile val lys ala val tyr lys thr ser val gly thr asn ala leu
                   3720                      3740                      3760
ATT AGA ATT ACA AGA ACA AAT GGA AAG CCA CTA GCT CTT GGC ACA GTT CTT TCA CTT AAG AAT
ile arg ile thr arg thr asn gly lys pro leu ala leu gly thr val leu ser leu lys asn
                   3780                      3800                      3820
AAT GAT GGA GTA ATC CAA TCA ACA TCT ATT GTT GGC GAA GAT GGT CAG GCA TAT GTA TCT GGA
asn asp gly val ile gln ser thr ser ile val gly glu asp gly gln ala tyr val ser gly
                   3840                      3860                      3880
TTG TCA GGA GTG CAA AAA TTA ATC GCT TCG TGG GGG AAT AAG CCC TCC GAT ACT TGT ACA GTT
leu ser gly val gln lys leu ile ala ser trp gly asn lys pro ser asp thr cys thr val
              3900                      3920                      3940
TTT TAC TCT CTT CCC GAT AAA AAC AAA GGT CAG ATT AGC TTT TTA AAT GGA GTG TGC AAA TGA
phe tyr ser leu pro asp lys asn lys gly gln ile ser phe leu asn gly val cys lys XXX
```

FIGURE 2D

*sefD*
```
        3960                        3980
ATG AAT CAG TAT AAT TCG TCA ATA CCT AAG TTC ATT GTC TCT GTT
met asn gln tyr asn ser ser ile pro lys phe ile val ser val
```

*sefD*
```
   4000                        4020                        4040
TTT CTG ATT GTT ACT GGT TTT TTC AGC TCA ACT ATT AAA GCA CAA
phe leu ile val thr gly phe phe ser ser thr ile lys ala gln 4060                        4080
GAA CTT AAA TTA ATG ATT AAA ATA AAT GAG GCT GTT TTT TAT GAC
glu leu lys leu met ile lys ile asn glu ala val phe tyr asp 4100                        4120
CGT ATT ACA AGT AAT AAA ATA ATA GGT ACG GGG CAT CTA TTT AAC
arg ile thr ser asn lys ile ile gly thr gly his leu phe asn 4140                        4160
AGA GAG GGA AAA AAA ATC CTC ATT AGT TCA AGT TTA GAA AAA ATT
arg glu gly lys lys ile leu ile ser ser ser leu glu lys ile 4180                        4200                        4220
AAA AAT ACC CCA GGG GCA TAT ATT ATT AGA GGT CAG AAT AAC TCA
lys asn thr pro gly ala tyr ile ile arg gly gln asn asn ser 4240                        4200
GCC CAT AAG CTT AGG ATA AGA ATA GGT GGA GAA GAC TGG CAA CCA
ala his lys leu arg ile arg ile gly gly glu asp trp gln pro 4280                        4300
GAT AAT TCA GGT ATT GGT ATG GTA TCT CAT TCT GAT TTT ACT AAT
asp asn ser gly ile gly met val ser his ser asp phe thr asn 4320                        4340
GAA TTT AAT ATT TAT TTT TTT GGG AAT GGA GAC ATT CCT GTT GAC
glu phe asn ile tyr phe phe gly asn gly asp ile pro val asp 4360                        4380                        4400
ACA TAT TTA ATA AGC ATA TAT GCG ACA GAA ATT GAA TTA TAA TAA
thr tyr leu ile ser ile tyr ala thr glu ile glu leu XXX XXX
```

FIGURE 3A

```
                               478/11
TC ACC CAC CCA TTT CTG ATT CGG GCC ACT GGC GTA AAA GCC CTG CTT CAG CAG ATT CTC
AG TGG GTG GGT AAA GAC TAA GCC CGG TGA CCG CAT TTT CGG GAC GAA GTC GTC TAA GAG

OPA gly gly met glu ser glu pro trp gln arg leu leu gly ala glu ala ser glu arg

508/21                         538/31
                                                            val lys leu ser pro
                                                sefU1 →
TGG ACT GGC AGA CCA TGT TCG CGG TAA CTG ACT GGA CTG ATC TTC CGT GAA GCT TTC GCC
ACC TGA CCG TCT GGT ACA AGC GCC ATT GAC TGA CCT GAC TAG AAG GCA CTT CGA AAG CGG ser gln cys val met asn ala thr val ser gln val ser arg gly his leu lys arg gly 568/41                         598/51
ala ala leu pro ala gln ala gly arg tyr gly phe tyr val ile his pro ser leu ser CGC AGC ACT GCC GGC GCA GGC TGG CCG CTA CGG TTT TTA TGT TAT ACA CCC GTC CCT GAG
GCG TCG TGA CGG CCG CGT CCG ACC GGC GAT GCC AAA AAT ACA ATA TGT GGG CAG GGA CTC cys cys gln arg arg leu ser ala ala val thr lys ile asn tyr val arg gly gln ala 628/61                         658/71
thr lys leu ile arg gln ala trp arg thr val ala leu phe cys val thr glu cys leu CAC GAA GCT CAT CCG TCA GGC GTG GCG TAC CGT AGC GCT GTT TTG CGT CAC TGA ATG CCT
GTG CTT CGA GTA GGC AGT CCG CAC CGC ATG GCA TCG CGA CAA AAC GCA GTG ACT TAC GGA arg leu glu asp thr leu arg pro thr gly tyr arg gln lys ala asp ser phe ala glu 688/81                         718/91
pro tyr asp val ile thr asp lys ser glu leu leu thr pro asp val pro ala val thr CCC GTA CGA CGT TAT CAC AGA CAA GTC GGA ACT GCT GAC GCC GGA CGT ACC AGC TGT TAC
GGG CAT GCT GCA ATA GTG TCT GTT CAG CCT TGA CGA CTG CGG CTT GCA TGG TCG ACA ATG arg val val asn asp cys val leu arg phe gln gln arg arg val tyr trp ser asn arg 748/101                        778/111
gly asn leu lys tyr thr ala tyr gly phe asp thr glu leu ser leu met phe phe asp GGG CAA CCT GAA GTA CAC GGC ATA TGG CTT TGA TAC TGA ACT CAG CCT GAT GTT TTT CGA
CCC GTT GGA CTT CAT GTG CCG TAT ACC GAA ACT ATG ACT TGA GTC GGA CTA CAA AAA GCT ala val gln leu val arg cys ile ala lys ile ser phe glu ala gln his lys glu ile 808/121                        838/131
glu asp ile leu his phe arg arg phe ala lys tyr val ala thr ile leu glu asn gly TGA AGA CAT ACT TCA TTT CAG GCG TTT CGC GAA GTA TGT CGC GAC CAT TCT GGA GAA TGG
ACT TCT GTA TGA AGT AAA GTC CGC AAA GCG CTT CAT ACA GCG CTG GTA AGA CCT CTT ACC phe val tyr lys met glu pro thr glu arg leu ile asp arg gly asn gln leu ile thr
```

FIGURE 3B

```
868/141                              898/151
gln phe leu ile pro phe cys gln leu thr leu gln thr asp asp phe cys gly his leu TCA GTT CCT CAT CCC GTT CTG CCA GTT GAC GCT TCA GAC GGA CGA TTT CTG CGG ACA TCT
AGT CAA GGA GTA GGG CAA GAC GGT CAA CTG CGA AGT CTG CCT GCT AAA GAC GCC TGT AGA leu glu glu asp arg glu ala leu gln arg lys leu arg val ile glu ala ser met glu 928/161                              958/171
leu phe ala phe arg arg arg glu leu ile leu leu phe ala ser pro val val glu leu CCT GTT CGC GTT CAG AAG AAG AGA GCT GAT TTT GCT GTT TGC TTC GCC AGT TGT AGA GCT
GGA CAA GCG CAA GTC TTC TTC TCT CGA CTA AAA CGA CAA ACG AAG CGG TCA ACA TCT CGA gln glu arg glu ser ser ser leu gln asn gln gln lys ser arg trp asn tyr leu gln 988/181                              1018/191
arg phe ile gln val lys leu ala gly ser arg ser his pro asn ala leu ala ser phe GCG ATT CAT ACA GGT TAA GCT CGC TGG TAG CCG CAG CCA TCC CAA TGC GTT AGC CAG TTT
CGC TAA GTA TGT CCA ATT CGA GCG ACC ATC GGC GTC GGT AGG GTT ACG CAA TCG GTC AAA
                                              ◄────── sefU2 ser glu tyr leu asn leu glu ser thr ala ala ala met

1048/201                             1078/211
lys ala ser ser arg asn ser gly val cys cys leu his gly phe leu val val asp ala CAA GGC TTC GTC GCG AAA TTC AGG CGT ATG TTG CTT GCA TGG CTT TTT GGT GGT TGA TGC
GTT CCG AAG CAG CGC TTT AAG TCC GCA TAC AAC GAA CGT ACC GAA AAA CCA CCA ACT ACG 1108/221
ala phe val met OPA

TGC TTT TGT CAT GTG A
ACG AAA ACA GTA CAC T
```

FIGURE 4A

```
         3303          3312          3321          3330          3339          3348
ACC GGG GTT TAT CGC TTT ACC TTT GAC AGC GTT CAT CTT TCC GAC GGC GTA CAG
--- --- --- --- --- --- --- --- --- --- --- --- --- --- --- --- --- ---
Arg Gly Leu Ser Leu Tyr Leu *** Gln Arg Ser Ser Phe Arg Arg Arg Thr Val 3357          3366          3375          3384          3393          3402
TTT ATC GTC GTG GTG ATC GGC CTG TTC TCG GTA TCA GAA ATA CTT TTA ATG CTG
--- --- --- --- --- --- --- --- --- --- --- --- --- --- --- --- --- ---
Tyr Arg Arg Gly Asp Arg Pro Val Leu Gly Ile Arg Asn Thr Phe Asn Ala Gly 3411          3420          3429          3438          3447          3456
GAA CAT ACC AGC AGC GGG CAA ACA ATG GTC CGC AAA ACG GGT CGA ATG TTG TTC
--- --- --- --- --- --- --- --- --- --- --- --- --- --- --- --- --- ---
Thr Tyr Gln Gln Arg Ala Asn Asn Gly Pro Gln Asn Gly Ser Asn Val Val Gln 3465          3474          3483          3492          3501          3510
AAC CTG AAA GAA GGC GCG CAG TGT ATC GGC ACC ACC CTG CGT TCT TCG GTA ATC
--- --- --- --- --- --- --- --- --- --- --- --- --- --- --- --- --- ---
Pro Glu Arg Arg Arg Ala Val Tyr Arg His His Pro Ala Phe Phe Gly Asn Arg 3519          3528          3537          3546          3555          3564
GGC TTT TTT GTC GGC GTA TTG CCC GGC GCC GGG CGA CCA TTG CCA GCG CCA TTA
--- --- --- --- --- --- --- --- --- --- --- --- --- --- --- --- --- ---
Leu Phe Cys Arg Arg Ile Ala Arg Arg Arg Ala Thr Ile Ala Ser Ala Ile Thr 3573          3582          3591          3600          3609          3618
CCT ATA TGA CCG AGA AAA AAC TCA GCG GCA ACA GCG ATA GCT TCG GCA AAG GGG
--- --- --- --- --- --- --- --- --- --- --- --- --- --- --- --- --- ---
Tyr Met Thr Glu Lys Lys Leu Ser Gly Asn Ser Asp Ser Phe Gly Lys Gly Asp 3627          3636          3645          3654          3663          3672
ATA TTC GCG GCG TCG CGG CGC CGG AGG CGG CAA ACA ACG CCT CTG CCT GCG GCT
--- --- --- --- --- --- --- --- --- --- --- --- --- --- --- --- --- ---
Ile Arg Gly Val Ala Ala Pro Glu Ala Ala Asn Asn Ala Ser Ala Cys Gly Ser 3681          3690          3699          3708          3717          3726
CCT TCA TCC CGA TGC TGA CGC TGG GCG TTC CCG GTT CCG GCA CTA CGG CAG TGA
--- --- --- --- --- --- --- --- --- --- --- --- --- --- --- --- --- ---
Phe Ile Pro Met Leu Thr Leu Gly Val Pro Gly Ser Gly Thr Thr Ala Val Met 3735          3744          3753          3762          3771          3780
TGA TGG GGG CGC TGA CGC TGT ACA ACA TCA CGC CAG GCC CGG CGA TGT TCA CCG
--- --- --- --- --- --- --- --- --- --- --- --- --- --- --- --- --- ---
Met Gly Ala Leu Thr Leu Tyr Asn Ile Thr Pro Gly Pro Ala Met Phe Thr Glu 3789          3798          3807          3816          3825          3834
AAC AGC CGG ATA TCG TCT GGG GAC TCA TCG CTG CGC TGC TGA TTG CGA ACG TGA
--- --- --- --- --- --- --- --- --- --- --- --- --- --- --- --- --- ---
Gln Pro Asp Ile Val Trp Gly Leu Ile Ala Ala Leu Leu Ile Ala Asn Val Met 3843          3852          3861          3870          3879          3888
TGC TGC TGA TCA TGA ATA TCC CGT TGA TCG GTC TGT TCA CCC GTA TGC TCA CCA
--- --- --- --- --- --- --- --- --- --- --- --- --- --- --- --- --- ---
Leu Leu Ile Met Asn Ile Pro Leu Ile Gly Leu Phe Thr Arg Met Leu Thr Ile
```

FIGURE 4B

```
       3897        3906        3915        3924        3933        3942
TTC CGC TGT GGT TCC TGG TAC CCG CCA TCG CTG CCG TAT CGG CGG TGG GGG TGT
--- --- --- --- --- --- --- --- --- --- --- --- --- --- --- --- --- ---
Pro Leu Trp Phe Leu Val Pro Ala Ile Ala Ala Val Ser Ala Val Gly Val Tyr 3951        3960        3969        3978        3987        3996
ATG CGG TAC ACA GCA CCA CCT TCG ATC TGG TGC TGA TGG TCG CGC TCG GCG TGT
--- --- --- --- --- --- --- --- --- --- --- --- --- --- --- --- --- ---
Ala Val His Ser Thr Thr Phe Asp Leu Val Leu Met Val Ala Leu Gly Val Leu 4005        4014        4023        4032        4041        4050
TAG GGT ACA TTT TAC GTA AAA TGC ACT TCC CCA TGT CAC CGC TGA TCC TGG GGT
--- --- --- --- --- --- --- --- --- --- --- --- --- --- --- --- --- ---
Gly Tyr Ile Leu Arg Lys Met His Phe Pro Met Ser Pro Leu Ile Leu Gly Phe 4059        4068        4077        4086        4095        4104
TCG TAC TGG GGG AAA TGC TGG AGC AGA ACC TGC GTC GCG CAC TCT CCA TCA GTA
--- --- --- --- --- --- --- --- --- --- --- --- --- --- --- --- --- ---
Val Leu Gly Glu Met Leu Glu Gln Asn Leu Arg Arg Ala Leu Ser Ile Ser Asn 4113        4122        4131        4140        4149        4158
ACG GCA ATA TGG CGA TTT TGT GGC AAA GCG GCG TTG CCA AAG CCC TGC TGA TCA
--- --- --- --- --- --- --- --- --- --- --- --- --- --- --- --- --- ---
Gly Asn Met Ala Ile Leu Trp Gln Ser Gly Val Ala Lys Ala Leu Leu Ile Met 4167        4176        4185        4194        4203        4212
TGG CGA TCA TGG TCA TTG TCG TAC CGC CAG TGT TAC GTC TGC TCC GTA AAC ACA
--- --- --- --- --- --- --- --- --- --- --- --- --- --- --- --- --- ---
Ala Ile Met Val Ile Val Val Pro Pro Val Leu Arg Leu Leu Arg Lys His Ser 4221        4230        4239        4248        4257        4266
GCC GTA AAC CGC AGG TTG ACG CCG GTT AAT TGA CTG CTG AAA TAC GTT GTA CTT
--- --- --- --- --- --- --- --- --- --- --- --- --- --- --- --- --- ---
Arg Lys Pro Gln Val Asp Ala Gly *** Leu Thr Ala Glu Ile Arg Cys Thr Cys 4275        4284        4293        4302        4311        4320
GTC CGG CCT ACG CGC TCA TGT GTC AGG CCG GGC ACA TCC CCG CCA GCA TTC ACT
--- --- --- --- --- --- --- --- --- --- --- --- --- --- --- --- --- ---
Pro Ala Tyr Ala Leu Met Cys Gln Ala Gly His Ile Pro Ala Ser Ile His Phe 4329        4338        4347        4356        4365        4374
TTC CCC ATA ACG CCT CTC ATT TTA CAC CCC TTC TTG CCG TTG TCA GGC TCG TGG
--- --- --- --- --- --- --- --- --- --- --- --- --- --- --- --- --- ---
Pro His Asn Ala Ser His Phe Thr Pro Leu Leu Ala Val Val Arg Leu Val Ala 4383        4392        4401        4410        4419
CGC CGT TAA CCT CAC CCT TTG CAT TGT TAA ATA TTT GTT GTT TTT G
Pro Leu Thr Ser Pro Phe Ala Leu Leu Asn Ile Cys Cys Phe ***
```

FIGURE 5

```
         2735        2744        2753        2762        2771        2780
5' ATG GAT ACC TGG ATA TAT CTT TCT CAG GGC TTT GCG GTG GCG ATG ACG CCG GAA
   Met Asp Thr Trp Ile Tyr Leu Ser Gln Gly Phe Ala Val Ala Met Thr Pro Glu 2789        2798        2807        2816        2825        2834
   AAC CTG GTT ATC GCG TTG ATT GGC TGC TTC GTG GGC ACG ATC GTC GGT CTG CTG
   Asn Leu Val Ile Ala Leu Ile Gly Cys Phe Val Gly Thr Ile Val Gly Leu Leu 2843        2852        2861        2870        2879        2888
   CCG GGT CTG GGA CCG ATC AAC GGC GTG GCA ATC TTA CTG CCG CTG GCC TTT GCG
   Pro Gly Leu Gly Pro Ile Asn Gly Val Ala Ile Leu Leu Pro Leu Ala Phe Ala 2897        2906        2915        2924        2933        2942
   TTG CAT CTG CCT GCG GAG TCG GCG CTA ATT CTG CTG GCG ACG GTG TAC ATT GGC
   Leu His Leu Pro Ala Glu Ser Ala Leu Ile Leu Leu Ala Thr Val Tyr Ile Gly 2951        2960        2969        2978        2987        2996
   TGT GAG TAT GGC GGC AGG ATC TCC TCC ATA TTG CTC AAC GTC CCC GGC GAT GCG
   Cys Glu Tyr Gly Gly Arg Ile Ser Ser Ile Leu Leu Asn Val Pro Gly Asp Ala 3005        3014        3023        3032        3041        3050
   GCG GCG ATC ATG ACG GCG CTG GAC GGT TAC CCG ATG GCG CAG CAA GGG AAA GGC
   Ala Ala Ile Met Thr Ala Leu Asp Gly Tyr Pro Met Ala Gln Gln Gly Lys Gly 3059        3068        3077        3086        3095        3104
   GGC GTA GCG CTG TCG ATT TCC GCA GTC AGC TCA TTT TTC GGT TCA TTA ATC GCT
   Gly Val Ala Leu Ser Ile Ser Ala Val Ser Ser Phe Phe Gly Ser Leu Ile Ala 3113        3122        3131        3140        3149        3158
   ATC GGC GGC ATC ATT CTG TTC GCC CCT TTA CTG GCG CAA TGG TCG CTG GCC TTT
   Ile Gly Gly Ile Ile Leu Phe Ala Pro Leu Leu Ala Gln Trp Ser Leu Ala Phe 3167        3176        3185        3194        3203        3212
   GGG CCG GCG GAA TAT TTC GCC TTA ATG GTT TTT GCC ATC GCC TGT CTT GGC AGC
   Gly Pro Ala Glu Tyr Phe Ala Leu Met Val Phe Ala Ile Ala Cys Leu Gly Ser 3221        3230
   ATG ATG GCG CAA AAC CCG GCT TAA 3'
   Met Met Ala Gln Asn Pro Ala ***
```

FIGURE 6A

```
           1301          1310          1319          1328          1337          1346
5' ATG AAA AAA CAA TTA CTT CGT ACC CTT ACT GCA AGC ATT TTA TTA ATG AGT ACC
   Met Lys Lys Gln Leu Leu Arg Thr Leu Thr Ala Ser Ile Leu Leu Met Ser Thr 1355          1364          1373          1382          1391          1400
   TCT GTT CTG GCG CAG GAG GCG CCG TCG CGA ACG GAA TGT ATC GCG CCA GCC AAA
   Ser Val Leu Ala Gln Glu Ala Pro Ser Arg Thr Glu Cys Ile Ala Pro Ala Lys 1409          1418          1427          1436          1445          1454
   CCT GGC GGC GGT TTC GAC CTC ACC TGT AAG CTG ATT CAG GTG AGT TTG CTG GAG
   Pro Gly Gly Gly Phe Asp Leu Thr Cys Lys Leu Ile Gln Val Ser Leu Leu Glu 1463          1472          1481          1490          1499          1508
   ACT GGC GCT ATC GAG AAA CCC ATG CGG GTA ACG TAT ATG CCC GGC GGC GTC GGC
   Thr Gly Ala Ile Glu Lys Pro Met Arg Val Thr Tyr Met Pro Gly Gly Val Gly 1517          1526          1535          1544          1553          1562
   GCT GTG GCC TAT AAC GCG ATA GTC GCC CAA CGC CCT GGC GAA CCC GGG ACT GTG
   Ala Val Ala Tyr Asn Ala Ile Val Ala Gln Arg Pro Gly Glu Pro Gly Thr Val 1571          1580          1589          1598          1607          1616
   GTC GCC TTT TCC GGC GGT TCG CTG CTC AAC CTG TCG CAG GGG AAA TTT GGT CGC
   Val Ala Phe Ser Gly Gly Ser Leu Leu Asn Leu Ser Gln Gly Lys Phe Gly Arg 1625          1634          1643          1652          1661          1670
   TAC GGC GTG GAT GAT GTG CGC TGG CTG GCA AGC GTG GGC ACT GAT TAC GGC ATG
   Tyr Gly Val Asp Asp Val Arg Trp Leu Ala Ser Val Gly Thr Asp Tyr Gly Met 1679          1688          1697          1706          1715          1724
   ATC GCC GTG CGT GCG GAT TCT CCG TGG AAA ACG CTG AAA GAT CTG ATG ACG GCG
   Ile Ala Val Arg Ala Asp Ser Pro Trp Lys Thr Leu Lys Asp Leu Met Thr Ala 1733          1742          1751          1760          1769          1778
   ATG GAA AAA GAT CCC AAC AGC GTG GTC ATT GGC GCT GGC GCC TCT ATT GGC AGC
   Met Glu Lys Asp Pro Asn Ser Val Val Ile Gly Ala Gly Ala Ser Ile Gly Ser 1787          1796          1805          1814          1823          1832
   CAG GAC TGG ATG AAG TCG GCA TTG CTG GCG CAA AAG GCG AAC GTC GAC CCG CAC
   Gln Asp Trp Met Lys Ser Ala Leu Leu Ala Gln Lys Ala Asn Val Asp Pro His 1841          1850          1859          1868          1877          1886
   AAG ATG CGC TAC GTT GCC TTT GAG GGC GGC GGC GAG CCG GTG ACG GCA TTA ATG
   Lys Met Arg Tyr Val Ala Phe Glu Gly Gly Gly Glu Pro Val Thr Ala Leu Met 1895          1904          1913          1922          1931          1940
   GGC AAC CAT GTT CAG GTT GTC TCC GGC GAT CTC AGT GAA ATG GTG CCT TAT CTG
   Gly Asn His Val Gln Val Val Ser Gly Asp Leu Ser Glu Met Val Pro Tyr Leu 1949          1958          1967          1976          1985          1994
   GGC GGC GAC AAA ATC CGC GTG CTT GCC GTC TTT TCA GAA AAT CGT CTG CCG GGC
   Gly Gly Asp Lys Ile Arg Val Leu Ala Val Phe Ser Glu Asn Arg Leu Pro Gly
```

FIGURE 6B

```
         2003           2012           2021           2030           2039           2048
CAG CTT GCC AAT ATC CCT ACC GCT AAA GAA CAG GGG TAC GAC CTG GTG TGG CCG
Gln Leu Ala Asn Ile Pro Thr Ala Lys Glu Gln Gly Tyr Asp Leu Val Trp Pro 2057           2066           2075           2084           2093           2102
ATT ATT CGC GGC TTC TAC GTC GGG CCC AAA GTC AGC GAT GCC GAT TAC CAG TGG
Ile Ile Arg Gly Phe Tyr Val Gly Pro Lys Val Ser Asp Ala Asp Tyr Gln Trp 2111           2120           2129           2138           2147           2156
TGG GTG GAT ACC TTC AAG AAG CTC CAG CAA ACC GAC GAG TTT AAA AAG CAG CGC
Trp Val Asp Thr Phe Lys Lys Leu Gln Gln Thr Asp Glu Phe Lys Lys Gln Arg 2165           2174           2183           2192           2201           2210
GAT CTG CGC GGC CTG TTT GAG TTC GAC ATG ACC GGC CAG CAG CTC GAT GAC TAC
Asp Leu Arg Gly Leu Phe Glu Phe Asp Met Thr Gly Gln Gln Leu Asp Asp Tyr 2219           2228           2237           2246           2255           2264
GTG AAA AAA CAG GTT ACT GAT TAC CGT GAA CAG GCG AAA GCC TTC GGA CTC GCG
Val Lys Lys Gln Val Thr Asp Tyr Arg Glu Gln Ala Lys Ala Phe Gly Leu Ala

AAA TAA 3'
Lys ***
```

FIGURE 7A

```
                  •10          •                   •                    •50
          GTC GTA CCA CAG TGG GGC GGC GGC GGT AAT CAT AAC GGC GGC GGC AAT AGT TCC GGC CCG
          CAG CAT GGT GTC ACC CCG CCG CCG CCA TTA GTA TTG CCG CCG CCG TTA TCA AGG CCG GGC
          val val pro gln trp gly gly gly gly asn his asn gly gly gly asn ser ser gly pro
           2           5                       10                  15                  20

•                   •                    •100        •          •
          GAC TCA ACG TTG AGC ATT TAT CAG TAC GGT TCC GCT AAC GCT GCG CTT GCT CTG CAA AGC
          CTG AGT TGC AAC TCG TAA ATA GTC ATG CCA AGG CGA TTG CGA CGC GAA CGA GAC GTT TCG
          asp ser thr leu ser ile tyr gln tyr gly ser ala asn ala ala leu ala leu gln ser
                          25                  30                  35                  40

•                   •150        •                   •                  •
          GAT GCC CGT AAA TCT GAA ACG ACC ATT ACC CAG AGC GGT TAT GGT AAC GGC GCC GAT GTA
          CTA CGG GCA TTT AGA CTT TGC TGG TAA TGG GTC TCG CCA ATA CCA TTG CCG CGG CTA CAT
          asp ala arg lys ser glu thr thr ile thr gln ser gly tyr gly asn gly ala asp val
                          45                  50                  55                  60

•           •200        •                   •                  •
          GGC CAG GGT GCG GAT AAT AGT ACT ATT GAA CTG ACT CAG AAT GGT TTC AGA AAT AAT GCC
          CCG GTC CCA CGC CTA TTA TCA TGA TAA CTT GAC TGA GTC TTA CCA AAG TCT TTA TTA CGG
          gly gln gly ala asp asn ser thr ile glu leu thr gln asn gly phe arg asn asn ala
                          65                  70                  75                  80

•250       •                   •                   •                   •300
          ACC ATC GAC CAG TGG AAC GCT AAA AAC TCC GAT ATT ACT GTC GGC CAA TAC GGC GGT AAT
          TGG TAG CTG GTC ACC TTG CGA TTT TTG AGG CTA TAA TGA CAG CCG GTT ATG CCG CCA TTA
          thr ile asp gln trp asn ala lys asn ser asp ile thr val gly gln tyr gly gly asn
                          85                  90                  95                 100

•                   •                   •              •350        •
          AAC GCC GCG CTG GTT AAT CAG ACC GCA TCT GAT TCT GAC TCT TAT ACA CAA GTA GCG TCC T
          TTG CGG CGC GAC CAA TTA GTC TGG CGT AGA CTA AGA CTG AGA ATA TGT GTT CAT CGC AGG A
          asn ala ala leu val asn gln thr ala ser asp ser asp ser tyr thr gln val ala ser
                         105                 110
```

FIGURE 7B

```
1/1                                      31/11
ATG AAA CTT TTA AAA GTG GCA GCA TTC GCA GCA ATC GTA GTT TCT GGC AGT GCT CTG GCT
Met lys leu leu lys val ala ala phe ala ala ile val val ser gly ser ala leu ala 61/21                                    91/31
GGC GTC GTT CCA CAA TGG GGC GGC GGC GGT AAT CAT AAC GGC GGC GGC AAT AGT TCC GGC
gly val val pro gln trp gly gly gly gly asn his asn gly gly gly asn ser ser gly 121/41                                   151/51
CCG GAC TCA ACG TTG AGC ATT TAT CAG TAC GGT TCC GCT AAC GCT GCG CTT GCT CTG CAA
pro asp ser thr leu ser ile tyr gln tyr gly ser ala asn ala ala leu ala leu gln 181/61                                   211/71
AGC GAT GCC CGT AAA TCT GAA ACG ACC ATT ACC CAG AGC GGT TAT GGT AAC GGC GCC GAT
ser asp ala arg lys ser glu thr thr ile thr gln ser gly tyr gly asn gly ala asp 241/81                                   271/91
GTA GGC CAG GGT GCG GAT AAT AGT ACT ATT GAA CTG ACT CAG AAT GGT TTC AGA AAT AAT
val gly gln gly ala asp asn ser thr ile glu leu thr gln asn gly phe arg asn asn 301/101                                  331/111
GCC ACC ATC GAC CAG TGG AAC GCT AAA AAC TCC GAT ATT ACT GTC GGC CAA TAC GGC GGT
ala thr ile asp gln trp asn ala lys asn ser asp ile thr val gly gln tyr gly gly 361/121                                  391/131
AAT AAC GCC GCG CTG GTT AAT CAG ACC GCA TCT GAT TCC AGC GTA ATG GTG CGT CAG GTT
asn asn ala ala leu val asn gln thr ala ser asp ser ser val met val arg gln val 421/141                                  451/151
GGT TTT GGC AAC AAC GCC ACG GCT AAC CAG TAT TAA
gly phe gly asn asn ala thr ala asn gln tyr OCH
```

FIGURE 15

```
1/1                                10/30                                    20/60
ATG AAA CAT AAA TTA ATG ACC TCT ACT ATT GCG AGT CTG ATG TTT GTC GCT GGC GCA GCG
Met lys his lys leu met thr ser thr ile ala ser leu met phe val ala gly ala ala 30/90                                    40/120
GTT GCG GCT GAT CCT ACT CCG GTG AGC GTG AGT GGC GGT ACT ATT CAT TTC GAA GGT AAA
val ala ala asp pro thr pro val ser val ser gly gly thr ile his phe glu gly lys 50/150                                   60/180
CTG GTT AAT GCA GCC TGT GCC GTT AGC ACT AAA TCC GCC GAT CAA ACG GTG ACG CTG GGT
leu val asn ala ala cys ala val ser thr lys ser ala asp gln thr val thr leu gly 70/210                                   80/240
CAA TAC CGT ACC GCC AGC TTT ACG GCG ATT GGT AAT ACG ACT GCG CAG GTG CCT TTC TCC
gln tyr arg thr ala ser phe thr ala ile gly asn thr thr ala gln val pro phe ser 90/270                                   100/300
ATC GTC CTG AAT GAC TGC GAT CCG AAA GTG GCG GCC ACC GCT GCC GTG GCT TTC TCT GGT
ile val leu asn asp cys asp pro lys val ala ala thr ala ala val ala phe ser gly 110/330                                  120/360
CAG GCA GAT AAC ACC AAC CCT AAT TTG CTG GCT GTC TCC TCT GCG GAC AAT AGC ACC ACC
gln ala asp asn thr asn pro asn leu leu ala val ser ser ala asp asn ser thr thr 130/390                                  140/420
GCA ACC GGC GTC GGG ATT GAG ATT CTT GAT AAT ACC TCT TCA CCG TTG AAG CCG GAC GGC
ala thr gly val gly ile glu ile leu asp asn thr ser ser pro leu lys pro asp gly 150/450                                  160/480
GCG ACC TTC TCG GCG AAG CAG GCG CTG GTT GAA GGC ACC AAT ACG CTG CGT TTT ACC GCA
ala thr phe ser ala lys gln ala leu val glu gly thr asn thr leu arg phe thr ala 170/510                                  180/540
CGC TAT AAG GCA ACC GCC ACC GCC ACG ACG CCA GGC CAG GCT AAT GCC GAC GCC ACC TTT
arg tyr lys ala thr ala thr ala thr thr pro gly gln ala asn ala asp ala thr phe 185 // 558
ATC ATG AAA TAC GAA TAA
ile met lys tyr glu OCH
```

METHODS AND COMPOSITIONS COMPRISING THE AGFA GENE FOR DETECTION OF SALMONELLA

CROSS-REFERENCE TO RELATED APPLICATIONS

This application is a continuation-in-part of U.S. patent application Ser. No. 08/054,452, filed Apr. 26, 1993, abandoned.

TECHNICAL FIELD

The present invention relates generally to diagnostic tests and, more particularly, to nucleic acid based diagnostic tests, and antibody-based diagnostic tests directed to Salmonella.

BACKGROUND OF THE INVENTION

In 1980, the World Health Organization estimated that in developing countries food poisoning from infection with Salmonella bacteria (salmonellosis) contributed to more than 1 billion cases of acute diarrhea in children under the age of five years (Kvenberg and Archer, *Food Technol.* 40:77–98, 1987), and at least 5 million deaths (this reference, and all other references cited herein, is hereby expressly incorporated herein by reference in its entirety). Since the mid-1980s, the worldwide incidence of salmonellosis has increased steadily. *S. enteritidis*, in particular, has been implicated in the sharp increase in food borne infection since 1983. Indeed, the current frequency of *S. enteritidis* infections constitute a worldwide pandemic (Rodrique et al., *Epidemiol. Infect.* 105:21–27, 1990).

The severity of the disease is greatest in infants, the elderly, the infirm and in other persons with inadequate or impaired immune systems, including the malnourished. In third world countries where malnutrition is more commonly a complicating factor, mortality rates due to *S. enteritidis* infection as high as 28% have been reported. In both the clinical and industrial settings, the situation is also complicated by the fact that many people are asymptomatic carders. Salmonella spp., including *S. enteritidis*, often possess several plasmid encoded antibiotic resistance genes that complicate the treatment of human infections.

In the industrialized world, it is the contamination of food products by Salmonella bacteria that is most directly threatening to human health. Hence, it is not surprising that the increase in salmonellosis in first world countries parallels the centralization of food production and processing despite continued improvements in epidemiological and microbiological methods.

The significance of the problem is reflected in one aspect in the poultry-related industries. For example, in the U.S. alone hatcheries produce approximately 100 million broiler chicks per week and chicken egg production in the U.S. has reached 5 billion annually. A large proportion of *S. enteritidis* infections have been associated with the contamination of the contents of whole shell eggs resulting from vertical transmission of this pathogen from breeder stocks due to transovarian infection. This is significant since common procedures designed to decontaminate the external shell surface are not effective. The problem presented by *S. enteritidis* is exacerbated by the fact that infection in the adult laying hens may be asymptomatic. Typically, *S. enteritidis* infection of laying birds does not have a significant adverse effect on fertility, hatchability or egg production. Similarly, broiler chickens may be asymptomatic throughout their lifetime, although losses of about 20% do occur in infected flocks due to death in chicks, retardation of growth and rejection of contaminated birds at slaughtering. Contaminated poultry feed may be a major source of infection, but stress to poultry due to handling, transportation and overcrowding add to the problem by increasing the shedding of Salmonella from infected chickens. The end result is that the majority of modern processing plants, which process about 10,000 birds per hour, are contaminated and Salmonella are typically isolated from 40% to 70% of turkey or chicken carcasses sampled in the U.S. and Canada.

The overall economic costs of the rising incidence of food borne infections have been significant. The U.S. General Accounting Office has recently estimated the cost of *S. enteritidis* food poisoning in the U.S. between 1985 to 1990 at $118 million in lost productivity, medical and hospital costs resulting from about 9,500 illnesses. The U.S. Center for Disease Control receives more than 40,000 case reports annually but attributes greater than 2 million cases and roughly 2,000 deaths per year in the United States to salmonellosis (Cohen and Tauxe, *Science* 234:964–969, 1986). The economic cost related to treatment of salmonellosis in the U.S. was estimated to be $50 million in 1986. About 8 million cases involve physician consultation and an estimated 250,000 cases require hospitalization. Non-hospitalized cases are thought to have accounted for about $680 million in medical costs and minimally $2 billion in lost productivity. Others estimate the total costs of salmonellosis in the U.S. arising from medical treatment and lost productivity to be as high as $23 billion per year (Kvenberg and Archer, supra).

The losses absorbed by the food industry from liability and product loss are undoubtedly passed on to the consumer. Thus, there is a need for an effective risk-management program to monitor the different phases of poultry production including breeding, raising, slaughtering, packing and further processing, distribution and preparation, and consumption. The development of strategies for creating Salmonella-free feed, the control of Salmonella in breeder flocks, hatcheries, and product operations will include development of more effective diagnostics. Accordingly, there is a general need for a technology which could be applied to the inexpensive, rapid detection of all Salmonella food borne pathogens.

One type of assay for Salmonella comprises the standardized culture tests for Salmonella in the food industry. These culture assays are recognized by different names in different countries but they share the same basic approach. In the United States, the procedures are known as the "Bacteriological Analytical Manual" (BAM), published in 1984 by the Association of Official Analytical Chemists (AOAC, Arlington, Va.). In Canada, the procedures are known as the "Official Canadian Wet Culture Method" (WCM); the protocol most often used to test food samples is MFD-20.

Within the standardized tests, Samples are incubated at 30° C. to 37° C. for 18 to 24 hours in a rich, non-selective medium to promote recovery of the cells and allow them to begin to replicate to the levels detectable by current technologies. There will likely be an excess of other microorganisms in the sample, some of which may be from the closely related family Enterobacteriaceae. Therefore, a selective growth step is conducted to enrich for Salmonella bacteria, for example, by inoculating a small sample of the pre-enrichment culture into a selenite-cysteine broth, tetrathionite broth, or Rappaport-Vassiliadis broth for 18 to 24 hours, typically at an elevated temperature such as 43° C. The cells are then plated on a selective medium, such as brilliant green agar or xylose-lysine-deoxycholate agar, and incubated overnight. Presumptive colonies are then transferred to various biochemical or metabolic test media for confirmation. Pure cultures of Salmonella are then grown overnight on agar slopes for serotyping. In total, three to four days are required to obtain presumptive positive results, and a five to seven day wait can be necessary before final confirmation and identification of the Salmonella.

An alternative test to assay for the presence of Salmonella is based on nucleic acid probes. One such test uses probes constructed from a part of the fimA gene of *Salmonella typhimurium*, and is preferentially based on two particular sequences (Madonna and Woods, EP Publication No. 383, 509, Orthodiagnostic Systems, Raritan, N.J.). Briefly, a nucleic acid molecule of a known sequence is introduced to a sample under conditions suitable for hybridization of the nucleic acid molecule to its target nucleic acid sequence in the DNA or KNA of Salmonella. Alternative hybridization-based assays include the colormetric Gene-Trak® Salmonella Assay (Gene-Trak Systems, Framingham, Mass.), Fitts et al., *Appl. Environ. Microbiol.* 46:1146–1151, 1983.

Another alternative test is a fluorescent antibody assay (FA test Thomason, *J. Food Protection* 44:381–384, 1981), which includes the Salmonella Flouro-Kit (Incstar, Stillwater, Minn.). Such a test uses polyvalent antisera prepared against Salmonella flagella (anti-H) and lipopolysaccharide (LPS) O-chain (anti-O). The assay can also use purified polyclonal IgG antibodies. However, an FA test is laborious, has a high level of false-positive results, yields only presumptive positive samples, and requires visual determinations to be made by highly skilled personnel using expensive equipment.

Another test is an enzyme immunoassay (EIA). In general, as with the FA test described above, antibodies to flagella or lipopolysaccharide form the basis of most EIAs. EIAs can use either polyclonal or monoclonal antibodies. However, as with the FA test, false-positive results are a significant problem. Further, these assays can take an extensive testing period, and some diagnostic tests using monoclonal antibodies to Salmonella flagellin have reported significant problems with false-negative results. Examples of such EIAs include the TECRA Salmonella immunocapture ELISA manufactured by Bioenterprises Ply. Ltd., Roseville, NSW, Australia, and the Dynatech Laboratories, Inc. (Chantilly, Va.) Salmonella MICROELISA®-92 and MICROELISA®-32 Detection kit.

Still another type of test is an agglutination assay (Benge, *Eur. J. Clin. Microbiol. Infect. Dis.* 20 8:294–298, 1989), such as the Wellcollex-Colour Salmonella assay (Wellcome; Bouret and Jeanjean, *J. Clinical Microbiology* 30:2180–2186, 1992), which is based on anti-Salmonella antibodies conjugated to latex beads. This form of test is relatively simple, but requires at least two to three days to provide results from food or environmental samples, and has a relatively low level of sensitivity.

A further type of test is the selective motility assay, in which a sample potentially containing Salmonella is introduced into a pre-enrichment or selective growth medium in the first chamber of a double-chambered device. (Humbert et al., *Letters in Applied Microbiology* 10:245–249, 1990) The motile Salmonella then favorably grow and move across the pre-enrichment growth medium, entering the second chamber, which contains a semi-solid medium having a sample of antisera at the far end. As the motile Salmonella replicate and migrate into and across the second chamber, the antisera diffuses toward the oncoming bacteria, forming an immunoprecipitate line at the point where the bacteria contact the antisera.

Yet another test is a bacteriophage assay, such as the Vitek System's Salmonella test (McDonnell-Douglas Health Systems Co.). This assay uses bacteriophage that specifically recognize receptors on Salmonella. An enzyme is conjugated to the bacteriophage and is used for detection purposes. This test requires a minimum of 48 hours and is subject to false positive and false negative results.

Yet another test is an enzyme-linked amperometric immunosensor, a type of biosensor format (Brooks et al., *Journal of Applied Bacteriology* 73: 189–196, 1992).

Accordingly, the present invention discloses compositions and methods suitable for the diagnosis of Salmonella in a sample, including isolated nucleic acid molecules, isolated proteins, probes and primers.

SUMMARY OF THE INVENTION

In one aspect, the present invention provides an isolated nucleic acid molecule comprising a $sefU_2U_1BCD$ gene cluster, which is included in the $sefU_2U_1ABCD$ gene cluster. In an alternative embodiment, the isolated nucleic acid molecule comprises a sefABCD gene cluster or a $sefU_2U_1$ gene cluster. In further alternative embodiments, the present invention provides isolated nucleic acid molecules comprising a sefA gene, a sefB gene, a sefC gene, a sefD gene, a $sefU_1$ gene, or a $sefU_2$ gene.

The present invention also provides an isolated nucleic acid molecule comprising an agfA gene.

Still further, the present invention provides an isolated nucleic acid molecule comprising a tctCBA gene cluster. In alternative embodiments, the present invention provides isolated nucleic acid molecules comprising a tctA gene, tctB gene or tctC gene.

Preferably, the isolated nucleic acid molecules are recombinant, which means that the molecule has been constructed using recombinant nucleic acid techniques and includes nucleic acid sequences attached to the gene that are not naturally attached to, or in some cases proximate to, the gene.

In another aspect, the present invention provides probes based on one or more of the sefA, sefB, sefC, sefD, $sefU_1$, $sefU_2$, agfA, tctA, tctB, or tctC genes. In particular, these probes comprise at least a portion of the nucleotide sequence depicted in FIGS. 2A–2D from nucleotide No. 136 to nucleotide No. 633 (SEQ ID No. 39); FIGS. 2A–2D from nucleic acid No. 755, to nucleic acid No. 1495 (SEQ ID No. 39); FIGS. 2A–2D from nucleic acid No. 1512 to nucleic acid No. 3956 (SEQ ID No. 39); FIGS. 2A–2D from nucleic acid No. 3953, to nucleic acid No. 4402 (SEQ ID No. 39); FIGS. 3A–3B from nucleic acid No. 551 to nucleic acid No. 1120 (SEQ ID No. 44), and from nucleic acid No. 1027 to nucleic acid No. 452 (SEQ ID No. 46); FIGS. 4A–4B from nucleic acid No. 3323 to nucleic acid No. 4420 (SEQ ID No. 48); FIG. 5 from nucleic acid No. 2727, to nucleic acid No. 3236 (SEQ ID No. 52); FIGS. 6A–6B from nucleic acid No. 1293 to nucleic acid No. 2270 (SEQ ID No. 54); or, FIG. 7A from nucleic acid No. 1, to nucleic acid No. 361 (SEQ ID No. 56); FIG. 7B from nucleic add No. 1 to nucleic acid No. 451 SEQ ID No. 58.

In one embodiment, the probes comprise one or more of the sefA gene, the sefB gene, the sefC gene, the $sefU_1$ gene and the $sefU_2$ gene, and the probes are capable of specifically hybridizing to *S. enteritidis*, *S. berta*, *S. pullorum*, *S. dublin* and *S. gallinarum* under conditions of high stringency.

In another aspect, the present invention provides vector constructs comprising a $sefU_2U_1BCD$ gene cluster. In an alternative embodiment, the vector construct comprises a sefABCD gene cluster. In still further alternative embodiments, the vector construct comprises a sefA gene, a sefB gene, a sefC gene, a sefD gene, a sefU$_1$ gene or a sefU$_2$ gene. The present invention also provides a vector construct comprising an agfA gene. The present invention further provides a vector construct comprising the tctCBA gene cluster. In alternative embodiments, the vector construct comprises a tctA gene, a tctB gene or a tctC gene.

In preferred embodiments, the vector construct of the invention comprises an expression vector. Even further preferably, the expression vector is able to express the gene or gene cluster upon introduction of the expression vector into a cell of a living organism, further preferably a plant or on which in some embodiments is animal. The host cell for the expression vector construct is preferably *E. coli*, a Salmonella, a Shigella spp., Citrobacter, Enterobacteria, Pseudomonas, Streptomyces, Bacillus, *Staphylococcus aureus*, further preferably an *E. coli* or a Salmonella.

In a further aspect, present invention provides a probe comprising at least a portion of the nucleotide sequence shown in FIG. 7A, from nucleic acid No. 1 to nucleic acid No. 361, or FIG. 7B from nucleic acid No. 1 to nucleic acid No. 451, the probe capable of specifically hybridizing to the DNA of GVVPQ-fimbriae (SEQ ID No. 1) encoding enteropathogenic bacteria of the family Enterobacteriaceae under conditions of moderate stringency. Conditions of moderate stringency are such that a mismatch of a single base pair or similar small number of base pairs does not prevent hybridization, yet only nucleic acids encoding a GVVPQ-type fimbrin amino acid sequence are able to hybridize to the probe.

In still a further aspect, the present invention provides probes capable of specifically hybridizing to a nucleic acid molecule from greater than 99% of Salmonella strains that are pathogenic to warm-blooded animals relative to nucleic acid molecules from other, preferably virtually all, microorganisms. It is particularly preferred that the probes be able to distinguish such strains from all other microorganisms. In a preferred embodiment, the probes are able to specifically hybridize to greater than 99.5% of such Salmonella strains.

In yet a further aspect, the present invention provides a primer suitable for a nucleic acid amplification procedure wherein the primer is able to specifically hybridize to a nucleic acid molecule from greater than 99% of Salmonella strains that are pathogenic to warm-blooded animals relative to nucleic acid molecules from virtually all other microbial organisms. In a preferred embodiment, the primer is able to specifically hybridize to greater than 99.5% of such Salmonella strains. In a preferred embodiment, the primer is one of a set of two primers that are able to hybridize to opposing strands of a target sequence, such that the set is suitable for use in the PCR reaction.

In yet a further aspect, the present invention provides a method for detecting the presence of Salmonella in a sample comprising treating cells contained within the sample to expose the cellular nucleic acids, then incubating the cellular nucleic acids with one or more of the probes, preferably labeled, described above under conditions suitable for desired hybridization, and then detecting the presence of the hybridized labeled probe. In a preferred embodiment, the exposed cellular nucleic acid is subjected to an amplification procedure, such as PCR or LCR, prior to incubation with the labeled probe to give a hybridized labeled probe or a product build up that is detected spectrophotometrically.

In a further aspect, the present invention provides a method for detecting the presence of antibodies to Salmonella that are in a sample. The sample is contacted with TctC protein that is bound to a solid phase, preferably composed of styrene, under conditions suitable for the antibodies in the sample to bind to the protein and then the antibodies are detected. In alternative embodiments, the protein is a SefA protein, a SefC protein, or an Agfa protein, a FimA protein or a SefD protein, or a fimbrial or aggregative structure incorporating such proteins, such as SEF14 (for SefA), SEF21 (for FimA), SEF17 (for AgfA) or SEF18 (for SefD). In a further alternative embodiment, the method is for detecting the presence of Salmonella in a sample, and comprises contacting the sample with a labeled antibody to SefD protein under conditions suitable for the antibody to bind to the SefD protein, and then detecting the presence of the bound labeled antibody. In another alternative embodiment, the antibodies are to a SefA protein, a SefC protein, an Agfa protein, a FimA protein, or a TctC protein.

In still another aspect, the present invention provides methods able to distinguish greater than 99% of the strains of Salmonella that are pathogenic to warm-blooded animals from virtually all other microbes in less than 24 hours. In these methods, cells from a sample are treated to expose cellular nucleic acids, then the cellular nucleic acids are incubated with one or more of the probes, preferably labeled, described above under conditions suitable for desired hybridization, and then the hybridized labeled probe is detected. In a preferred embodiment, the exposed cellular nucleic acids are amplified prior to the incubation with the labeled probe. In a further preferred embodiment, these methods are able to distinguish greater than 99.5% of the strains of Salmonella. In an alternative embodiment, the methods of the present invention provide for detecting the presence of GVVPQ (SEQ. ID No. 1) fimbria-encoding, or SefA-type, SefD-type or FimA-type fimbriae encoding, enteropathogenic bacteria of the family Enterobacteriaceae in a sample. In this method, cells within the sample are treated to expose cellular nucleic acids, the cellular nucleic acids are incubated with the labeled probe (as described above) under conditions suitable for hybridization, and then the hybridized labeled probe is detected. In a preferred embodiment, the exposed cellular nucleic acids are amplified prior to the incubation step.

In still yet another aspect, the present invention provides a method of detecting greater than 99.5% of Salmonella in a sample, preferably greater than 99.9% of Salmonella in a sample, and further preferably all of such Salmonella. The method comprises a nucleic acid probe assay, an antibody assay and/or a protein assay, as described above and set forth more fully below, wherein the method targets a group of the above genes, and/or utilizes a cocktail of the respective gene products, comprising the agfA gene, the fimA gene, and the tctC gene. Further, the group and/or cocktail may comprise a sefA gene.

These and other aspects of the present invention will become evident upon reference to the following detailed description and attached drawings. In addition, various references are set forth below which describe in more detail certain procedures or compositions (e.g., plasmids, etc.); such references are incorporated by reference in their entirety.

BRIEF DESCRIPTION OF THE DRAWINGS

FIGS. 2A–2D depicts the nucleotide sequences of sefA, sefB, sefC and sefD (SEQ ID No. 39), and the corresponding predicted amino acid sequences (SEQ ID Nos. 40, 41, 42 and 43 respectively).

FIGS. 3A–3B depicts the nucleotide sequences of sefU$_1$ and sefU$_2$ (SEQ ID Nos. 44 and 46 respectively) and the corresponding predicted amino acid sequences (SEQ ID Nos. 45 and 47 respectively).

FIGS. 4A–4B depicts the nucleotide sequence of tctA (SEQ ID No. 48) and the corresponding predicted amino acid sequence (SEQ ID Nos. 49, 50 and 51).

FIG. 5 depicts the nucleotide sequence of tctB (SEQ ID No. 52) and the corresponding predicted amino acid sequence (SEQ ID No. 53).

FIGS. 6A–6B depicts the nucleotide sequence of tctC (SEQ ID No. 54) and the corresponding predicted amino acid sequence (SEQ ID No. 55).

FIG. 7A depicts the nucleotide sequence of an agfA gene fragment (SEQ ID No. 56) amplified from *S. enteritidis* 27655-3b TnphoA mutant strain and cloned into pUC19, and the corresponding predicted amino acid sequence (SEQ ID No. 57). The solid arrows indicate PCR primer pairs TAF3 and TAF4; the dashed arrows indicate TAF5 and TAF6.

FIG. 7B depicts the sequence of the full agfA gene (SEQ ID No. 58) of *S. enteritidis* 27655-3b and the corresponding predicted amino acid sequence (SEQ ID No. 59).

FIG. 15 depicts the nucleotide sequence of fimA of *S. enteritidis* SEQ ID No. 60, and the corresponding predicted amino acid sequence SEQ ID No. 61.

DETAILED DESCRIPTION OF THE INVENTION

Figure 1:
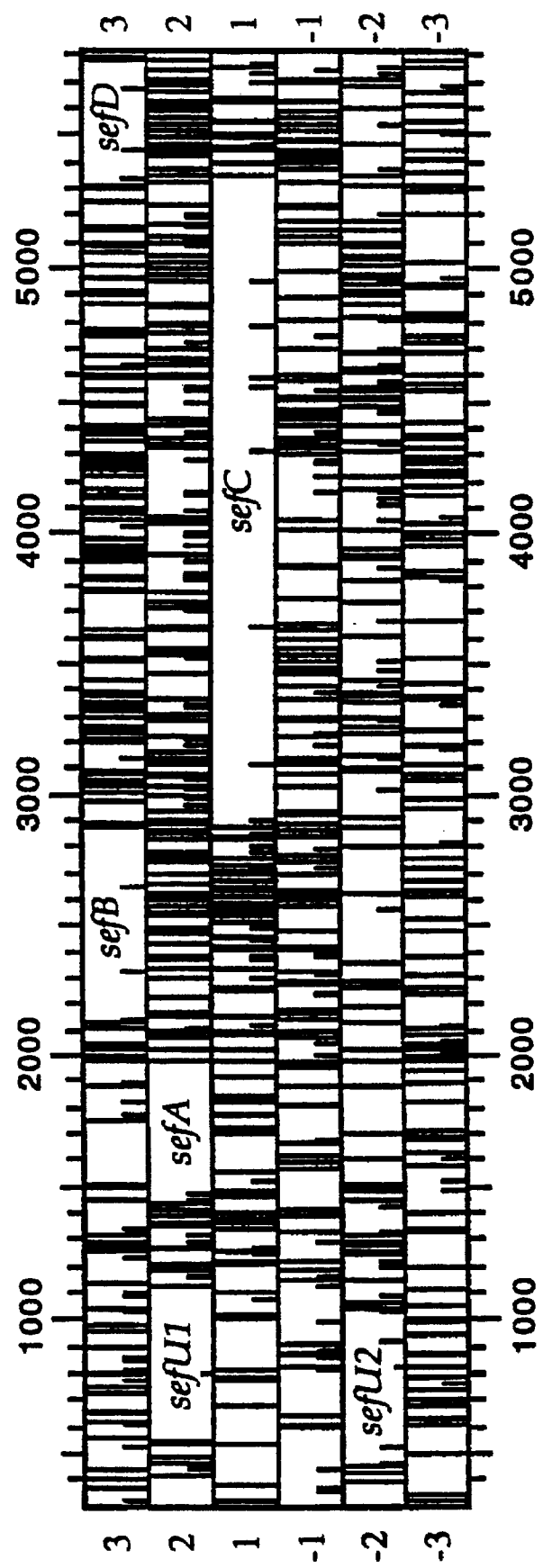
FIG. 1 is a schematic illustration and open reading frame analysis of the sefU$_2$ U$_1$ABCD gene cluster.

The present invention provides methods and compositions for the detection of Salmonella. These methods and compositions include numerous isolated genes specific to Salmonella, vector constructs, numerous isolated proteins specific to Salmonella and diagnostic tests. These methods and compositions are described further below.

I. Genes Specific to Salmonella

A. Genes Generally

The present invention provides isolated DNA molecules comprising the sef$U_2U_1$ABCD gene cluster, the sefABC gene cluster, the sef$U_2U_1$ gene cluster, the sefA gene, sefB gene, sefC gene, the sefD gene, the sef$U_1$ gene, the sef$U_2$ gene, the agfA gene, the fimA gene, the tctCBA gene cluster, the tctA gene, the tctB gene, and/or the tctC gene. Although one embodiment of each of these molecules is shown in FIGS. 2 to 7, it should be understood that within the context of the present invention, reference to one or more of these genes includes derivatives of the genes that are substantially similar to the genes (and, where appropriate, the protein (including peptides and polypeptides) that are encoded by the genes and their derivatives). As used herein, a nucleotide sequence is deemed to be "substantially similar" if: (a) the DNA sequence is derived from the coding region of a native gene of any Salmonella serovar and maintains substantially the same biological activity (including, for example, portions of the sequence or allelic variations of the sequences discussed above); (b) the DNA sequence is capable of hybridization to DNA sequences of the present invention under moderate, high or very high stringency (see Sambrook et al., *Molecular Cloning: A Laboratory Manual,* 2nd ed., Cold Spring Harbor Laboratory Press, New York, 1989); or (c) the DNA sequences are degenerate as a result of the genetic code to the DNA sequences defined in (a) or (b). Within the context of the present invention, moderate stringency means conditions such that an appropriate nucleotide sequence is able to selectively hybridize to nucleotide sequences from Salmonella and to conserved nucleotide sequences in other bacteria such as *E. coli*. High stringency means the nucleotide sequence is able to selectively hybridize to nucleotide sequences from Salmonella. Very high stringency means the nucleotide sequence is able to selectively hybridize to a single Salmonella species, such as *S. enteritidis, S. dublin* or *S. gallinarum.*

B. sef$U_1$, sef$U_2$, sefB, sefC, sefD genes and the sef$U_2U_1$BCD gene cluster In one aspect, the present invention provides the nucleotide sequences of the sef$U_1$, sef$U_2$, sefA, sefB, sefC, and sefD genes, which are located in a single cluster, the sef$U_2U_1$ABCD gene cluster. As can be seen by reference to FIG. 1, which is a schematic illustration and open reading frame analysis of the sef$U_2U_1$ABCD gene cluster, the sefB and sefC genes comprise an approximately 3.4 kilobase pair region of Salmonella DNA. In vitro expression directed by a 5.3 kilobase pair DNA fragment encompassing sefA, sefB and sefC indicated that the SefB and SefC proteins have an approximately 14K, 28K and 90K $M_r$ molecular weight, respectively. See FIG. 11A. The present invention preferably involves one or more of a sefA, sefB, sefC, sefD, sef$U_1$, or sef$U_2$ gene. Further information with respect to the sefA gene and its products may be found in U.S. application Ser. No. 08/054,542 abandoned. As noted above, these applications and all other references cited herein are expressly incorporated by reference herein in their entirety.)

Experimental results with *S. enteritidis* indicate that sefB and sefC are not expressed in the absence of sefA. Primer extension analysis of sefABC gene clusters revealed two major transcription start sites located upstream of sefA (FIG. 12). Transcription of sefB and sefC is also initiated from the sefA promoter region. Secondary structure analysis of the mRNA transcript from sefABC predicted the formation of two stable stem-loop structures in the intercistronic region between sefA and sefB, which is indicative of differential regulation of sefA as opposed to sefB and sefC translation. The nucleotide sequences, and corresponding amino acid sequences, of sefB, sef$U_1$ and sef$U_2$ are depicted in FIGS. 2A–2D and 3A–3B.

sef$U_1$ and sef$U_2$ are overlapping open reading frames oriented in the opposite directions (i.e., encoded on opposite strands). sefD abuts sefC and a consensus Shine-Dalgarno ribosomal binding site sequence is just inside the sef$C_{orf}$. No promoter is recognized immediately upstream of sefD; expression may be directed by the sefA promoter.

C. agfA gene

The agfA gene codes for a structural fimbrin protein composing very thin fimbriae, approximately 3–4 nanometers in diameter, that are highly aggregative and stable. The aggregative property of the fimbriae is believed to be due to its hydrophobicity. The gene product of the agfA gene, AgfA, is found in SEF17 fimbriae, and comprises an approximately 14–15K$M_r$ molecular weight protein. AgfA contributes to heavy pellicle formation in static cultures, colony hydrophobicity, and autoaggregation of cells in culture. SEF17 fimbriae are immunologically distinct from SEF14 and SEF21, as indicated by the lack of cross-reactivity with polyclonal antisera raised in rabbits against SEF14 or SEF21 (Collinson et al., Purification and characterization of thin, aggregative fimbriae from *S. enteritidis,*" *J. Bacteriol.* 173:4773–4781, 1991). FIG. 7A depicts the nucleotide sequence of an agfA gene fragment that was amplified from the *S. enteritidis* 27655-3b TnphoA mutant strain and then cloned into pUG 19. The bases underlined in the agfA sequence of FIG. 7A are common to portions of the PCR primers TAF1 and TAF2, which were used in amplification of this fragment. Below the agfA sequence in FIG. 7A is the translated amino acid sequence. As discussed further below, the nucleotide sequences targeted by the diagnostic PCR primer pairs TAF3 and TAF4 (solid arrows) and TAF5 and TAF6 (dashed arrows) are also indicated in FIGS. 3A–3B.

The sequence of the full agfA gene of *S. enteritidis* 3b is shown in FIG. 7B. The sequence depicted in FIG. 7B reflects two nucleotide changes (at positions 69 and 75 of FIG. 7B) from the sequence of FIG. 7A, but the changes do not alter the encoded amino acid sequence.

D. tctA, tactB, and tctC genes, and the tctI, tctII and tctIII operons

The tctA, tctB, tctC and tctD genes are located in the tctI operon, which is one of three operons for tricarboxylic acid transport within Salmonella spp. The other Salmonella tricarboxylic acid transport systems are termed tctII and tctIII. It is believed that the tricarboxylic acid transport system of Salmonella is lacking from certain other related genera. tctI and tctIII both encode proteins responsible for citrate transport and are induced by growth of *Salmonella typhimurium* on minimal media supplemented with citrate as a carbon source. tctII is normally not expressed. Each system demonstrates preferential transport of various tricarboxylic acids and different concentrations of the monovalent cations $Na^+$ and $K^+$. The transport of tricarboxylic acids, particularly citrate, are important to the intracellular survival of Salmonella, as such transport provides a means of scavenging nutrients from a host cell. Accordingly, mutants in these various tct systems, preferably in *S. typhimurium* or *S. enteritidis*, create attenuated strains of Salmonella capable of being taken into a host cell, and capable of persisting for a limited time, yet not able to proliferate within such a host cell. In a preferred embodiment, one or more of these tct mutants are coupled with a mutant unable to utilize succinate to provide a "back-up" system to assure attenuation.

The nucleotide sequences for tctA, tctB and tctC, along with their corresponding amino acids, are depicted in FIGS. 4A–4B, 5 and 6A–6B, respectively.

E. fimA gene fimA encodes the Salmonella type1 fimbriae, which is also known in *Salmonella enteritidis* as SEF21 fimbriae. Prior to the disclosure of the subject application, Type 1 fimbriae were believed to be the only Salmonella fimbrial type implicated in pathogenicity. polyclonal antisera studies have indicated that Type 1 fimbrial antigens are among the majority of Salmonella serotypes. The sequence of the fimA gene of *S. enteritidis* 3b is shown in FIG. 15.

II. Vector Constructs Comprising the Gene Sequences of the Present Invention

A. Vector Constructs Generally

The present invention provides for the manipulation and expression of the above described genes by culturing host cells containing a construct capable of expressing the above-described genes, including substantially similar derivatives thereof.

Numerous vector constructs, including all or part of the nucleotide sequences of a native or derivative sefU$_1$, sefU$_2$, sefA, sefB, sefC, sefD, agfA, tctA, tctB, and/or tctC genes, as described above, can be prepared as a matter of convenience. Within the context of the present invention, a DNA construct is understood to refer to a DNA molecule, or a clone of such a molecule (either single-stranded or double-stranded), that has been modified through human intervention to contain segments of DNA combined and juxtaposed in a manner that as a whole would not otherwise exist in nature. Vector constructs of the present invention comprise a first DNA segment encoding one or more of the sefU$_1$, sefU$_2$, sefA, sefB, sefC, sefD, agfA, tctA, tctB, and/or tctC genes operably linked to additional DNA segments required for the expression of the first DNA segment. Within the context of the present invention, additional DNA segments will include a promoter and will generally include transcription terminators, and may further include enhancers and other elements.

Mutations in nucleotide sequences constructed for expression of variant proteins preferably preserve the reading frame of the coding sequences. Furthermore, the mutations will preferably not create complementary regions that could hybridize to produce secondary mRNA structures, such as loops or hairpins, that would adversely affect translation of the mRNA. Although a mutation site may be predetermined, it is not necessary that the nature of the mutation per se be predetermined. For example, in order to select for optimum characteristics of routants at a given site, random mutagenesis may be conducted at the target codon and the expressed mutants screened for indicative biological activity.

Mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); and Sambrook et al. (supra).

The primary amino acid structure of the above described proteins may also be modified by forming covalent or aggregative conjugates with other chemical moieties, such as glycosyl groups, lipids, phosphate, acetyl groups, or with other proteins or polypeptides.

Within a further embodiment, the above described proteins may be fused with other peptides that facilitate purification or identification of these proteins. For example, a protein can be prepared as a fusion protein with the FLAG polypeptide sequence (see U.S. Pat. No. 4,851,341; see also Hopp et al., *Bio/Technology* 6:1204, 1988). The FLAG polypeptide sequence is highly antigenie and provides an epitope for binding by a specific monoclonal antibody, enabling rapid purification of the expressed recombinant protein. This sequence is also specifically cleaved by bovine mucosal enterokinase at the residue immediately following the Asp-Lys pairing.

B. Expression Vectors

One type of vector construct, known as an expression vector, can contain DNA segments necessary to direct the secretion of a polypeptide of interest. Such DNA segments can include at least one secretory signal sequence. Preferred secretory signals include the yeast alpha factor signal sequence (pre-pro sequence; Kurjan and Herskowitz, *Cell* 30:933–943, 1982; Kurjan et al., U.S. Pat. No. 4,546,082; Brake, EP 116,201), the Pho5 signal sequence (Beck et al., WO 86/00637), the Suc2 signal sequence (Carlson et al., *Mol. Cell. Biol.* 3:439–447, 1983), the α-2 plasmin inhibitor signal sequence (Tone et al., *J. Biochem.* (Tokyo) 102:1033–1042, 1987), the tissue plasminogen activator signal sequence (Pennica et al., *Nature* 301:214–221, 1983), the *E. coli* PhoA signal sequence (Yuan et al., *J. Biol. Chem.* 265:13528–13552, 1990), or any of the other bacterial signal sequences known in the art, such as those reviewed by Oliver (*Ann. Rev. Microbiol.* 39:615–649, 1985). Alternatively, a secretory signal sequence can be synthesized according to the rules established, for example, by von Heinje (*Eur. J. Biochem.* 133:17–21, 1983; *J. Mol. Biol.* 184:99–105, 1985; *Nuc. Acids Res.* 14:4683–4690, 1986). Secretory signal sequences can be used singly or in combination.

For expression, a DNA molecule as described above is inserted into a suitable vector construct, which in turn is used to transform or transfect appropriate host cells for expression. Host cells suitable for use in practicing the present invention include mammalian, avian, plant, insect, bacterial and fungal cells. Preferred eukaryotic cells include cultured mammalian cell lines (e.g., rodent or human cell fines) and fungal cells, including species of yeast (e.g., Saccharomyces spp., particularly *S. cerevisiae*, Schizosaccharomyces spp., or Kluyveromyces spp.) or filamentous fungi (e.g., Aspergillus spp., Neurospora spp.). Strains of the yeast *Saccharomyces cerevisiae* are particularly preferred. Methods for producing recombinant proteins in a variety of prokaryotic and eukaryotic host cells are generally known in the art (see, "Gene Expression Technology," *Methods in Enzymology*, Vol. 185, Goeddel (ed.), Academic Press, San Diego, Calif., 1990; see also, "Guide to Yeast Genetics and Molecular Biology," *Methods in Enzymology*, Guthrie and Fink (eds.), Academic Press, San Diego, Calif., 1991). In general, a host cell will be selected on the basis of its ability to produce the protein of interest at a high level or its ability to carry out at least some of the processing steps necessary for the biological activity of the protein. In this way, the number of cloned DNA sequences that must be introduced into the host cell can be minimized and overall yield of biologically active protein can be maximized.

Suitable yeast vectors for use in the present invention include YRp7 (Struhl et al., *Proc. Natl. Acad Sci. USA* 76:1035–1039, 1978), YEp13 (Broach et al., *Gene* 8:121–133, 1979), pJDB249 and pJDB219 (Beggs, *Nature* 275:104–108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include leu2 (Broach et al., ibid), ura3 (Botstein et al., *Gene* 8:17, 1979), or his3 (Struhl et al., ibid). Another suitable selectable marker is the cat gene, which confers chloramphenicol resistance on yeast cells.

Preferred promoters for use in yeast include promoters from yeast glycolytic genes (Hitzeman et al., *J. Biol. Chem.* 255:12073–12080, 1980; Alber and Kawasaki, *J. Mol. Appl. Genet.* 1:419–434, 1982) or alcohol dehydrogenase genes (Young et al., in *Genetic Engineering of Microorganisms for Chemicals*, Hollaender et al. (eds.), p. 355, Plenum, N.Y., 1982; Ammerer, *Meth. Enzymol.* 101:192–201, 1983). The expression units may also include a transcriptional terminator.

In addition to yeast, proteins of the present invention can be expressed in filamentous fungi, for example, strains of the fungi Aspergillus (McKnight et al., U.S. Pat. No. 4,935,349, which is incorporated herein by reference). Examples of useful promoters include those derived from *Aspergillus nidulans* glycolytic genes, such as the adh3 promoter (McKnight et al., *EMBO J.* 4:2093–2099, 1985). An example of a suitable terminator is the adh3 terminator (McKnight et al., ibid., 1985). The expression units utilizing such components are cloned into vectors that are capable of insertion into the chromosomal DNA of Aspergillus.

Techniques for transforming fungi are well known in the literature, and have been described, for instance, by Beggs (ibid.), Hinnen et al. (*Proc. Natl. Acad. Sci. USA* 75:1929–1933, 1978), Yelton et al. (*Proc. Natl. Acad Sci. USA* 81:1740–1747, 1984), and Russell (*Nature* 301:167–169, 1983). The genotype of the host cell will generally contain a genetic defect that is complemented by the selectable marker present on the expression vector. Choice of a particular host and selectable marker is well within the level of ordinary skill in the art.

In addition to fungal cells, cultured mammalian cells may be used as host cells within the present invention. Preferred cultured mammalian cells for use in the present invention include the COS-1 (ATCC No. CRL 1650), COS-7 (ATCC No. CRL 1651), BHK (ATCC No. CRL 1632), and 293 (ATCC No. CRL 1573; Graham et al., *J. Gen. Virol.* 36:59–72, 1977) cell lines. A preferred BHK cell line is the BHK 570 cell line (deposited with the American Type Culture Collection under accession number CRL 10314). In addition, a number of other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1), SP2/0-Ag14 (ATCC No. 1581), HIT-T15 (ATCC No. CRL 1777), and RINm 5AHT$_2$B (Orskov and Nielson, *FEBS* 229(1):175–178, 1988).

Mammalian expression vectors for use in carrying out the present invention will include a promoter capable of directing the transcription of a cloned gene or cDNA. Preferred promoters include viral promoters and cellular promoters. Viral promoters include the immediate early cytomegalovirus promoter (Boshart et al., *Cell* 41:521–530, 1985) and the SV40 promoter (Subramani et al., *Mol. Cell. Biol.* 1:854–864, 1981). Cellular promoters include the mouse metallothionein-1 promoter (Palmiter et al., U.S. Pat. No. 4,579,821), a mouse $V_j$ promoter (Bergman et al., *Proc. Natl. Acad. Sci. USA* 81:7041–7045, 1983; Grant et al., *Nuc. Acids Res.* 15:5496, 1987) and a mouse $V_H$ promoter (Loh et al., *Cell* 33:85–93, 1983). Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer and the mouse 1 enhancer (Gillies, *Cell* 33:717–728, 1983). Expression vectors may also include sequences encoding the adenovirus VA RNAs. Suitable expression vectors can be obtained from commercial sources (e.g., Stratagene, La Jolla, Calif.).

Vector constructs comprising cloned DNA sequences can be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), or DEAE-dextran mediated transfection (Ausubel et al. (eds.), *Current Protocols in Molecular Biology*, John Wiley and Sons, Inc., New York, 1987), which are incorporated herein by reference. To identify cells that have stably integrated the cloned DNA, a selectable marker is generally introduced into the cells along with the gene or cDNA of interest. Preferred selectable markers for use in cultured mammalian cells include genes that coffer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass., which is incorporated herein by reference). The choice of selectable markers is well within the level of ordinary skill in the art.

As discussed further below, naked vector constructs can also be taken up by muscular cells subsequent to injection into the muscle of a mammal (or other animals).

Selectable markers may be introduced into the cell on a separate vector at the same time as the $sefU_1$, $sefU_2$, sefA, sefB, sefC, sefD, agfA, tctA, tctB, and/or tctC genes sequences, or they may be introduced on the same vector. If on the same vector, the selectable marker and the $sefU_1$, $sefU_2$, sefA, sefB, sefC, sefD, agfA, tctA, tctB, and/or tctC genes sequences may be under the control of different promoters or the same promoter, the latter arrangement producing a dicistronic message. Constructs of this type are known in the art (for example, Levinson and Simonsen, U.S.

Pat. No. 4,713,339). It can also be advantageous to add additional DNA, known as "carrier DNA," to the mixture that is introduced into the cells.

Mammalian cells containing a suitable vector are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable, selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production.

Numerous plant host cells known in the art can also be useful within the present invention, in light of the subject specification.

The preferred prokaryotic host cell for use in expressing the gene sequences of the present invention is Salmonella. Other preferred host cells include strains of the bacteria E. coli, although Bacillus, Shigella, Pseudomonas, Streptomyces and other genera are also useful. Techniques for transforming these hosts and expressing foreign DNA sequences cloned therein are well known in the art (see, e.g., Maniatis et ed., *Molecular Cloning: A Laboratory Manual*, Cold Spring Harbor Laboratory, 1982, which is incorporated herein by reference; or Sambrook et al., supra). Vectors used for expressing cloned DNA sequences in bacterial hosts will generally contain a selectable marker, such as a gene for antibiotic resistance, and a promoter that functions in the host cell. Appropriate promoters include the trp (Nichols and Yanofsky, *Meth. Enzymol.* 101:155–164, 1983), lac (Casadaban et al., *J. Bacteriol.* 143:971–980, 1980), and phage λ (Queen, *J. Mol. Appl. Genet.* 2:1–10, 1983) promoter systems. Plasmids useful for transforming bacteria include the pUG plasmids (Messing, *Meth. Enzymol.* 101:20–78, 1983; Vieira and Messing, *Gene* 19:259–268, 1982), pBR322 (Bolivar et al., *Gene* 2:95–113, 1977), pCQV2 (Queen, ibid.), and derivatives thereof. Plasmids may contain both viral and bacterial elements.

Given the teachings provided herein, promoters, terminators and methods for introducing expression vectors encoding $sefU_1$, $sefU_2$, sefA, sefB, sefC, sefD, agfA, tctA, tctB, and/or tctC genes of the present invention into plant, avian, fish, and insect cells would be evident to those of skill in the art. The use of baculoviruses, for example, as vectors for expressing heterologous DNA sequences in insect cells has been reviewed by Atkinson et al. (*Pestic. Sci.* 28:215–224, 1990). In addition, the use of *Agrobacterium rhizogenes* as vectors for expressing genes in plant cells has been reviewed by Sinkar et ed., (*J. Biosci.* (Bangalore) 11:47–58, 1987).

Host cells containing vector constructs of the present invention are then cultured to express a DNA molecule as described above. The cells are cultured according to standard methods in a culture medium containing nutrients required for growth of the chosen host cells. A variety of suitable media are known in the art and generally include a carbon source, a nitrogen source, essential amino acids, vitamins and minerals, as well as other components, e.g., growth factors or serum, that may be required by the particular host cells. The growth medium will generally select for cells containing the DNA construct(s) by, for example, drug selection or deficiency in an essential nutrient which is complemented by the selectable marker on the DNA construct or co-transfected with the DNA construct.

Suitable growth conditions for yeast cells, for example, include culturing in a chemically defined medium, comprising a nitrogen source, which may be a non-amino acid nitrogen source or a yeast extract, inorganic salts, vitamins and essential amino acid supplements at a temperature between 4° C. and 37° C., with 30° C. being particularly preferred. The pH of the medium is preferably maintained at a pH greater than 2 and less than 8, more preferably pH 5–6. Methods for maintaining a stable pH include buffering and constant pH control. Preferred agents for pH control include sodium hydroxide. Preferred buffering agents include succinic acid and Bis-Tris (Sigma Chemical Co., St. Louis, Mo.). Due to the tendency of yeast host cells to hyperglycosylate heterologous proteins, it may be preferable to express the sef$U_1$, sef$U_2$, sefA, sefB, sefC, sefD, agfA, tctA, tctB, and/or tctC genes of the present invention in yeast cells having a defect in a gene required for asparagine-linked glycosylation. Such cells are preferably grown in a medium containing an osmotic stabilizer. A preferred osmotic stabilizer is sorbitol supplemented into the medium at a concentration between 0.1M and 1.5M, preferably at 0.5M or 1.0M.

Cultured mammalian cells are generally cultured in commercially available serum-containing or serum-free media. Selection of a medium and growth conditions appropriate for the particular cell line used is well within the level of ordinary skill in the art.

III. Proteins

A. Proteins Generally

As noted above, the present invention also provides isolated proteins. Within the context of the present invention, such proteins are understood to include the whole, or portions, of a gene product derived from one or more of the sef$U_1$, sef$U_2$, sefA, sefB, sefC, sefD, agfA, fimA, tctA, tctB, and/or tctC genes, or derivatives thereof as discussed above. Where the protein is a portion of a native gene or is encoded by derivative of a native gene, the protein maintains substantially the same biological activity of the native protein. The structure of the proteins corresponding to the sef$U_1$, sef$U_2$, sefA, sefB, sefC, sefD, agfA,fimA, tctA, tctB, and/or tctC genes can be predicted from the primary translation products using the hydrophobicity plot function of, for example, P/C Gene or Intelligenetics Suite (Intelligenetics, Mountain View, Calif.), or according to the methods described by Kyte and Doolittle (*J. Mol. Biol.* 157:105–132, 1982).

B. Purification of Proteins

Proteins can be isolated by, among other methods, culturing suitable host and vector systems to produce the recombinant translation products of the present invention. Supernatants from such cell lines, or protein inclusions or whole cells where the protein is not excreted into the supernatant, can then be treated by a variety of purification procedures in order to isolate the desired proteins. For example, the supernatant may be first concentrated using commercially available protein concentration filters, such as an Amicon or Millipore Pellicon ultrafiltration unit. Following concentration, the concentrate may be applied to a suitable purification matrix such as, for example, an anti-protein antibody bound to a suitable support. Alternatively, anion or cation exchange resins may be employed in order to purify the protein. As a further alternative, one or more reverse-phase high performance liquid chromatography (RP-HPLC) steps may be employed to further purify the protein. Other methods of isolating the proteins of the present invention are well known in the skill of the art.

A protein is deemed to be "isolated" within the context of the present invention if no other (undesired) protein is detected pursuant to SDS-PAGE analysis followed by Coomassie blue staining. Within other embodiments, the desired protein can be isolated such that no other (undesired) protein is detected pursuant to SDS-PAGE analysis followed by silver staining.

C. Preparation of Antibodies

In another aspect, the proteins of the present invention are utilized to prepare specifically binding antibodies. Accordingly, the present invention also provides such antibodies. Within the context of the present invention, the term "antibodies" includes polyclonal antibodies, monoclonal antibodies, anti-idiotypic antibodies, fragments thereof such as F(ab')$_2$ and Fab fragments, and recombinantly produced binding partners. Such binding partners incorporate the variable regions that permit a monoclonal antibody to specifically bind, which means an antibody able to selectively bind to a peptide produced from one of the sefU$_1$, sefU$_2$, sefA, sefB, sefC, sefD, agfA, fimA tctA, tctB, and/or tctC genes of the invention. The affinity of a monoclonal antibody or binding partner can be readily determined by one of ordinary skill in the art (see Scatchard, *Ann. N.Y. Acad Sci.* 51:660–672, 1949).

A variety of assays can be utilized in order to detect antibodies that specifically bind to the desired protein or peptide. Exemplary assays are described in detail in *Antibodies: A Laboratory Manual*, Harlow and Lane (eds.), Cold Spring Harbor Laboratory Press, 1988. Representative examples of such assays include: countercurrent immunoelectrophoresis (CIEP), radioimmunoassays, radioimmunoprecipitations, enzyme-linked immunosorbent assays (ELISA), dot blot assays, inhibition or competition assays, and sandwich assays, immunostick (dipstick) assays, simultaneous immunoassays, immunochromatographic assays, immunofiltration assays, latex bead agglutination assays, immunofluorescent assays, biosensor assays, and low-light detection assays (see U.S. Pat. Nos. 4,376,110 and 4,486,530; see also *Antibodies: A Laboratory Manual*, supra).

Polyclonal antibodies can be readily generated by one of ordinary skill in the art from a variety of warm-blooded animals such as horses, cows, goats, sheep, dogs, chickens, turkeys, rabbits, mice, or rats. Briefly, the desired protein or peptide is utilized to immunize the animal through intraperitoneal, intramuscular, intraocular, or subcutaneous injections. The immunogenicity of the protein or peptide of interest may be increased through the use of an adjuvant such as Freund's complete or incomplete adjuvant. Following several booster immunizations, small samples of serum are collected and tested for reactivity to the desired protein or peptide.

Particularly preferred polyclonal antisera give a signal that is at least three times greater than background. Once the titer of the animal has reached a plateau in terms of its reactivity to the protein, larger quantities of polyclonal antisera may be readily obtained either by weekly bleedings, or by exsanguinating the animal.

Monoclonal antibodies can also be readily generated using well-known techniques (see U.S. Pat. Nos. RE 32,011, 4,902,614, 4,543,439, and 4,411,993; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988). Briefly, in one embodiment, a subject animal such as a rat or mouse is injected with a desired protein or peptide. If desired, various techniques may be utilized in order to increase the resultant immune response generated by the protein, in order to develop greater antibody reactivity. For example, the desired protein or peptide may be coupled to another protein such as ovalbumin or keyhole limpet hemocyanin (KLH), or through the use of adjuvants such as Freund's complete or incomplete adjuvant. The initial elicitation of an immune response, may preferably be through intraperitoneal, intramuscular, intraocular, or subcutaneous routes.

Between one and three weeks after the initial immunization, the animal may be reimmunized with another booster immunization. The animal may then be test bled and the serum tested for binding to the desired antigen using assays as described above. Additional immunizations may also be accomplished until the animal has reached a plateau in its reactivity to the desired protein or peptide. The animal may then be given a final boost of the desired protein or peptide, and three to four days later sacrificed. At this time, the spleen and lymph nodes may be harvested and disrupted into a single cell suspension by passing the organs through a mesh screen or by rupturing the spleen or lymph node membranes which encapsulate the cells. Within one embodiment the red cells are subsequently lysed by the addition of a hypotonic solution, followed by immediate return to isotonicity.

Within another embodiment, suitable cells for preparing monoclonal antibodies are obtained through the use of in vitro immunization techniques. Briefly, an animal is sacrificed, and the spleen and lymph node cells are removed as described above. A single cell suspension is prepared, and the cells are placed into a culture containing a form of the protein or peptide of interest that is suitable for generating an immune response as described above. Subsequently, the lymphocytes are harvested and fused as described below.

Cells that are obtained through the use of in vitro immunization or from an immunized animal as described above may be immortalized by transfection with a virus such as the Epstein-Barr Virus (EBV). (See Glasky and Reading, *Hybridoma* 8(4):377–389, 1989.) Alternatively, within a preferred embodiment, the harvested spleen and/or lymph node cell suspensions are fused with a suitable myeloma cell in order to create a "hybridoma" which secretes monoclonal antibodies. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Rockville, Md. (see *Catalogue of Cell Lines & Hybridomas*, 6th ed., ATCC, 1988). Representative myeloma lines include: for humans, UC 729-6 (ATCC No. CRL 8061), MC/CAR-Z2 (ATCC No. CRL 8147), and SKO-007 (ATCC No. CRL 8033); for mice, SP2/0-Ag14 (ATCC No. CRL 1581), and P3X63Ag8 (ATCC No. TIB 9); and for rats, Y3-Ag1.2.3 (ATCC No. CRL 1631), and YB2/0 (ATCC No. CRL 1662). Particularly preferred fusion lines include NS-1 (ATCC No. TIB 18) and P3X63—Ag 8.653 (ATCC No. CRL 1580), which may be utilized for fusions with either mouse, rat, or human cell lines. Fusion between the myeloma cell line and the cells from the immunized animal can be accomplished by a variety of methods, including the use of polyethylene glycol (PEG) (see *Antibodies: A Laboratory Manual*, Harlow and Lane, supra) or electrofusion. (See Zimmerman and Vienken, *J. Membrane Biol.* 67:165–182, 1982.)

Following the fusion, the cells are placed into culture plates containing a suitable medium, such as RPMI 1640 or DMEM (Dulbecco's Modified Eagles Medium, JRH Biosciences, Lenexa, Kans.). The medium may also contain additional ingredients, such as Fetal Bovine Serum (FBS, e.g., from Hyclone, Logan, Utah, or JRH Biosciences), thymocytes that were harvested from a baby animal of the same species as was used for immunization, or agar to solidify the medium. Additionally, the medium should contain a reagent which selectively allows for the growth of fused spleen and myeloma cells. Particularly preferred is the use of HAT medium (hypoxanthine, aminopterin, and thymidine) (Sigma Chemical Co., St. Louis, Mo.). After about seven days, the resulting fused cells or hybridomas may be screened in order to determine the presence of antibodies which recognize the desired antigen. Following several clonal dilutions and reassays, hybridoma producing antibodies that bind to the protein of interest can be isolated.

Other techniques can also be utilized to construct monoclonal antibodies. (See Huse et al., "Generation of a Large Combinational Library of the Immunoglobulin Repertoire in Phage Lambda," *Science* 246:1275–1281, 1989; see also Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728–5732, 1989; see also Alting-Mees et al., "Monoclonal Antibody Expression Libraries: A Rapid Alternative to Hybridomas," *Strategies in Molecular Biology* 3:1–9, 1990; these references describe a commercial system available from Stratacyte, La Jolla, Calif., which enables the production of antibodies through recombinant techniques.) Briefly, mRNA is isolated from a B cell population and utilized to create heavy and light chain immunoglobulin cDNA expression libraries in the λIMMUNOZAP(H) and λIMMUNOZAP(L) vectors. These vectors may be screened individually or co-expressed to form Fab fragments or antibodies (see Huse et al., supra; see also Sastry et al., supra). Positive plaques can subsequently be converted to a non-lytic plasmid which allows high level expression of monoclonal antibody fragments from *E. coli*.

Similarly, binding partners can also be constructed utilizing recombinant DNA techniques to incorporate the variable regions of a gene that encodes a specifically binding antibody. The construction of these binding partners can be readily accomplished by one of ordinary skill in the art given the disclosure provided herein. (See Larrick et al., "Polymerase Chain Reaction Using Mixed Piers: Cloning of Human Monoclonal Antibody Variable Region Genes From Single Hybridoma Cells," *Biotechnology* 7:934–938, 1989; Riechmann et al., "Reshaping Human Antibodies for Therapy," *Nature* 332:323–327, 1988; Roberts et al., "Generation of an Antibody with Enhanced Affinity and Specificity for its Antigen by Protein Engineering," *Nature* 328:731–734, 1987; Verhoeyen et al., "Reshaping Human Antibodies: Grafting an Antilysozyme Activity," *Science* 239:1534–1536, 1988; Chaudhary et al., "A Recombinant Immunotoxin Consisting of Two Antibody Variable Domains Fused to Pseudomonas Exotoxin," *Nature* 339:394–397, 1989; see also U.S. Pat. No. 5,132,405 entitled "Biosynthetic Antibody Binding Sites".) Briefly, in one embodiment, DNA segments encoding the desired protein or peptide interest-specific antigen binding domains are amplified from hybridomas that produce a specifically binding monoclonal antibody, and are inserted directly into the genome of a cell that produces human antibodies. (See Verhoeyen et al., supra; see also Reichmann et al., supra.) This technique allows the antigen-binding site of a specifically binding mouse or rat monoclonal antibody to be transferred into a human antibody. Such antibodies are preferable for therapeutic use in humans because they are not as antigenie as rat or mouse antibodies.

In an alternative embodiment, genes that encode the variable region from a hybridoma producing a monoclonal antibody of interest are amplified using oligonudeotide primers for the variable region. These primers may be synthesized by one of ordinary skill in the art, or may be purchased from commercially available sources. For instance, primers for mouse and human variable regions including, among others, primers for $V_{Ha}$, $V_{Hb}$, $V_{Hc}$, $V_{Hd}$, $C_{Hl}$, $V_L$ and $C_L$ regions, are available from Stratacyte (La Jolla, Calif.). These primers may be utilized to amplify heavy or light chain variable regions, which may then be inserted into vectors such as IMMUNOZAP™(H) or IMMUNOZAP™(L,) (Stratacyte), respectively. These vectors may then be introduced into *E. coli* for expression. Utilizing these techniques, large amounts of a single-chain protein containing a fusion of the $V_H$ and $V_L$ domains may be produced (see Bird et al., *Science* 242:423–426, 1988).

Monoclonal antibodies and binding partners can be produced in a number of host systems, including tissue cultures, bacteria, eukaryotic cells, plants and other host systems known in the art.

Once suitable antibodies or binding partners have been obtained, they may be isolated or purified by many techniques well known to those of ordinary skill in the art (see *Antibodies: A Laboratory Manual*, Harlow and Lane, supra). Suitable techniques include peptide or protein affinity columns, HPLC or RP-HPLC, purification on protein A or protein G columns, or any combination of these techniques. Within the context of the present invention, the term "isolated" as used to define antibodies or binding partners means "substantially free of other blood components."

The antibodies and binding partners of the present invention have many uses. For example, antibodies may be utilized in flow cytometry to sort cells beating such a protein. Briefly, in order to detect the protein or peptide of interest on cells, the cells are incubated with a labeled monoclonal antibody which specifically binds to the protein of interest, followed by detection of the presence of bound antibody. These steps may also be accomplished with additional steps such as washings to remove unbound antibody. Labels suitable for use within the present invention are well known in the art including, among others, flourescein isothiocyanate (FITC), phycoerythtin (PE), horse radish peroxidase (HRP), and colloidal gold. Particularly preferred for use in flow cytometry is FITC, which may be conjugated to purified antibody according to the method of Keltkamp in "Conjugation of Fluorescein Isothiocyanate to Antibodies. I. Experiments on the Conditions of Conjugation," *Immunology* 18:865–873, 1970. (See also Keltkamp, "Conjugation of Fluorescein Isothiocyanate to Antibodies. II. A Reproducible Method," *Immunology* 18:875–881, 1970; Goding, "Conjugation of Antibodies with Fluorochromes: Modification to the Standard Methods," *J. Immunol. Methods* 13:215–226, 1970.) The antibodies can also be used in blocking assays or for identification of receptors for Salmonella fimbrin or eukaryotic cells.

IV. Diagnostic Tests
A. Nucleic Acid Based Diagnostic Tests

Another aspect of the present invention provides probes and piers for detecting Salmonella.

In one embodiment of this aspect of the invention, probes are provided that are capable of specifically hybridizing to $sefU_1$, $sefU_2$, sefA, sefB, sefC, sefD, agfA, tctA, tctB, and/or tctC genes DNA or RNA. For purposes of the present invention, probes are "capable of hybridizing" to $sefU_1$, $sefU_2$, sefA, sefB, sefC, sefD, agfA, tctA, tctB, and/or tctC genes DNA or RNA if they hybridize under conditions of either high or moderate stringency (see Sambrook et al., supra). Preferably, the probe may be utilized to hybridize to suitable nucleotide sequences under highly stringent conditions, such as 6×SSC, 1×Denhardt's solution (Sambrook et al., supra), 0.1% SDS at 65° C. and at least one wash to remove excess probe in the presence of 0.2×SSC, 1×Denhardt's solution, 0.1% SDS at 65° C. Except as otherwise provided herein, probe sequences are designed to allow hybridization to Salmonella DNA or RNA sequences, but not to DNA or RNA sequences from other organisms, particularly other bacteria, including other genera of the family Enterobacteriaceae sequences. The probes are used, for example, to hybridize to nucleic acid that has been exposed from a cell in a sample. The hybridized probe is then detected, thereby indicating the presence of the desired cellular nucleic acid. Preferably, the cellular nucleic acid is subjected to an amplification procedure, such as PCR, prior to hybridization.

Probes of the present invention may be composed of either deoxyribonucleic acids (DNA) or ribonucleic acids (RNA), and may be as few as about 12 nucleotides in length, usually about 14 to 18 nucleotides in length, and possibly as large as the entire sequence of the $sefU_1$, $sefU_2$, sefA, sefB, sefC, sefD, agfA, tctA, tctB, and/or tctC genes. Selection of probe size is somewhat dependent upon the use of the probe, and is within the skill of the art.

Suitable probes can be constructed and labeled using techniques that are well known in the art. Shorter probes of, for example, 12 bases can be generated synthetically. Longer probes of about 75 bases to less than 1.5 kb are preferably generated by, for example, PCR amplification in the presence of labeled precursors such as [$\alpha$-$^{32}$P]dCTP, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells. (See Sambrook et al., supra.)

Probes can be labeled by a variety of markers, including for example, radioactive markers, fluorescent markers, enzymatic markers, and chromogenic markers. The use of $^{32}$P is particularly preferred for marking or labeling a particular probe.

It is a feature of this aspect of the invention that the probes can be utilized to detect the presence of Salmonella mRNA or DNA within a sample. However, if the bacteria is present in only a limited number, then it may be beneficial to amplify the relevant sequence such that it may be more readily detected or obtained.

A variety of methods may be utilized in order to amplify a selected sequence, including, for example, RNA amplification (see Lizardi et al., *Bio/Technology* 6:1197–1202, 1988; Kramer et al., *Nature* 339:401–402, 1989; Lomeli et al., *Clinical Chem.* 35(9):1826–1831, 1989; U.S. Pat. No. 4,786,600), and DNA amplification utilizing LCR or Polymerase Chain Reaction ("PCR") (see, U.S. Pat. Nos. 4,683,195, 4,683,202, and 4,800,159) (see also U.S. Pat. Nos. 4,876,187 and 5,011,769, which describe an alternative detection/amplification system comprising the use of scissile linkages), or other nucleic acid amplification procedures that are well within the level of ordinary skill in the art. With respect to PCR, for example, the method may be modified as known in the art. Transcriptional enhancement of PCR may be accomplished by incorporation of bacteriophage T7 RNA polymerase promoter sequences in one of the primary oligonucleotides, and immunoenzymatic detection of the products from the enhanced emitter may be effected using anti-RNA:DNA antibodies 0(Blais, *Appl. Environ. Microbiol.* 60:348–352, 1994). PCR may also be used in combination with reverse dot-blot hybridization (Iida et al., *FEMS Microbiol. Lett.* 114:167–172, 1993). PCR products may be quantitatively analyzed by incorporation of dUTP (Duplàa et al., *Anal. Biochem.* 212:229–236, 1993), and samples may be filter sampled for PCR-gene probe detection (Bej et al., *Appl. Environ. Microbiol.* 57:3529–3534, 1991).

Within a particularly preferred embodiment, PCR amplification is utilized to detect Salmonella DNA. Briefly, as described in greater detail below, a DNA sample is denatured at 95° C. in order to generate single-stranded DNA. Specific primers are then annealed to the single-stranded DNA at 37° C. to 70° C., depending on the proportion of AT/GC in the primers. The primers are extended at 72° C. with Taq DNA polymerase in order to generate the opposite strand to the template. These steps constitute one cycle, which may be repeated in order to amplify the selected sequence.

Within an alternative preferred embodiment, LCR amplification is utilized for amplification. LCR palmers are synthesized such that the 5' base of the upstream palmer is capable of hybridizing to a unique base pair in a desired gene to specifically detect a strain of Salmonella harboring the desired gene.

Within another preferred embodiment, the probes are used in an automated, non-isotopic strategy wherein target nucleic acid sequences are amplified by PCR, and then desired products are determined by a colorimetric oligonucleotide ligation assay (OLA) (Nickerson et al., *Proc. Natl. Acad. Sci. USA* 81:8923–8927, 1990).

Primers for the amplification of a selected sequence should be selected from sequences that are highly specific and form stable duplexes with the target sequence. The primers should also be non-complementary, especially at the 3' end, should not form dimers with themselves or other primers, and should not form secondary structures or duplexes with other regions of DNA. In general, primers of about 18 to 20 nucleotides are preferred, and can be easily synthesized using techniques well known in the art. PCR products, and other nucleic acid amplification products, may be quantitated using techniques known in the art (Duplàa et al., *Anal. Biochem.* 212:229–236, 1993; Higuchi et al., *Bio/Technology* 11:1026–1030).

B. Antibody-based Diagnostic Tests

Still another aspect of the present invention provides antibodies, as discussed above, for detecting Salmonella in diagnostic tests.

Such antibodies are useful in a wide variety of antibody-based assays. As discussed above, exemplary assays are described in detail in *Antibodies: A Laboratory Manual*, (supra); U.S. Pat. No. 4,736,110; and U.S. Pat. No. 4,486,530.

These antibody-based diagnostic tests include the following tests.

A fluorescent antibody test (FA-test) uses a fluorescently-labeled antibody able to bind to one of the proteins of the invention. For detection, visual determinations are made by a technician using fluorescence microscopy, yielding a qualitative result. In a preferred embodiment, this assay is used for the examination of tissue samples and histological sections.

In latex bead agglutination assays, antibodies to one or more of the proteins of the present invention are conjugated to latex beads. The antibodies conjugated to the latex beads are then contacted with a sample under conditions permitting antibodies to bind to desired proteins in the sample, if any. The results are then read visually, yielding a qualitative result. In a preferred embodiment, this format can be used in the field for on-site testing.

Enzyme immunoassays (EIA) include a number of different assays able to utilize the antibodies provided by the present invention. For example, a heterogeneous indirect EIA uses a solid phase coupled with an antibody of the invention and an affinity purified, anti-IgG immunoglobulin preparation. Preferably, the solid phase is a polystyrene microtiter plate. The antibodies and immunoglobulin preparation are then contacted with the sample under conditions permitting antibody binding, which conditions are well known in the art. The results of such an assay can be read visually, but are preferably read using a spectrophotometer, such as an ELISA plate reader, to yield a quantitative result.

An alternative solid phase EIA format includes a plastic-coated ferrous metal beads able to be moved during the procedures of the assay by means of a magnet. Yet another alternative is a low-light detection immunoassay format. In this highly sensitive format, the fight emission produced by appropriately labeled bound antibodies are quantitated automatically. Preferably, the reaction is performed using microtiter plates.

In a capture-antibody sandwich enzyme assay, the desired protein is bound between an antibody attached to a solid phase, preferably a polystyrene microtiter plate, and a labeled antibody. Preferably, the results are measured using a spectrophotometer, such as an ELISA plate reader.

In an alternative embodiment, a radioactive tracer is substituted for the enzyme mediated detection in an EIA to produce a radioimmunoassay (RIA).

In a sequential assay format, reagents are allowed to incubate with the capture antibody in a step wise fashion. The test sample is first incubated with the capture antibody. Following a wash step, an incubation with the labeled antibody occurs. In a simultaneous assay, the two incubation periods described in the sequential assay are combined. This eliminates one incubation period plus a wash step.

A dipstick/immunostick format is essentially an immunoassay except that the solid phase, instead of being a polystyrene microtiter plate, is a polystyrene paddle or dipstick. Reagents are the same and the format can either be simultaneous or sequential.

In a chromatographic strip test format, a capture antibody and a labeled antibody are dried onto a chromatographic strip, which is typically nitrocellulose or nylon of high porosity bonded to cellulose acetate. The capture antibody is usually spray dried as a line at one end of the strip. At this end there is an absorbent material that is in contact with the strip. At the other end of the strip the labeled antibody is deposited in a manner that prevents it from being absorbed into the membrane. Usually, the label attached to the antibody is a latex bead or colloidal gold. The assay may be initiated by applying the sample immediately in front of the labeled antibody.

Immunofiltration/immunoconcentration formats combine a large solid phase surface with directional flow of sample/reagents, which concentrates and accelerates the binding of antigen to antibody. In a preferred format, the test sample is preincubated with a labeled antibody then applied to a solid phase such as fiber filters or nitrocellulose membranes or the like. The solid phase can also be precoated with latex or glass beads coated with capture antibody. Detection of analyte is the same as standard immunoassay. The flow of sample/reagents can be modulated by either vacuum or the wicking action of an underlying absorbent material.

A threshold biosensor assay is a sensitive, instrumented assay amenable to screening large number of samples at low cost. In one embodiment, such an assay comprises the use of light addressable potentiometric sensors wherein the reaction involves the detection of a pH change due to binding of the desired protein by capture antibodies, bridging antibodies and urease-conjugated antibodies. Upon binding, a pH change is effected that is measurable by translation into electrical potential ($\mu$volts). The assay typically occurs in a very small reaction volume, and is very sensitive. Moreover, the reported detection limit of the assay is 1,000 molecules of urease per minute.

EXAMPLES

Example 1

Cloning of the agfA gene of *Salmonella enteritidis*

An AgfA-negative TnphoA insertion mutant of *S. enteritidis* 27655-3b, named strain 2-7f, was constructed (Collinson et al., "Thin, aggregative fimbriae mediate binding of *Salmonella enteritidis* to fibronectin," *J. Bacteriol.* 175:12–18, 1993). The strain contains an agfA-TnphoA gene fusion. Stock cultures of strain 2-7f were prepared using cells from mid-exponential phase cultures that were mixed with 15% glycerol and then stored at −80° C. in Luria-Bertani (LB) broth. Isolated colonies of strain 2-7f were obtained by inoculation of solid LB medium followed by incubation at 37° C. for 24 hours. An individual colony was inoculated in 2 ml of LB broth contained in a sterile 18 mm×150 mm test tube and the inoculation was incubated for 48 hours at 37° C. under static conditions. For the purpose of isolation of DNA for amplification of agfA, cells may be equally effectively prepared by growth in LB broth, Colonization Factor Antigen (CFA) broth, T (tryptone)-medium, other suitable proteolytic digest-based medium, or other medium suitable to support the growth of Salmonella. Cells may also be grown under aeration, such as by growth of the culture in an Erlenmeyer or other flask positioned on a rotary or gyratory shaking device. Preferably, the culture is grown at temperatures between 20° C. and 37° C.

Cells of strain 2-7f composing the pellicle at the surface of a static culture and cells in suspension were mixed by vortexing for 1 minute. Cells were harvested from 1 ml of this cell suspension (approximately 20 mg wet weight of cells) transferred to a 1.5 ml polypropylene microfuge tube and centrifuged (16,000×g for 5 min. at 21° C). The pelleted cells were saved and subsequently resuspended in 1 ml of distilled water. The cells were lysed to release cellular DNA by boiling the 1 ml sample in a sealed microfuge tube for 5 minutes. The cell lysate was partially clarified by centrifugation (16,000×g for 10 min. at 4° C.) in a microfuge to pellet cell debris. The crude DNA preparation (supernatant fraction) was used as a substrate for amplification of a 394 bp DNA fragment encoding the majority of the SEF17 fimbrin subunit, agfA.

Standard molecular cloning techniques were performed according to protocols described by Sambrook et al. (*Molecular Cloning: A Laboratory Manual, Cold Spring Harbor Press*, Cold Spring Harbor, N.Y., 1989), or by incorporating minor modifications thereto that are well known in the art. To facilitate cloning of an amplified agfA fragment, PCR primers were constructed to include restriction endonuclease cleavage sites. The 5' PCR primer, called TAF1, was a 34 bp biased, degenerate oligonucleotide dGGCGGAAGCTTGAATTCGT[A/C/T]GT[A/C/T]C C[A/G/T]CA[A/G]TGGGG) (SEQ ID No. 2), of which the 17 bases at the 3' end correspond to amino acid residues 2 to 7 of the Agfa N-terminus (the final nucleotide of amino acid 7 is degenerate, and therefore was not made a part of the primer). The amino acid sequence of the N-terminus had been previously determined by Collinson et al. (supra). The underlined sequences were required to create HindIII and EcoRI cleavage sites in the product of DNA amplification. The 3' PCR primer, called TAF2, (dGGGAAAGGTTGAATTCAGGACGCTACTTGTG) (SEQ ID No. 3), into which three nucleotide changes (underlined) were introduced to create an EcoRI site in the PCR product, was complementary to the $IS50_L$ sequence residing at the junction of TnphoA generated alkaline phosphatase gene fusions. The amplified 394 bp agfA fragment was isolated after agarose (1.5%) gel electrophoresis using a 40 mM Tris-acetate, 1 mM EDTA buffer system and then purified using Gene Clean II glassmilk following the 'double Gene Clean' protocol recommended by the manufacturer (Bio 101 Inc., La Jolla, Calif.).

Approximately 0.5 μg of the amplified agfA fragment was cleaved with the restriction endonuclease EcoRI at a concentration of 5 units per μg of DNA. In addition, 0.5 μg of the plasmid vector pUC19 (Yannisch-Perron et al., "Improved M13 phage cloning vectors and host strains: nucleotide sequences of the M13mp18 and pUC19 vectors," Gene 33:103–119, 1985) was similarly digested with EcoRI. After digestion, the DNA samples were extracted once with 0.75 volume of buffered-phenol and then with 0.75 volume of chloroform to separate enzyme from DNA. The digested DNA fragments were precipitated in the presence of 2.5 volumes of 95% ethanol and 0.3M sodium acetate, pH 5.4. Residual ethanol was removed from the DNA pellets under vacuum.

The DNA was dissolved in 20 μl of 10 mM TrisHCl-1 mM EDTA, pH 8.0. Ligation of agfA DNA fragments into pUC19 was conducted in 50 μl ligation buffer using 7 units of T4 DNA ligase. Clones containing recombinant plasmids were obtained by transformation of competent cells of E. coli strain DH5α obtained from GIBCO BRL Life Technologies Inc. (Buffington, Ontario, Canada) with a sample of ligated DNA. Transformed cells were selected on solid LB medium containing (200 μg/ml) ampicillin, 50 μM IPTG (isopropyl-β-D-thiogalactopyranoside) and 0.005% X-GAL (5-bromo-4-chloro-3-indoyl-β-D-galactoside). Ampicillin resistant colonies that contained the recombinant plasmids were identified by their white color. Recombinant plasmid DNA was purified from transformed cells using a modification of the standard, small scale, alkaline lysis technique described by Sambrook et al. (supra). Recombinant plasmids were purified from three individually isolated colonies. These three, apparently identical, plasmids were designated pAGF1, pAGF3 and pAGF4.

In order to obtain a clone containing the full agfA gene, chromosomal DNA of S. enteritidis strain 27655-3b was purified by CsCl gradient centrifugation and digested separately with HindIII or DraI and analyzed by Southern hybridization at 65° C. using a random-primer, [α-$^{32}$P]dATP labeled agfA PCR fragment according to methods described by Sambrook et al. (supra). Following stringent filter washing at 60° C. to 62° C. as described above, a genomic fragment of approximately 3 kb was identified. HindIII or DraI digested strain 3b DNA was fractionated according to size by sucrose gradient centrifugation (Sambrook et al., supra). DNA fragments contained in the fraction found to hybridize to the [$^{32}$P]-labeled agfA PCR fragment were ligated into M13mp18 (Yannisch-Perron et al., supra) at the HindIII site or SmaI site within the multiple cloning site at 12° C. using 12 units of ligase and a total of 1 μg of DNA at a final concentration of 50 μg/μl. Recombinant plaques prepared on a lawn of E. coli JM109 (Yannisch-Perron et al., supra), containing agfA were identified by dot blot hybridization (Sambrook et al., supra) using the [$^{32}$P]-labeled agfA PCR fragment. The recombinant M13mp18 bacteriophage containing agfA were plaque purified in the replicative form, double-stranded DNA was purified and the insert fragments encoding agfA were cloned into pUC18 (Yannisch-Perron et al., supra), and transformed into E. coli strain DH5α as described by Sambrook et al. (supra). The recombinant plasmid composed of pUC18 and the approximately 3 kb DraI fragment of strain 3b DNA was named pDAG6. The recombinant plasmid formed from pUC18 and the approximately 3 kb HindIII fragment of strain 3b genomic DNA was named pHAG10.

The following Examples are offered by way of illustration, and not by way off limitation.

Example 2

Determination of the DNA sequence of agfA

The DNA sequences of both strands of the agfA PCR fragment of Example 1 were determined by a modification of the enzymatic, dideoxy-termination sequencing method (Sanger et al., "DNA sequencing with chain-termination inhibitors," Proc. Natl. Acad. Sci. USA 74:5463–5467, 1977) using the universal forward and reverse primers and the reagents and protocols supplied in the Sequenase™ Version 2.0 kit (United States Biochemicals, Cleveland, Ohio). The sequence was confirmed by determining the DNA sequence of agfA contained in two of the independent plasmid clones. For this determination, an Applied Biosystems model 373A automated DNA sequencer and associated reagents, protocols and software (version 1.10) for thermal cycle sequencing (Applied Biosystems Canada Inc., Mississauga, ON) was used. The universal forward and reverse sequencing primers (Yannisch-Perron et al., supra) were used. The DNA sequence of agfA encoded on the overlapping HindIII and DraI fragments cloned in pHAG10 and pDAG6 was determined on both strands using double-strand DNA sequencing techniques.

Computer analysis of the DNA sequence for open reading frames and gene translation was performed using DNA Strider, version 1.1. The start of the open reading frame of the agfA gene encoding the mature AgfA fimbrin was recognized by comparison of the translated sequence to the N-terminal amino acid sequence of AgfA. The agfA PCR fragment DNA sequence is presented in FIG. 7A.

The full agfA gene sequence cloned into pHAG10 (and the agfA gene sequence from a separate clone, pDAG6), was determined on both strands using double-stranded sequencing techniques. The sequence is provided in FIG. 7B. The translated DNA sequence of the single open reading flame corresponded precisely to amino add residues 2 to 31 determined by N-terminal sequencing of Agfa (FIGS. 7A and 7B). The amino acid composition of the translated sequence had a similar high glycine content (16%), high combined alanine, serine plus glycine content (37%), low basic amino acid content (4.5%), and nearly 30% asparagine plus aspartic acid content consistent with the total amino acid analysis of native Agfa fimbrin (8). Based on the estimated molecular weight of Agfa of 17K $M_r$, and the expected molecular weight of the protein encoded in the 333 bp region of agfA, about 12K–13K $M_r$, it appears that about three quarters of SEF17 fimbrin is represented in the fragment.

Example 3

Hybridization of the agfA probe to dot blots and colony blots of eubacteria DNA

The strains of Salmonella, other Enterobacteriaceae, and eubacteria used for hybridization studies and PCR assays, and the sources of the bacteria, are provided in Table 1. Panels of Enterobacteriaceae in arrays on hydrophobic grid membrane filters (HGMF; Gelman Sciences, Montreal, PQ) were replicated (HGMF Replicator, Richard Brancker Research, Ottawa, ON) and grown as described by Sharpe et al. ("Technique for maintaining and screening many microbial cultures," *Food Microbiol.* 6:261-265, 1989). All bacteria were grown on LB medium or Nutrient broth medium at 37° C. except isolates of *Serratia marcescens* and *Erwinia caratovora* which were grown at 25° C. and *Aeromonas salmonicida* and *Aeromonas hydrophila* which were grown at 20° C.

The agfA gene fragment represented in FIG. 1 was hybridized to DNA from a total of 896 bacterial strains represented as colony blots on HGMF or as DNA dot blots on nylon membranes (Table 1). DNA dot-blot hybridization was used to screen 58 Salmonella isolates, 27 other Enterobacteriaceae spp. and 4 other eubacteria. Chromosomal DNAs were purified from proteinase K-treated cell lysates by repeated phenol-chloroform extraction followed by ethanol precipitation and resuspension (Sambrook et al., supra). The DNA samples were quantified by spectroscopy and 0.5 µg samples were applied to HyBond-N⁺ nylon membranes (Amersham Canada Inc., Oakville, ON) using a dot-blot manifold. The remaining 546 Salmonella sorovars, 239 other Enterobacteriaceae strains, and 22 isolates of other eubacteria were screened for agfA related genes as colony blots prepared on HGMF as described by Peterkin et al. ("Screening DNA probes using the hydrophobic grid-membrane filter," *Food Microbiol.* 6:281-284, 1989).

The presence of Salmonella DNA was detected by hybridization with a mixture of total DNA prepared from *S. enteritidis, S. typhimurium* and *S. berta* and labeled with [$\alpha$-$^{32}$P] dATP by random-primer-directed DNA synthesis (Sambrook et al., supra). An agfA gene probe was similarly prepared by radiolabeling the 394 bp agfA PCR amplified fragment. DNA blots were prehybridized at 65° C. in buffer (Sambrook et al., supra) containing 20 µg/ml herring sperm DNA. Following hybridization at 65° C., the membranes were washed at a high stringency (0.2×SSPE buffer (Sambrook et al., supra), 0.1% SDS, 63° C.) to maximize the signal difference between strongly and weakly hybridized bacterial genomic DNA samples. The hybridization results were recorded by autoradiography on X-OMAT AR5 film (Kodak, Rochester, N.Y.).

Virtually all (603 out of 604, or 99.8%) Salmonella isolates tested hybridized to the agfA gene probe. These 603 Salmonella strains represented 90 serovars from 23 serogroups. The serovars surveyed included those most frequently responsible for gastroenteritis worldwide, *S. enteritidis* and *S. typhimurium*, other prominent causes of salmonellosis in North America and Europe, *S. heidelberg, S. infantis, S. hadar, S. newport* and *S. agona*, and for entetic fever and septicemia, *S. typhi, S. paratyphi*A, *S. paratyphi* B and *S. choleraesuis*. A single isolate of *S. saint-paul* did not hybridize to the agfA probe, although six other *S. saint-paul* isolates did hybridize. DNA preparations from 235 of 266 strains of other genera of Enterobacteriaceae and DNA samples from 26 unrelated eubacteria did not hybridize to the agfA gene probe. The agfA gene probe hybridized very weakly to heterologous DNA on HGMF derived from 11 of 120 *E. coli* isolates, 2 of 12 Citrobacter spp. and 1 of 16 Enterobacter spp. The relatively negligible levels of hybridization to these isolates distinguished them from strongly hybridizing Salmonella DNA. No hybridization was detected to species of Erwinia, Hafnia, Klebsiella, Proteus, Providencia, Serratia, Shigella or Yersinia or several other eubacterial species.

Figure 10A:
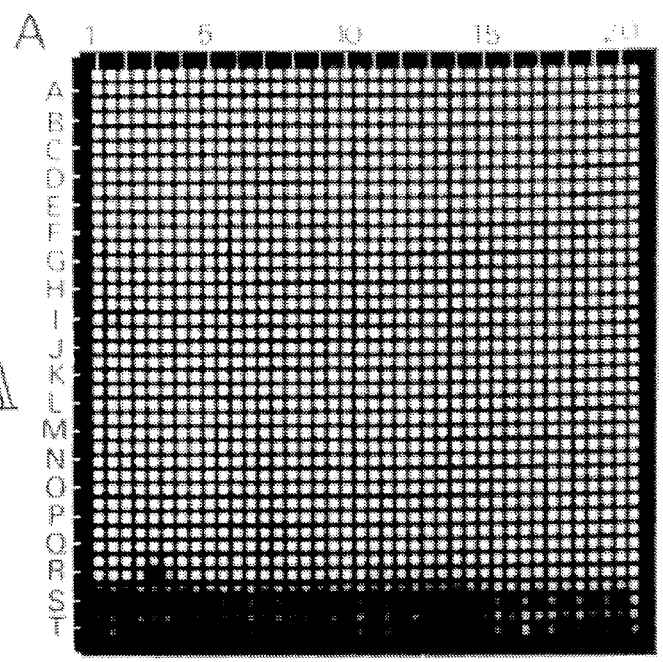
FIG. 10A depicts an autoradiograph of the hybridization of [$^{32}$P]-labeled agfA gene probes derived by PCR from *S. enteritidis* 27655-3b TnphoA mutant 2-7f to representative panels of HGMF colony blots. Panel positions: A1–F20, *E. coli* strains; G1-G12, Citrobacter spp.; I1–I16, Enterobacter spp.; J1–J5, Hafnia spp.; K1–K15, Proteus spp.; L1–L7, Klebsiella spp.; M1-N3, Shigella spp.; N9–P20, Yersinia spp.; Q1–Q4, Aeromonas spp.; Q5, Boriella; Q6–Q7, Erwinia spp.; Q5–Q9, Providencia spp.; Q10–Q13, Serratia spp.; Q14–Q15, Acinetobacter spp.; Q16–Q17, Achromobacter spp.; Q18–Q19, Alcaligenes spp.; Q20, *Serratia marcescens*; R1–R12, Pseudomonas spp.; R3 and S1–T20, Salmonella spp.; G13–H20, I17–I20, J6–J20, K16–K20, L8–L20, N4–N8, R13–R20, no bacteria applied.
Figure 10B:
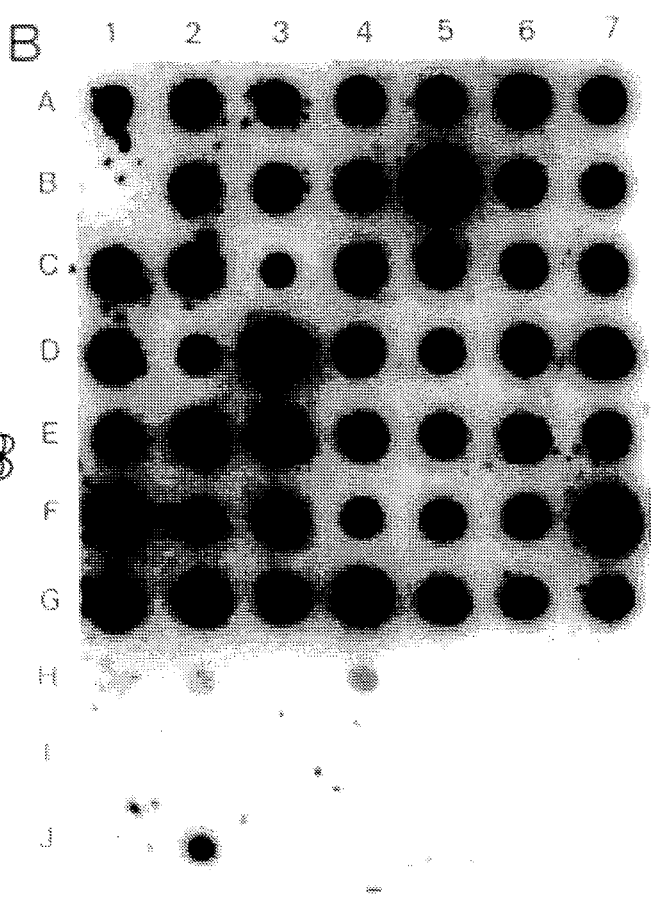
FIG. 10B depicts an autoradiograph of the hybridization of [$^{32}$P]-labeled agfA gene probes derived by PCR from *S. enteritidis* 27655-3b TnphoA mutant 2-7f to representative panels of DNA dot blots. Panel positions: A1–A7 and B2–G7, Salmonella spp.; A1–A7, B2–C3, *S. enteritidis* isolates; C4–C6, *S. berta* isolates; C7–D4, *S. pullorum* isolates; D5, *S. gallinarum*; D6–E4, *S. dublin* isolates; E5, *S. drypool*; E6, *S. eastbourne*; E7, *S. albany*; F1, *S. anatum*; F2, *S. arizonae*; F3, *S. cerro*; F4, *S. choleraesuis*; F5, *S. dahomey*; F6, *S. florida*; F7, *S. gamincara*; G1, *S. havana*; G2, *S. minnesota*; G3, *S. newport*; G4, *S. neinstedten*; G5, *S. tennessee*; G6, *S. typhimurium*; G7, *S. worthington*; H1, *Citrobacter freundii* 8090; H2, *E. coli*; H3, *Serratia marcescens*; H4, *Shigella sonnei*; H5, *Klebsiella pneumoniae* 13983; H6, *Enterobacter aerogenes*; H7, *Hafnia alvei*; I1, *Erwinia caratovora*; I2, *Proteus vulgaris*; I3, Providencia sp.; I4, *Pseudomonas aeruginosa*; I5, *Aeromonas hydrophila*; I6, *Aeromonas salmonicida*: I7, *Bacillus subtilus*; J1, herring sperm DNA; J2, *Salmonella paratyphi* A; B and J3–I7, blank.

Therefore, under highly stringent conditions, the agfA nucleotide probe in combination with HGMF technology demonstrated excellent inclusivity and exclusivity properties (FIG. 10A). Alternatively, DNA dot blots prepared from 0.5 µg amounts of purified genomic DNA provided a more sensitive, but less practical, means of screening using the agfA DNA probe (FIG. 10B). Accordingly, weak hybridization was detected to DNA from 15 of 17 *E. coli* isolates, 10 of which produced GVVPQ fimbrin detectable by Western blotting, and to a single strain *Shigella sonnei* but not to other Enterobacteriaceae DNA samples.

TABLE 1

| Hybridization of agfA DNA probe to Salmonella and other Enterobacteriaceae | | | | |
|---|---|---|---|---|
| Bacterial Species or Serovar | Strain | Source[a] | Serogroup | Hybridization to agfA probe[b] |
| Salmonella | | | | |
| *S. agona* | | HPB | B | 13/13 |
| *S. alachua* | | HPB | O | 1/1 |
| *S. albany* | | TJT | C3 | + |
| | | HPB | C3 | 6/6 |
| *S. anatum* | | UVIC | E1 | + |
| | | HPB | E1 | 14/14 |
| *S. arizonae* | | TJT | | + |
| | | HPB | | 4/4 |
| *S. arkansas* | | HPB | E3 | 4/4 |
| *S. bardo* | | HPB | C3 | 1/1 |
| *S. barielly* | | HPB | C1 | 12/12 |
| *S. berta* | 8392 | ATCC | D1 | + |
| | 89-4065 | PVL | D1 | + |
| | 90-1271 | PVL | D1 | + |
| | | HPB | D1 | 4/4 |
| *S. binza* | | HPB | E2 | 6/6 |
| *S. blockley* | | HPB | C2 | 5/5 |
| *S. braenderup* | | HPB | C1 | 5/5 |
| *S. brandenburg* | | HPB | B | 3/3 |
| *S. bredeney* | | HPB | B | 8/8 |

TABLE 1-continued

Hybridization of agfA DNA probe to Salmonella and other Enterobacteriaceae

| Bacterial Species or Serovar | Strain | Source[a] | Serogroup | Hybridization to agfA probe[b] |
|---|---|---|---|---|
| S. brunei | | HPB | C3 | 1/1 |
| S. california | | HPB | B | 2/2 |
| S. cerro | | TJT | K | + |
| | | HPB | K | 7/7 |
| S. chester | | HPB | B | 1/1 |
| S. choleraesuis | | BBF | C1 | + |
| | | HPB | C1 | 1/1 |
| S. colindale | | HPB | C1 | 1/1 |
| S. cubana | | HPB | G2 | 2/2 |
| S. dahomey | | TJT | X | + |
| S. derby | | HPB | B | 3/3 |
| S. drypool | | UVIC | E2 | + |
| | | HPB | E2 | 1/1 |
| S. dublin | 15480 | ATCC | D1 | + |
| | 89-3349 | PVL | D1 | + |
| | 89-4189 | PVL | D1 | + |
| | 90-243 | PVL | D1 | + |
| | 90-1176 | PVL | D1 | + |
| | 89-3320 | PVL | D1 | + |
| | | HPB | D1 | 1/1 |
| S. ealing | | HPB | O | 1/1 |
| S. eastbourne | | UVIC | D1 | + |
| | | HPB | D1 | 2/2 |
| S. eimsbuettel | | HPB | C4 | 2/2 |
| S. elisabethville | | HPB | E1 | 1/1 |
| S. enteritidis | 27655-3b | TW | D1 | + |
| | 27036 2I | TW | D1 | + |
| | 27036 2II | TW | D1 | + |
| | 13076 | ATCC | D1 | + |
| | 4931 | ATCC | D1 | + |
| | 31194 | ATCC | D1 | + |
| | 809 | LCDC | D1 | + |
| | 813 | LCDC | D1 | + |
| | 907 | LCDC | D1 | + |
| | 913 | LCDC | D1 | + |
| | 914 | LCDC | D1 | + |
| | 930 | LCDC | D1 | + |
| | 939 | LCDC | D1 | + |
| | 955 | LCDC | D1 | + |
| | 972 | LCDC | D1 | + |
| | JTSe1 | JT | D1 | + |
| | 27655-3a | TW | D1 | + |
| | | HPB | D1 | 7/7 |
| S. flint | | HPB | Z | 1/1 |
| S. florida | | TJT | H | + |
| S. gallinarum | 9184 | ATCC | D1 | + |
| | | HPB | D1 | 1/1 |
| S. gaminara | | TJT | I | + |
| S. give | | HPB | E1 | 1/1 |
| S. godesberg | | HPB | N | 1/1 |
| S. haardt | | HPB | C3 | 9/9 |
| S. hadar | | HPB | C2 | 56/56 |
| S. halmstad | | HPB | E2 | 1/1 |
| S. hamburg | | TJT | B | + |
| S. havana | | TJT | G2 | + |
| | | HPB | G2 | 5/5 |
| S. heidelberg | | HPB | B | 26/26 |
| S. indiana | | HPB | B | 10/10 |
| S. infantis | JTSi1 | JT | C1 | + |
| | | HPB | C1 | 25/25 |
| S. isangi | | HPB | C1 | 1/1 |
| S. javiana | | HPB | D1 | 1/1 |
| S. johannesburg | | HPB | R | 22/22 |
| S. kentucky | | HPB | C3 | 11/11 |
| S. landau | | HPB | N | 1/1 |
| S. lexington | | HPB | E1 | 1/1 |
| S. lille | | HPB | C1 | 2/2 |
| S. litchfield | | HPB | C2 | 1/1 |
| S. livingstone | | HPB | C1 | 7/7 |
| S. london | | HPB | E1 | 4/4 |
| S. manhattan | | HPB | C2 | 1/1 |
| S. mbandaka | | HPB | C1 | 27/27 |
| S. meleagridis | | HPB | E1 | 2/2 |
| S. minnesota | | TJT | L | + |

TABLE 1-continued

Hybridization of agfA DNA probe to Salmonella and other Enterobacteriaceae

| Bacterial Species or Serovar | Strain | Source[a] | Serogroup | Hybridization to agfA probe[b] |
|---|---|---|---|---|
| | | HPB | L | 2/2 |
| S. montevideo | | HPB | C1 | 14/14 |
| S. muenchen | | HPB | C2 | 1/1 |
| S. muenster | | HPB | E1 | 6/6 |
| S. newbrunswick | | HPB | E2 | 2/2 |
| S. newington | | HPB | E2 | 13/13 |
| S. newport | | TJT | C2 | + |
| | | HPB | C2 | 5/5 |
| S. nienstedten | | TJT | C4 | + |
| | | HPB | C4 | 1/1 |
| S. ohio | | HPB | C1 | 11/11 |
| S. oranienberg | | HPB | C1 | 6/6 |
| S. orion | | HPB | E1 | 2/2 |
| S. panama | | HPB | D1 | 2/2 |
| S. paratyphi A. subsp. durazzo | 11511 | ATCC | A | + |
| S. paratyphi B | | HPB | B | 3/3 |
| S. poona | | HPB | G1 | 2/2 |
| S. pullorum | 9120 | ATCC | D1 | + |
| | 10398 | ATCC | D1 | + |
| | 19945 | ATCC | D1 | + |
| | 89-2331 | PVL | D1 | + |
| | 90-1175 | PVL | D1 | + |
| | | HPB | D1 | 2/2 |
| S. reading | | HPB | B | 2/2 |
| S. saint-paul | | HPB | B | 6/7 |
| S. sandiego | | HPB | B | 1/1 |
| S. schwarzengrund | | HPB | B | 18/18 |
| S. senftenberg | | HPB | E4 | 28/28 |
| S. stanley | | TJT | B | + |
| S. taksony | | HPB | E4 | 1/1 |
| S. tennessee | | TJT | C1 | + |
| | | HPB | C1 | 14/14 |
| S. thomasville | | HPB | E3 | 3/3 |
| S. thompson | | HPB | C1 | 18/18 |
| S. typhi | | HPB | D1 | 2/2 |
| S. typhimurium | F18-1 | TJT | B | + |
| | F112-2 | TJT | B | + |
| | S736 | TJT | B | + |
| | 962 | TJT | B | + |
| | JTst2 | JT | B | + |
| | JTst3 | JT | B | + |
| | | HPB | B | 34/34 |
| S. urbana | | HPB | N | 1/1 |
| S. wassenaar | | HPB | Z | 1/1 |
| S. weltsevreden | | HPB | E1 | 1/1 |
| S. westhampton | | HPB | E1 | 1/1 |
| S. worthington | | TJT | G2 | + |
| | | HPB | G2 | 6/6 |
| Other Enterobacteriaceae | | | | |
| Citrobacter freundii | 8090 | UVIC | | − |
| | | HPB | | −/+2[c]/11 |
| Citrobacter sp. | | GS | | −/+[c] |
| | | HPB | | 0/1 |
| Enterobacter aerogenes | | UVIC | | − |
| | | HPB | | 0/2 |
| Enterobacter agglomerans | | HPB | | 0/6 |
| Enterobacter cloacae | | HPB | | −/+1[c]/8 |
| Erwinia caratovora | | UVIC | | − |
| | | HPB | | 0/2 |
| Escherichia coli | 11775 | ATCC | | − |
| | C600 | ATCC | | −/+[c] |
| | HB101 | ATCC | | −/+[c] |
| | E1049a-13 | TJT | | −/+[c] |
| | B41M | LE | | − |
| | HM1475 | LE | | − |
| | 438 Hf | TJT | | −/+[c] |
| | B4 | GS | | −/+[c] |
| | Vietnam I/1 | LE | | −/+[c] |
| | Viet G | LE | | −/+[c] |
| | Gambia G3 | LE | | −/+[c] |
| | NG7c | LE | | −/+[c] |
| | NG7c1 | LE | | −/+[c] |
| | 135+ | GS | | −/+[c] |

TABLE 1-continued

Hybridization of agfA DNA probe to Salmonella and other Enterobacteriaceae

| Bacterial Species or Serovar | Strain | Source[a] | Serogroup | Hybridization to agfA probe[b] |
|---|---|---|---|---|
| | 314-H | GS | | –/+[c] |
| | 654-H | GS | | –/+[c] |
| | H2 | TJT | | –/+[c] |
| | | HPB | | –/+[c] 11/120 |
| Hafnia alvei | | UVIC | | – |
| | | HPB | | 0/5 |
| Klebsiella oxytoca | | HPB | | 0/1 |
| Klebsiella pneumonia | 13883 | ATCCjp36 | | |
| | | HPB | | 0/6 |
| Proteus mirabilis | | HPB | | 0/4 |
| Proteus morganii | | HPB | | 0/1 |
| Proteus rettgeri | | HPB | | 0/4 |
| Proteus vulgaris | | UVIC | | – |
| | | HPB | | 0/5 |
| Proteus sp. | | HPB | | 0/1 |
| Providencia rettgeri | | UVIC | | – |
| Providencia alcalifaciens | | HPB | | 0/1 |
| Providencia sp. | | HPB | | 0/2 |
| Serratia fonticola | | HPB | | 0/1 |
| Serratia marcescens | | UVIC | | – |
| | | HPB | | 0/4 |
| Shigella boydii | | HPB | | 0/2 |
| Shigella dysenteriae | | HPB | | 0/3 |
| Shigella flexneri | | HPB | | 0/14 |
| Shigella sonnei | | UVIC | | –/+[c] |
| | | HPB | | 0/4 |
| Yersinia enterocolitica | | HPB | | 0/27 |
| Yersinia frederiksenii | | HPB | | 0/1 |
| Yersinia intermedia | | HPB | | 0/3 |
| Yersinia pseudotuberculosis | | HPB | | 0/1 |
| Other eubacteria | | | | |
| Achromobacter spp. | | HPB | | 0/2 |
| Acinetobacter calcoaceticus | | HPB | | 0/2 |
| Aeromonas hydrophila | | TJT | | – |
| | | HPB | | 0/4 |
| Aeromonas salmonicida | | WWK | | – |
| Alcaligenes faecalis | | HPB | | 0/2 |
| Bacillus subtilis | | UVIC | | – |
| Bordetella bronchiseptica | | HPB | | 0/1 |
| Pseudomonas aeruginosa | | UVIC | | – |
| | | HPB | | 0/5 |
| Pseudomonas fluorescens | | HPB | | 0/2 |
| Pseudomonas putida | | HPB | | 0/2 |
| Pseudomonas stutzeri | | HPB | | 0/1 |
| Pseudomonas sp. | | HPB | | 0/1 |

[a]ATCC, American Type Culture Collection; BBF, B. B. Finlay, Biotechnology Laboratory and Departments of Biochemistry and Microbiology, University of British Columbia, Vancouver, Canada; GS, G. Sarlós, University Medical School, Institute of Microbiology, Pécs, Hungary; HPB, Health Protection Branch of health and Welfare Canada, Ottawa; JT, J. Tomas, Departement Microbiologie, Universitat de Barcelona, Spain; LCDC, H. Lior, Laboratory Centre for Disease Control, Ottawa, Canada; LE, L. Emödy, University Medical School, Institute of Microbiology, Pécs, Hungary; PVL, G. Thiele, Provincial Veterinary Laboratory of British Columbia, Abbotsford, Canada; TJT, T. J. Trust, Department of Biochemistry and Microbiology, University of Victoria, Canada; TW, T. Wadström, University of Lund, Sweden; UVIC, Culture Collection of the Department of Biochemistry and Microbiology, University of Victoria, Canada; WWK, W. W. Kay, Department of Biochemistry and Microbiology, University of Victoria, Canada. The strains designated as originating from source 'HPB' (Health Protection Branch of Health and Welfare Canada, Ottawa) were screened as panels of colony blots on HGMF membranes (32, 40) for hybridization to the agfA DNA probe only.
[b]Hybridization of samples of membrane-bound bacterial DNA to the 394 bp agfA gene probe. The results of hybridization to dot blots of purified bacterial DNA are reported as positive '+', negative '–', or +/– for very weak hybridization. Hybridization of the agfA probe to DNA samples represented as colony blots on HGMF (HPB) panels are reported as the number of positively hybridizing strains per total number of strains tested.
[c]DNA from these strains hybridized very weakly to the 394 bp agfA probe.

Example 4 agfA-based PCR assays targeting Salmonella

A set of oligonucleotide primers was designed for amplification of agfA from Salmonella sequences. Accordingly, primers TAF3 and TAF4 allowed Salmonella specific PCR amplification of a 261 bp agfA DNA fragment. Specifically, PCR primers TAF3 (dTCCGGCCCGGACTCAACG) (SEQ ID No. 4), and TAF4 (dCAGCGCGCCGTTATTACCG) (SEQ ID No. 5) targeted complementary strands of agfA in regions corresponding to Agfa amino acid residues 19 to 24 and 100 to 105, respectively (FIG. 1). As described above, bacterial DNA samples for PCR analyses were prepared from cells (20 mg wet weight) resuspended in 1 ml of distilled, deionized $H_2O$ and lysed by boiling for 5 minutes. Cell lysates containing DNA were clarified by centrifugation (16,000×g, 5 min., 25° C.). If not used immediately, the samples were stored frozen at −20° C.

Amplification was carded out in a 10 μl reaction volume containing 1 μl of heat-denatured bacterial DNA solution, 5 pmol of each primer, the four deoxynucleotide triphosphates at 0.5 mM each, and 0.4 units of Taq DNA polymerase (Stratagene, La Jolla Calif.) in reaction buffer consisting of 50 mM Tris-HCl, pH 8.5, 20 mM KCl, 2.5 mM $MgCl_2$ and 0.5 mg/ml BSA. Thermocycling was performed on samples contained in sealed glass capillary tubes inserted in an Idaho Technology air driven thermocycler for 30 cycles of denaturation (95° C., 5 s), annealing (68° C., 1 s) and elongation (74° C., 30 s). Annealing temperatures of 68° C. to 70° C. were used to provide Salmonella specific PCR amplification of an internal agfA fragment. Products of DNA amplification were separated by electrophoresis in 15% polyacrylamide gels and visualized by UV illumination following ethidium bromide staining.

Under these conditions, in a survey of Salmonella, including strains of *S. agona*, *S. choleraesuis*, *S. enteritidis* 27665-3b, *S. hadar* F9-1, *S. heidelberg* ATCC 8326, *S. infantis* S41-16, *S. newport*, *S. paratyphi* A ATCC 11511, *S. typhi* and *S. typhimurium* SU453, TAF3 and TAF4 primed Salmonella specific amplifications of agfA DNA yielding fragments of approximately 260 bp (FIG. 8), consistent with the predicted size of 261 bp. Using TAF3 and TAF4 there was no amplification from DNA isolated from strains of *E. coli*, *Shigella sonnei*, *C. freundii*, *Enterobacter aerogenes*, *Erwinia caratovora*, *H. alvei*, *K. pneumoniae*, *Proteus vulgaris*, *Serratia marcescens* or *Providencia* at annealing temperatures above 55° C.

Example 5 agfA-based PCR assays targeting Salmonella and other enteropathogenic bacteria

A set of oligonucleotide primers was designed to amplify agfA-related genes present in other enteropathogenic bacteria. Accordingly, primers TAF5 and TAF6 allow amplification of approximately 92 bp DNA fragments from both agfA and related genes. Specifically, the 5' PCR primer was TAF5 (5'-dGGCGGCGGCAATA[G/A]TTCCGGCCCG-3') (SEQ ID No. 6) corresponding to amino acid residues 14 to 21 of Agfa and the 3' PCR primer was TAF6 (5'-dCGGGCATCGCTTTGCAGAGGAAGCGC-3') (SEQ ID No. 7) corresponding to amino acid residues 36 to 44 (FIG. 7A).

Bacterial DNA samples for PCR analyses were prepared from cells (20 μg wet weight) resuspended in 1 ml of distilled, deionized $H_2O$ and lysed by boiling for 5 minutes. Cell lysates containing DNA were clarified by centrifugation (16,000×g, 5 min, 25° C.) and stored at −20° C. Amplification was carded out in a 10 μl reaction volume containing 1 μl of heat-denatured bacterial DNA solution, 5 pmol of each primer, the four deoxynucleotide triphosphates at 0.5 mM each, and 0.4 units of Taq DNA polymerase (Stratagene, La Jolla, Calif.) in reaction buffer consisting of 50 mM Tris-HCl, pH 8.5, 20 mM KCl, 2.5 mM $MgCl_2$ and 0.5 μg/ml BSA. Thermocyeling was performed on samples contained in sealed glass capillary tubes inserted in an Idaho Technology air driven thermocycler for 30 cycles of denaturation (95° C., 5 s), annealing (55° C., 62° C., or 68° C., 1 s) and elongation (74° C., 30 s). Annealing temperatures 68° C. to 70° C. were used to provide Salmonella specific PCR amplification of an internal agfA fragment. The products of DNA amplification were separated by electrophoresis in 15% polyacrylamide gels and visualized by UV illumination following ethidium bromide staining.

Figures 9A, 9B:
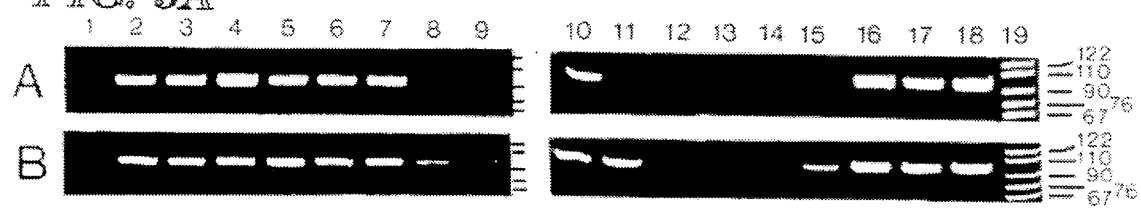
FIGS. 9A and 9B depict agarose gel electrophoresis of the results of PCR amplification of DNA fragments from various Enterobacteriaceae using oligonucleotide piers designed from the agfA gene of *S. enteritidis*. Lanes: 1, no DNA control; 2, *S. enteritidis* 27655-3b; 3, *S. typhimurium* SU453; 4, *S. infantis* S41-16; 5, *S. hadar* F9-1; 6, *S. agona*; 7, *S. newport;* 8, *E. coli* C600; 9, *E. coli* HB101; 10, *E. coli* NG7c; 11, *E. coli* Gambia 3; 12, *E. coli* Vietnam I/1; 13, *Enterobacter aerogenes*; 14, *Citrobacter freundii* 8090; 15, *Shigella sonnei*; 16, *S. choleraesuis*; 17, *S. typhi*; 18, *S. paratyphi* A subsp. *durazzo* ATCC 11511; 19, DNA fragment size markers prepared by MspI digestion of pBR322.

In a survey of Salmonella, including strains of *S. agona*, *S. choleraesuis*, *S. enteritidis* 27665-3b, *S. hadar* F9-1, *S. heidelberg* ATCC 8326, *S. infantis* S41-16, *S. newport*, *S. paratyphi* A ATCC 11511, *S. typhi* and *S. typhimurium* SU453, at an annealing temperature of 68° C., TAF5 and TAF6 allowed amplification of a agfA fragment of approximately 90 bp from all Salmonella serovars listed immediately above, consistent with the expected fragment size of 92 bp (FIG. 9). An approximately 90 bp DNA fragment was amplified efficiently from *E. coli* NG7c, and was inefficiently amplified from *E. coli* strains HB101, C600, Gambia 3 and Viet G as well as from a strain of *Shigella sonnei*. Under the same conditions, no amplification products were generated from *E. coli* clinical isolates 438Hf, B41-M, or Vietnam I/1 or from *Citrobacter freundii* 8090, *Enterobacter aerogenes*, *Erwinia caratovora*, *H. alvei*, *K. pneumoniae* 13883, *Proteus vulgaris*, *Serratia marcescens* or a *Providencia* sp. At an annealing temperature of 55° C., this set of primers allowed amplification of a fragment of approximately 90 bp from Salmonella spp., *E. coli* strains HB101, C600, 438Hf, B41-M, NG7c, Gambia 3, Vietnam F1 and Viet G and *Shigella sonnei*. No PCR fragments were generated from *C. freundii*, *Enterobacter aerogenes*, *Erwinia caratovora*, *H. alvei*, *K. pneumoniae* 13883, *Proteus vulgaris*, a *Providencia* sp., or *Serratia marcescens* at the lower annealing temperature.

Example 6

Sequencing of the tctCBA gene duster of *Salmonella typhimurium*

The tricarboxylic acid transport (tctI) operon of *Salmonella typhimurium* LT2 was isolated on an 8 kb EcoRI-BamHI fragment cloned into the vector pBR322 to create the recombinant plasmid pKW101 which conferred a citrate-utilizing ($cit^+$) phenotype on *E. coli* MC4100 (Widenhorn et al., "Cloning and promoters of the *Salmonella typhimurium* tricarboxylate transport operon in *Escherichia coli*," *J. Bacteriol.* 170:883–888, 1988). pKW101 was digested with the restriction enzymes KpnI and PstI to yield a fragment of 4.5 kb, containing the entire tctI operon, which was inserted into the M13 cloning vector M13mp18 (Yannisch-Perron et al., supra) to produce the recombinant clone KS1016. KS1016 was digested with the restriction enzymes EcoRI and HindIII (which cut only in the vector DNA) to release the tctI fragment for subcloning into the M13 cloning vector MWB2349 to produce MKS3. (Barnes et al., "Kilo-Sequencing: Creation of an Ordered Nest of Asymmetric Deletions Across a Large Target Sequence Carried on Phage M13," *Meth. Enz.* 101:98–122, 1983.)

To facilitate determining the DNA sequence of tctCBA, the 4.5 kb EcoRI-HindIII tctI fragment was subcloned from KS1016 into the M13 cloning vector MWB2341, whose multiple cloning site is oriented in the opposite direction relative to the binding site of the universal DNA sequencing primer. This resulted in the creation of MKS11.

The recombinant clones MKS3 and MKS3 were subjected to a procedure generating nested deletions (Dale et al., "A rapid single-stranded cloning strategy for producing a sequential series of overlapping clones for use in DNA sequencing: Application to sequencing the corn mitochondrial 18S rDNA," *Plasmid* 13:31–40, 1985). Briefly, single-stranded recombinant M13 DNA was isolated by standard procedures (Sambrook et al., supra). DNA was linearized by HindIII digestion following hybridization of the oligonucleotide WK-10, 5'-TGAATTAATTCCA CAAGCTTTTTTTTTT-3'; to MKS3 (SEQ ID No. 8) or WK-9, 5'-CGACGGCCAGTGCCAAGCTTTTTTTTT-3' to MKS11 (SEQ ID No. 9) to create a double stranded restriction endonuclease cleavage site in an otherwise single-stranded molecule.

The linearized DNA was subsequently degraded by the 3' to 5' exonuclease activity of T4 DNA polymerase. Samples were withdrawn at 15, 30, 45, 60, 75, 90 and 105 minutes. The polymerase was inactivated by treating the sample at 65° C. for 2 minutes and the samples stored on ice. By withdrawing samples at different times, populations of DNA fragments with differing degrees of deletion were created. All time-point samples were pooled and the DNA was treated with terminal transferase in the presence of ATP to create a polyA tail. The deleted DNA molecules were hybridized with oligonucleotide WK-10 by heating to 65° C. for 5 minutes, followed by slow cooling for 30 minutes, then ligated by T4 DNA ligase for 1 hour at 21° C. and overnight at 4° C. The ligated fragments were transformed into E. coli WB373 made competent by the procedure of Mandel (Mandel and Higa, "Calcium dependent bacteriophage DNA infection," J. Mol. Biol. 53: 159, 1970). Well-isolated M13 plaques were picked, and grown up overnight (Sambrook et al., supra) into 2X-YT broth. The size of each recombinant DNA molecule was estimated by agarose gel electrophoresis. From over 100 plaques analyzed, 35 recombinant phage representing deletions of 0.3–4.8 kb were selected for DNA sequence analysis.

DNA sequences were determined using standard modifications of the enzymatic dideoxy termination method of Sanger et al. (supra). To resolve the sequence of regions that proved difficult to determine by standard protocols, the sequencing reactions were performed using Sequenase (a chemically modified form of T7 DNA polymerase; US Biochemicals) and either deoxyinosine or 7-deazadeoxyguanosine in place of deoxyguanosine, or standard protocol sequencing reactions were analyzed by wedge-gel electrophoresis. Whereas, most sequencing reactions utilized the universal forward sequencing primer, specific internal primers were also used. The names and sequences of the internal primers used are: WWK-19 5'-GGGCGACTATCGCGTTA-3', WWK-20 5'-AGCCACTTGTAGCGGCC-3', WWK-21 5'-GGAAGTGCATTTTACGT-3', WWK-22 5'-CATGCTGCCAAGACAGG-3', WWK-23 5'-C TTTGGATCTGCCAGGC-3', WWK-24 5'-GCGCCGTCATGATCGCC-3' (SEQ ID Nos. 10, 11, 12, 13, 14, and 15, respectively). The sequences for tctA, tctB and tctC are shown in FIGS. 4A–4B, 5 and 6A–6B, respectively.

The sequences of tctA, tctB, and tctC were confirmed by automated DNA sequencing using an Applied Biosystems, Inc. Model 373A automated DNA sequencer and the reagents and protocols provided by the manufacturer for cycle-sequencing (Applied Biosystems, Inc., Foster City, Calif.). DNA oligonucleotide sequencing primers used for this purpose included:

5'TCGGGATGCTGTTCGGCG3' (SEQ. ID. No. 16)
5'CTGCCTGCGGAGTCGGC3' (SEQ. ID. No. 17)
5'GTCGCAAGGCCAAGACCG3' (SEQ. ID. No. 18)
5'GTGTATCGGCACCACCCTG3' (SEQ. ID. No. 19)
5'CCCGGCGATGTTCACCG3' (SEQ. ID. No. 20)
5'CCAATACCGCGCCGGAG3' (SEQ. ID. No. 21)
5'GCGGAGGCAATGATGAGCC3' (SEQ. ID. No. 22)
5'TGCCGCCATACTCACAGCC3' (SEQ. ID. No. 23)
5'TCTTGGCAGCATGATGGCG3' (SEQ. ID. No. 24)
5'CTGGCAATGGTCGCCCG3' (SEQ. ID. No. 25)
5'GCAATCAGCAGCGCAGC3' (SEQ. ID. No. 26)

Figure 12:
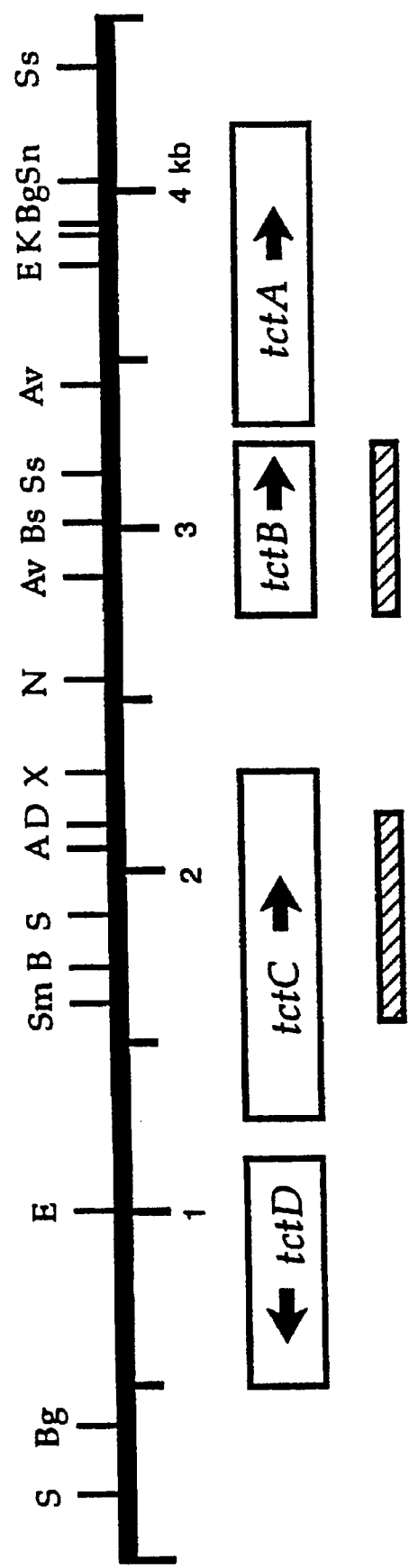
FIG. 12 depicts a restriction map of the region of the *S. typhimurium* chromosome encoding tctDCBA. The position and orientation of the open reading frames of tctD, tctC and tctB and the tctA open reading frame are indicated by the underlying boxes and arrows. Preferred regions of tctC and tctB useful as Salmonella DNA probes are indicated by the cross-hatched boxes. Abbreviations: A, ApaI; Av, AvaII; B, BglII; Bg, BglI; Bs, BstEII; D, DraI; E, EcoRV; K, KpnI; N, NcoI; S, SalI; Sm, SmaI; Sn, SnaBI; Ss, SspI; X, XmnI.
Figure 13:
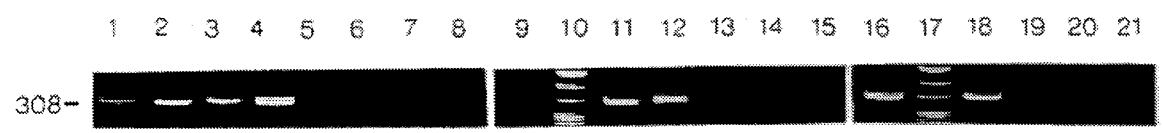
FIG. 13 depicts a PCR-mediated DNA amplification of 308-base tctC fragments, using primers TPP1 and TPP2, from representative Salmonella serovars and other Enterobacteriaceae. Lanes: 1, *S. enteritidis* 27655-3b; 2, *S. typhimurium* F18-1; 3, *S. infantis* S41-16; 4, *S. choleraesuis*; 5, *E. coli* C600; 6, *C. freundii* 8090; 7, *Shigella sonnei*; 8, no DNA (control); 9, *S. typhi*; 10 and 17, DNA fragment size markers of 217, 238, 242, 309, 404 and 527 bp prepared by MspI digestion of pBR322; 11, *S. paratyphi* A subsp. *durazzo* ATCC 11511; 12, *S. enteritidis* HWC989; 13, *Shigella dysenteriae* ATCC 29027; 14, *Shigella boydii* ATCC 8700; 15, *Shigella flexneri* ATCC 12022; 16, *S. berta* ATCC 8392; 18, *S. pullorum* ATCC 9120; 19, *Enterobacter aerogenes*; 20, *Klebsiella pneumoniae* 13883; 21, *Serratia marcescens*.

A restriction map prepared from the DNA sequence appears in FIG. 12. The Figure shows the positions of endonuclease cleavage sites for ApaI, AvaII, BglII, BglI, BstII, DraI, EcoRV, KpnI, NcoI, SalI, SmaI, SnaBI, SspI and XmnI relative to the open reading frames of tctC, tctB and tctC.

DNA sequences encoding the TctC protein were recognized by comparison to the complete sequence of TctC protein; the predicted amino acid sequence agreed with the amino acid sequence determined by peptide sequencing studies on the purified protein. The predicted size of the TctB protein based on the nucleotide sequence agreed with the size of an expressed protein as determined by SDS-PAGE.

Example 7 tctC- and tctB-based diagnostic probes for Salmonella spp.

Two fragments of the tctI operon were applied as diagnostic probes for Salmonella. One was composed of a fragment encoding the entire tctB gene. This probe was generated by PCR amplification using primers (TTB-1, 5'-ATGGATACCTGGATATATCTTTCTCAGGG'-3' (SEQ ID No. 27); TTB-2, 5'-TATTTATTTAAGCCGGGTTT-3' (SEQ ID No. 28)) that are respectively complementary to the 5' and 3' termini of the tctB gene, as depicted in FIG. 5. The second is 591 base pair fragment of tctC generated by the digestion of the recombinant plasmid pKW132 with the restriction enzymes SmaI and DraI. This digestion produces a fragment from nucleotides 1553 to 2144 of the tctC gene (see Example 6).

These fragments corresponding to tctB and tctC were used to screen the dot-blots and HGMF panels of the bacterial strains tested in Example III following random primer labeling with [α-$^{32}$P]dATP and incubation at room temperature for 3 h. The DNA blots were prehybridized in buffer (Sambrook et al. supra) containing 20 µg/ml herring sperm DNA at 65° C., and then hybridized to one or the other of the diagnostic probes at 65° C. The blots were then washed under high stringency using 0.2×SSPE–0.1% SDS at 65° C. prior to detection of hybridization by autoradiography on X-OMAT AR5 film.

The tctB probe detected 609 out of 612 Salmonella isolates (99.5%). As shown in Table 2, of the 252 other Enterobacteriaceae tested with tctB, the positively hybridizing strains included 10 of 13 Citrobacter spp. 11 of 17 Enterobacter spp. and 2 of 6 Serratia spp. The tctC probe detected 609 out of 612 (99.5%). The tctC probe did not detect any of the 250 non-Salmonella Enterobacteriaceae tested. Neither the tctB nor tctC probes detected any of the non-*Enterobacteriaceae eubacteria* that were tested.

TABLE 2

Hybridization of tctB and tctC probes to Salmonella and related bacteria

| Bacteria | Source(s)[a] | O-Serogroup | Hybridization of bacterial DNA to[b] | |
|---|---|---|---|---|
| | | | tctB PCR fragment | tctC restr. fragment |
| *Salmonella serovars* | | | | |
| S. agona | AGG MRD TJT | B | 13/13 | 13/13 |
| S. alachua | MRD | O | 1/1 | 1/1 |
| S. albany | MRD TJT | C3 | 7/7 | 7/7 |
| S. anatum | AGG MRD UVIC | E1 | 15/15 | 15/15 |
| S. arizonae | MRD TJT | | 5/5 | 5/5 |
| S. arkansas | AGG MRD | E1 | 4/4 | 4/4 |
| S. bardo | MRD | C3 | 1/1 | 1/1 |
| S. barielly | MRD | C1 | 12/12 | 12/12 |
| S. berta | ATCC PVL HPB | D1 | 7/7 | 7/7 |
| S. binza | AGG HPB | E2 | 6/6 | 6/6 |
| S. blockley | HPB MRD | C2 | 5/5 | 5/5 |
| S. braenderup | HPB | C1 | 5/5 | 5/5 |
| S. brandenburg | AGG MRD | B | 3/3 | 3/3 |
| S. bredeney | AGG MRD | B | 8/8 | 8/8 |
| S. brunei | MRD | C3 | 1/1 | 1/1 |
| S. california | MRD | B | 2/2 | 2/2 |
| S. cerro | AGG HPB MRD TJT | K | 8/8 | 7/8 |
| S. chester | MRD | B | 1/1 | 1/1 |
| S. choleraesuis | AGG BBF | C1 | 2/2 | 2/2 |
| S. colindale | MRD | C1 | 1/1 | 1/1 |
| S. cubana | MRD TJT | G2 | 2/2 | 2/2 |
| S. dahomey | TJT | X | 1/1 | 1/1 |
| S. derby | AGG MRD | B | 3/3 | 3/3 |
| S. drypool | MRD UVIC | E2 | 2/2 | 2/2 |
| S. dublin | AGG ATCC PVL | D1 | 1/1 | 1/1 |
| S. ealing | HPB | O | 1/1 | 1/1 |
| S. eastbourne | MRD UVIC | D1 | 3/3 | 3/3 |
| S. eimsbuettel | MRD HPB | C4 | 2/2 | 2/2 |
| S. elisabethville | HPB | E1 | 1/1 | 1/1 |
| S. enteritidis | AGG ATCC HPB JT MRD PVL TW | D1 | 24/24 | 24/24 |
| S. flint | MRD | Z | 1/1 | 1/1 |
| S. florida | TJT | H | 1/1 | 1/1 |
| S. gallinarum | ATCC AGG | D1 | 1/2 | 1/2 |
| S. gaminara | TJT | I | 1/1 | 1/1 |
| S. give | MRD | E1 | 1/1 | 1/1 |
| S. godesberg | NRC | N | 1/1 | 1/1 |
| S. good | MRD | L | 1/1 | 1/1 |
| S. haardt | HPB MRD | C3 | 9/9 | 9/9 |
| S. hadar | HPB TJT | C2 | 56/56 | 56/56 |
| S. halmstad | MRD | E2 | 1/1 | 1/1 |
| S. hamburg | TJT | B | 1/1 | 1/1 |
| S. havana | AGG HPB MRD TJT | G2 | 5/6 | 6/6 |
| S. heidelberg | AGG ATCC HPB MRD | B | 26/26 | 26/26 |
| S. indiana | AGG HPB MRD | B | 10/10 | 10/10 |
| S. infantis | AGG HPB MRD TJT | C1 | 26/26 | 26/26 |
| S. isangi | MRD | C1 | 1/1 | 1/1 |
| S. javiana | ATCC MRD | D1 | 1/1 | 1/1 |
| S. johannesburg | AGG HPB MRD | R | 22/22 | 22/22 |
| S. kentucky | HPB MRD | C1 | 11/11 | 11/11 |
| S. landau | NRC | N | 1/1 | 1/1 |
| S. lexington | HPB | E1 | 1/1 | 1/1 |
| S. lille | HPB | C1 | 2/2 | 2/2 |
| S. litchfield | MRD | C2 | 1/1 | 1/1 |
| S. livingstone | HPB MRD | C1 | 7/7 | 7/7 |
| S. london | AGG HPB MRD | E1 | 4/4 | 4/4 |
| S. manhatten | HPB TJT | C2 | 1/1 | 1/1 |
| S. mbandaka | HPB MRD TJT | C1 | 27/27 | 27/27 |
| S. meleagridis | HPB MRD | E1 | 2/2 | 2/2 |
| S. minnesota | HPB NRC TJT | L | 3/3 | 3/3 |
| S. montevideo | HPB MRD | C1 | 14/14 | 14/14 |
| S. muenchen | HPB TJT | C2 | 1/1 | 1/1 |
| S. muenster | AGG MRD | E1 | 6/6 | 6/6 |
| S. newbrunswick | HPB | E2 | 2/2 | 2/2 |
| S. newington | AGG HPB MRD | E2 | 12/13 | 13/13 |
| S. newport | HPB MRD TJT | C2 | 6/6 | 6/6 |
| S. nienstedten | HPB TJT | C4 | 2/2 | 2/2 |
| S. ohio | HPB | C1 | 11/11 | 11/11 |
| S. oranienberg | ATCC HPB MRD | C1 | 6/6 | 6/6 |
| S. orion | HPB | E1 | 2/2 | 2/2 |
| S. panama | HPB MRD | D1 | 2/2 | 2/2 |

TABLE 2-continued

Hybridization of tctB and tctC probes to Salmonella and related bacteria

| Bacteria | Source(s)[a] | O-Serogroup | Hybridization of bacterial DNA to[b] | |
|---|---|---|---|---|
| | | | tctB PCR fragment | tctC restr. fragment |
| S. paratyphi A | ATCC | A | 1/1 | 1/1 |
| S. paratyphi B | MRD TJT | B | 3/3 | 3/3 |
| S. poona | AGG HPB | G1 | 2/2 | 2/2 |
| S. pullorum | ATCC PVL AGG | D1 | 7/7 | 7/7 |
| S. reading | AGG MRD | B | 2/2 | 2/2 |
| S. saint-paul | AGG HPB MRD TJT | B | 7/7 | 7/7 |
| S. sandiego | MRD TJT | B | 1/1 | 1/1 |
| S. schwarzengrund | AGG HPB MRD TJT | B | 18/18 | 18/18 |
| S. senftenberg | AGG HPB MRD | E4 | 28/28 | 28/28 |
| S. stanley | TJT | B | 1/1 | 1/1 |
| S. taksony | MRD | E4 | 1/1 | 1/1 |
| S. tennessee | FDA HPB MRD TJT | C1 | 15/15 | 15/15 |
| S. thomasville | AGG | E3 | 3/3 | 3/3 |
| S. thompson | HPB MRD | C1 | 18/18 | 18/18 |
| S. typhi | MRD | D1 | 2/2 | 2/2 |
| S. typhimurium | AGG ATCC HPB JT MRD TJT | B | 40/40 | 40/40 |
| S. urbana | NRC | N | 1/1 | 1/1 |
| S. wassenaar | MRD | Z | 1/1 | 1/1 |
| S. weltevreden | MRD | E1 | 1/1 | 1/1 |
| S. westhampton | HPB | E1 | 1/1 | 1/1 |
| S. worthington | AGG HPB TJT | G2 | 7/7 | 5/7 |
| Salmonella spp. | HPB | | 7/7 | 7/7 |
| Other Enterobacteriaceae | | | | |
| Citrobacter freundii | AGG ATCC MRD UVIC | | 9/12 | 0/12 |
| Citrobacter sp. | NRC | | 1/1 | 0/1 |
| Enterobacter aerogenes | ATCC NRC UVIC | | 3/3 | 0/3 |
| Enterobacter agglomerans | AGG MRD | | 1/6 | 0/6 |
| Enterobacter cloacae | AGG ATCC MRD NRC | | 7/8 | 0/8 |
| Erwinia caratovora | NRC UVIC | | 0/3 | 0/3 |
| Escherichia coli | ATCC CDC FOD LCDC LE MRD NRC TJT UG UT UVIC | | 0/121 | 0/121 |
| Hafnia alvei | MRD NRC UVIC | | 0/6 | 0/6 |
| Klebsiella oxytoca | NRC | | 0/1 | 0/1 |
| Klebsiella pneumoniae | AGG ATCC MRD NRC | | 0/7 | 0/7 |
| Proteus mirabilis | MRD | | 0/4 | |
| Proteus morganii | AGG | | 0/1 | 0/1 |
| Proteus rettgeri | MRD UVIC | | 0/4 | 0/4 |
| Proteus vulgaris | AGG MRD NRC UVIC | | 0/6 | 0/6 |
| Proteus sp. | MRD | | 0/1 | 0/1 |
| Providencia alcalifaciens | HPB | | 0/1 | 0/1 |
| Providencia rettgeri | UVIC | | 0/1 | 0/1 |
| Providencia spp. | MRD UVIC | | 0/2 | 0/2 |
| Serratia fonticola | MRD | | 0/1 | 0/1 |
| Serratia marcescens | MRD UVIC | | 2/5 | 0/5 |
| Shigella boydii | MRD | | 0/2 | 0/2 |
| Shigella dysenteriae | MRD | | 0/3 | 0/3 |
| Shigella flexneri | MRD | | 0/14 | 0/14 |
| Shigella sonnei | MRD UVIC | | 0/5 | 0/5 |
| Yersinia enterocolitica | AGG LCDC MRD | | 0/27 | 0/27 |
| Yersinia frederiksenii | MRD | | 0/1 | 0/1 |
| Yersinia intermedia | MRD | | 0/3 | 0/3 |
| Yersinia pseudotuberculosis | MRD | | 0/1 | 0/1 |
| Other eubacteria | | | | |
| Achromobacter xylosoxidans | NRC | | 0/1 | 0/1 |
| Achromobacter sp. | MRD | | 0/1 | 0/1 |
| Acinetobacter calcoaceticus | ATCC MRD | | 0/2 | 0/2 |
| Aeromonas hydrophila | MRD NRC TJT | | 0/5 | 0/5 |
| Aeromonas salmonicida | WWK | | 0/1 | 0/1 |
| Alcaligenes faecalis | NRC | | 0/2 | 0/2 |
| Bacillus subtilis | UVIC | | 0/1 | 0/1 |
| Bordetella bronchiseptica | MRD | | 0/1 | 0/1 |
| Pseudomonas aeruginosa | ATCC MRD NRC UVIC | | 0/1 | 0/1 |
| Pseudomonas dimuta | MRD | | 0/1 | 0/1 |
| Pseudomonas fluorescens | NRC | | 0/2 | 0/2 |
| Pseudomonas putida | NRC | | 0/2 | 0/2 |
| Pseudomonas stutzeri | MRD | | 0/1 | 0/1 |
| Pseudomonas sp. | AGG | | 0/1 | 0/1 |

TABLE 2-continued

Hybridization of tctB and tctC probes to Salmonella and related bacteria

| | | | Hybridization of bacterial DNA to[b] | |
|---|---|---|---|---|
| Bacteria | Source(s)[a] | O-Serogroup | tctB PCR fragment | tctC restr. fragment |

[a]Abbreviations of source names: AGG, Agriculture Canada Research Station, Guelph, Ontario; ATCC, American Type Culture Collection; BBF, B. B. Finlay, Biotechnology Laboratory and Departments of Biochemistry and Microbiology, University of British Columbia, Vancouver, Canada; CDC, Centers for Disease Control, Atlanta, Georgia; FDA, U.S. Food and Drug Administration, Washington, D.C.; GS, G. Sarlós, University Medical School, Institute of Microbiology, Pécs, Hungary; HPB, Health Protection Branch of Health and Welfare Canada, Ottawa; JT, J. Tomas, Departement Microbiologie, Universitat de Barcelona, Spain; LCDC, H. Lior, National Enteric Reference Center of the Laboratory Centre for Disease Control, Ottawa, Canada; LE, L. Emödy, University Medical School, Institute of Microbiology, Pécs, Hungary; MRD, Microbiological Research Division of Health and Welfare Canada, Ottawa; NRC, National Research Council, Ottawa, Ontario; PVL, G. Thiele, Provincial Veterinary Laboratory of British Columbia, Abbotsford, Canada; TJT, T. J. Trust, Department of Biochemistry and Microbiology, University of Victoria, Canada; TW, T. Wadström, University of Lund, Sweden; UG, University of Guelph, Guelph, Ontario; University of Toronto, Toronto, Ontario; UVIC, Culture Collection of the Department of Biochemistry and Microbiology, University of Victoria, Canada; WWK, W. W. Kay, Department of Biochemistry and Microbiology, University of Victoria, Canada.
[b]Hybridization of 509 bp PCR fragment encompassing tctB or a 591 bpSmaI-DraI restriction fragment derived from tctC to dot blots of purified DNA or colony blots on HGMF panels are reported as the number of positively hybridizing strains per total number of strains tested. Strains obtained from BBF, PVL, TJT, UVIC and WWK were screened by dot blot hybridization using 0.5 µg DNA samples bound to Hybond-N+ membranes (Amersham Canada Ltd., Oakville, ON) as described by Doran et al., J. Clin. Microbiol. 31:2263–2273, 1993). Other strains were assembled on HGMF membranes and screened by colony blotting as previously described (Peterkin et al., Food Microbiol. 6:281–284, 1989). Hybridization of samples of membrane-bound bacterial DNA to the probe. The results of hybridization to dot blots of purified DNA are reported as positive '+', negative '−'. Hybridization of the probe to DNA samples represented as colony blots on HGMF (HPB) panels are reported as the number of positively hybridizing strains per total number of strains tested or 'nd', not determined.

Example 8 tctC-based PCR assays targeting Salmonella

Oligonucleotides TTC1, 5'-GGGACTGTGGTCGCCTTTTCCG G 3' (SEQ ID No. 29) and TTC2, 5'-CCGCCCTCAAAGGCA ACGTAGCGC 3' (SEQ ID No. 30), were designed to allow an amplification of an approximately 180 bp DNA fragment specifically from Salmonella bacteria. Bacterial DNA samples for PCR reactions were prepared from cells (20 µg wet weight) resuspended in 1 ml of distilled, deionized $H_2O$ and lysed by boiling for 5 min. Cell lysates containing DNA were clarified by centrifugation (16,000×g, 5 min, 25° C. and stored at −20° C.).

Amplification was carded out in a 10 µl reaction volume containing 1 µl of heat-denatured bacterial DNA solution, 5 pmol of each primer, the four deoxynucleotide triphosphates at 0.5 mM each, and 0.4 units of Taq DNA polymerase (Stratagene, La Jolla, Calif.) in reaction buffer consisting of 50 mM Tris-HCl, pH 8.5, 20 mM KCl, 2.5 mM $MgCl_2$ and 0.5 mg/ml BSA. Thermocycling was performed on samples contained in sealed glass capillary tubes inserted in an Idaho Technology air driven thermocycler for 30 cycles of denaturation (95° C., 1 s), annealing (63° C.–70° C., 1 s) and elongation (74° C., 30 s). The products of DNA amplification were separated by electrophoresis in 15% polyacrylamide gels and visualized by UV illumination following ethidium bromide staining.

A 308 bp fragment of the tctC gene was amplified from S. arizonae, S. berta, S. choleraesuis, S. enteritidis, S. gallinarum, S. heidelberg, S. infantis, S. paratyphi A, S. paratyphi B, S. pullorum, and S. typhimurium but not from S. typhi. No PCR fragments were generated from E. coli, Proteus vulgaris, and Shigella spp. that do not utilize citrate or from K. pneumoniae, Providencia rettgeri and Serratia marcescens that do grow on citrate. Weak amplification of a 308 bp fragment was observed for titrate-utilizing species C. freundii and Enterobacter aerogenes when PCR was conducted at a magnesium concentration from 1.5 to 15 mM. This band was eliminated when concentrations were greater than 18 mM.

No tctC fragment was amplified from S. typhi, only the Salmonella serovar tested that does not utilize citrate, although sequences homologous to tctC and tctB were detected by hybridization.

Example 9

Sequencing and characterization of sefU₂U₁ABCD from the sef gene cluster of Salmonella enteritidis A 5.3 kb HindIII fragment carrying the SEF14 fimbrin structural gene and part of the sef gene cluster was subcloned from cos48, a recombinant cosmid carrying 44 kb of S. enteritidis chromosomal DNA, into pTZ19R to generate pKX1 (Feutder et al., "Cloning and expression of a Salmonella enteritidis fimbrin gene in Escherichia coli," J. Bacteriol. 170:4216–4222, 1988; Müller et al., "Fimbriation genes of Salmonella enteritidis," J. Bacteriol. 171:4648–4654, 1989). A series of overlapping deletion subclones of pKX1 (DpKX1) were generated using pKX1 linearized with EcoRI and varying degrees of DNAse I digestion according to the method of Lin et al. ("An improved DNA sequencing strategy," Anal. Biochem. 147:114–119, 1985), to create a collection of 50 nested deletions. The resulting linear DpKX1 subclones were treated with the Klenow fragment of DNA polymerase I and then blunt end ligated with T4 DNA ligase to recircularize the plasmids. The various DpKX1 were transformed into E. coli XL-1 Blue (Stratagene, La Jolla, Calif.) using standard procedures (Sambrook et al., supra). The DpKX1 were purified by standard alkaline lysis procedures (Sambrook et al., supra) and run on a 1% agarose gel. A series of DpKX1 subclones separated by about 200 to 400 bp in size were chosen and named delA10, delB15, delB23, delC1, delD5, delD8, delD9, delD16, delD19, delE1, and delE21. Large amounts of these plasmids were purified by alkaline lysis for DNA sequencing.

The ΔpKX1 subclones were sequenced by the dideoxynueleotide chain termination method (Sanger et al., "DNA sequencing with chain terminating inhibitors," Proc. Natl. Acad Sci. USA 74:5463–5467, 1977) using T7 DNA polymerase (T7 DNA Polymerase Sequencing Core System, Deaza kit, Promega, Madison, Wis.) and deoxyadenosine 5'-[$\alpha^{35}$S] triphosphate (New England Nuclear, Markham, ON) according to the manufacturers' specifications.

The result of DNA sequencing reactions were electrophoresed through a 6% polyacrylamide gel (45 W, 55° C.–60° C.) using a discontinuous buffer system (Carninci et al., "A simple discontinuous buffer system for increased resolution and speed in gel electrophoretic analysis of DNA sequence," Nucleic Acid Res. 18:204, 1989). Following electrophoresis, the gels were fixed in a solution of 12% methanol and 10% acetic acid for 15 min, and dried onto 3MM paper (Whatman Intl. Ltd., Maidstone, England) under vacuum at 80° C. for 2 hours on a Savant gel drying apparatus (Savant Instruments Inc., Farmingdale, N.Y.). Dried gels were exposed to X-Omat K XK-1 film (Kodak, Rochester, N.Y.) and the sequence read directly from the developed films. Both DNA strands were fully sequenced, using the 17 bp reverse palmer for the coding strand (GTCATAGCTGTTTCCCG) (SEQ ID No. 31) and 12 custom made internal oligonucleotide primers (ULTRA Diagnostics Corporation, Seattle, Wash.) for the opposite strand. The sefA, sefB, sefC and sefD sequences are depicted in FIGS. 2A–2D.

The genes for sefU$_1$ and sefU$_2$ were similarly sequenced on overlapping subclones and these sequences are depicted in FIGS. 3A–3B.

The programs contained in MacVector (Intelligenetics, Mountain View, Calif.) were used to determine the order of the overlapping DNA sequences. DNA Strider™ version 1.1 was used to identify the open reading frames for sefA, sefB and sefC, which were predicted to encode polypeptides of 14,436M$_r$, 28,012M$_r$ and 90,268 M$_r$, respectively. The open reading frames for sefU$_1$ and sefU$_2$ and sefD were similarly recognized. The predicted amino acid sequences of the SefA, SerB and SefC proteins were compared to proteins listed in the GenBank (release #66.0), SWISS-PROT (release #16.0), and GENPEPT (release #64.3) data bases and the MACAW program (NCBI, Bethesda, Md.) to align regions of local similarity among proteins exhibiting similarity.

Computer analysis showed that the gene sefA encodes a novel protein whose predicted M$_r$ and amino acid composition match those reported previously by us for the SEF14 fimbrin (Feutder et al. 1986, supra). Moreover, the first 60 predicted amino acids are identical to the N-terminal amino acid sequence reported for the SEF14 fimbrin (Feutrier et al. 1986, supra). These results demonstrate that sefA encodes the structural subunit of SEF14 fimbriae, SefA.

The adjacent downstream gene, sefB, encodes a fimbrial periplasmic chaperone protein.

sefC, the gene immediately downstream of sefB, encodes a fimbrial outer membrane protein that contains nine putative membrane-spanning domains. Upstream open reading frames, sef$_1$ and sefU$_2$, are of unknown function.

The nucleotide sequence of DNA immediately downstream of sefABC revealed a fourth open reading frame (ORF) designated sefD. This gene had the same translational polarity as sefABC (FIG. 1). In fact, the AUG start codon for sefD overlapped the UGA stop codon of sefC. The gene organization of the gene cluster, has been confirmed on the chromosome by Southern blot analysis of KpnI digested S. enteritidis 3b chromosomal DNA hybridized with sefA and sefD specific probes. Preceding the sefD ORF by 8 bp was a consensus Shine-Dalgarno sequence for translation initiation (GGAG). The sefD ORF was 447 bp and the predicted molecular weight of the encoded protein, designated SefD, was 16,722 Daltons.

The predicted amino acid sequence of sefD had a putative signal peptidase cleavage site between Ser-24 and Ser-25 as determined by the method of von Heijne (1984). The presence of a putative leader sequence suggested that the protein was exported from the cytoplasm to either the periplasmic space or the outer membrane.

To confirm that sefABC encoded proteins of the predicted sizes, proteins were translated in vitro from pKX1. The plasmid-encoded proteins were labeled with [$^{35}$S]-methionine using a cell-free coupled transcription-translation system (Prokaryotic DNA-Directed Transcription-Translation System Kit, Amersham, Oakville, ON) according to the manufacturers' instructions.

Figure 11A:
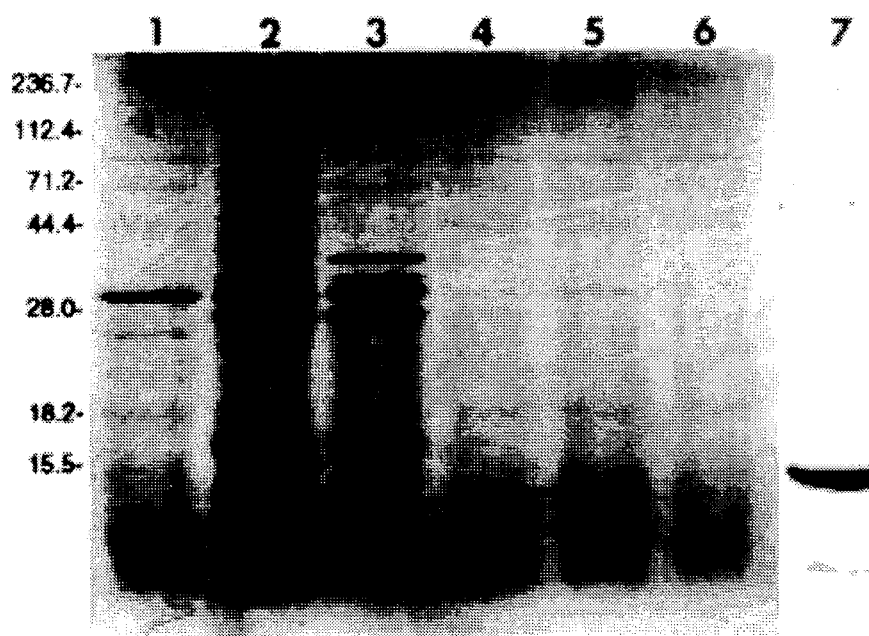
FIG. 11A depicts an autoradiograph of the results of expression of the sefA, sefB and sefC genes in an *E. coli* in vitro transcription-translation system. Lane 1, pTZ19; Lane 2, pKX1; Lane 3, pSC1; Lane 4, delB15; Lane 5, delB23; Lane 6, delD10 Lane 7, Western blot of the in vitro transcription-translation of pKX1 developed using antisera generated against denatured SEF14 fimbrin. The size of the molecular weight markers is indicated on the left (10$^3$ M$_r$).
Figure 11B:
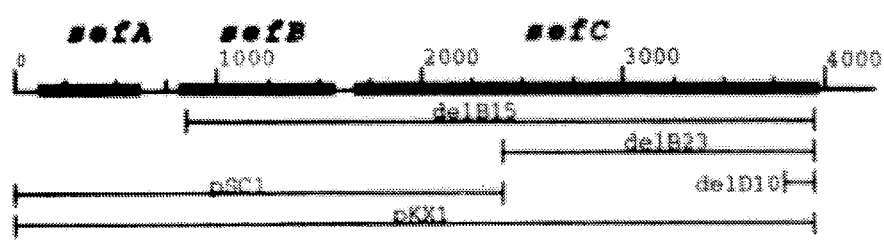
FIG. 11B is a schematic representation of the sef gene cluster showing the inserts of various deletion subclones used in the in vitro transcription-translation experiments.

Plasmids carrying either the 5.3 kb fragment of the sef operon or deletions thereof (delB15, delB23, delD10) were used as DNA templates (FIG. 11B). Plasmids purified by alkaline lysis (Sambrook et al., supra) were incubated with the other reaction components in a final reaction volume of 30 µl and incubated at 37° C. for 30 min. Unlabeled methionine (5 µl) was added, the mixture was incubated a further 5 min and then the reaction was terminated by placing the reactions at 0° C. Ten µl of the reaction mixture was added to 2×Laemmli sample buffer (Laemmli, "Cleavage of structural proteins during the assembly of the head of bacteriophage T4," Nature 227:680–685, 1970) and then subjected to microdialysis (Marusyk and Sergent, "A simple method of dialysis of small volume samples," Anal. Biochem. 105:403–404, 1989) on Millipore filters (Millipore Corp., Bedford, Mass.) for 10 to 15 min prior to SDS-PAGE analysis on 12% gels poured with a 5% stacking gel (Laemmli, supra). The acrylamide gel was fixed for 30 min in 7% acetic acid, dried onto 3 MM paper for 1 hour at 80° C. and then exposed to X-Omat-AR5 film (Kodak, Rochester, N.Y.) to visualize the labeled proteins.

Several translation products were identified (FIG. 11A, lane 2). The 14KM$_r$ protein was identified on Western blots as SefA (FIG. 11A, lane 7). The 90K M$_r$ protein was identified as SefC. The 27K M$_r$ protein was identified as SefB. The 70K, 44K and 40K M$_r$ bands were likely minor degradation products of SefC because these bands were absent when pSC1, which contained a deletion in sefC, was used as the template (FIG. 11A, lanes 2 and 3). The 16K M$_r$ band seemed to be a minor degradation product of SefB as this band remained when pSC1 was used as a template (FIG. 11A, lanes 2, 3). When the three DNaseI deletion subclones, delB15, delB23 and delD10, were each used as templates, the bands for SefB, SefC and their minor degradation products were absent (FIG. 11A, lanes 4–6) indicating sefA and/or its upstream region is necessary for the expression of sefB and sefC, as was predicted from the DNA sequence analysis (FIGS. 1, 2).

To confirm that translation of SefB and SefC was dependent on the presence of sefA and/or the region upstream of sefA, the transcription start sites for sefA, sefB and sefC were determined. Primer extension studies consistently revealed transcription start sites immediately upstream of sefA. These included two major extension products as well as several minor ones (FIG. 11-3). When the primer extension reaction was performed at 50° C., a temperature expected to destabilize secondary structures, reverse transcriptase still stopped at all the sites with the same frequency suggesting that stem-loop structures were not blocking the migration of reverse transcriptase. No transcription start sites could be found immediately upstream of sefB or sefC. These results indicated that the 5' end of the mRNA transcript of sefABC was initiated upstream of sefA.

Example 10

SefD-based diagnostic probes for Salmonella spp.

Figures 14A, 14B:
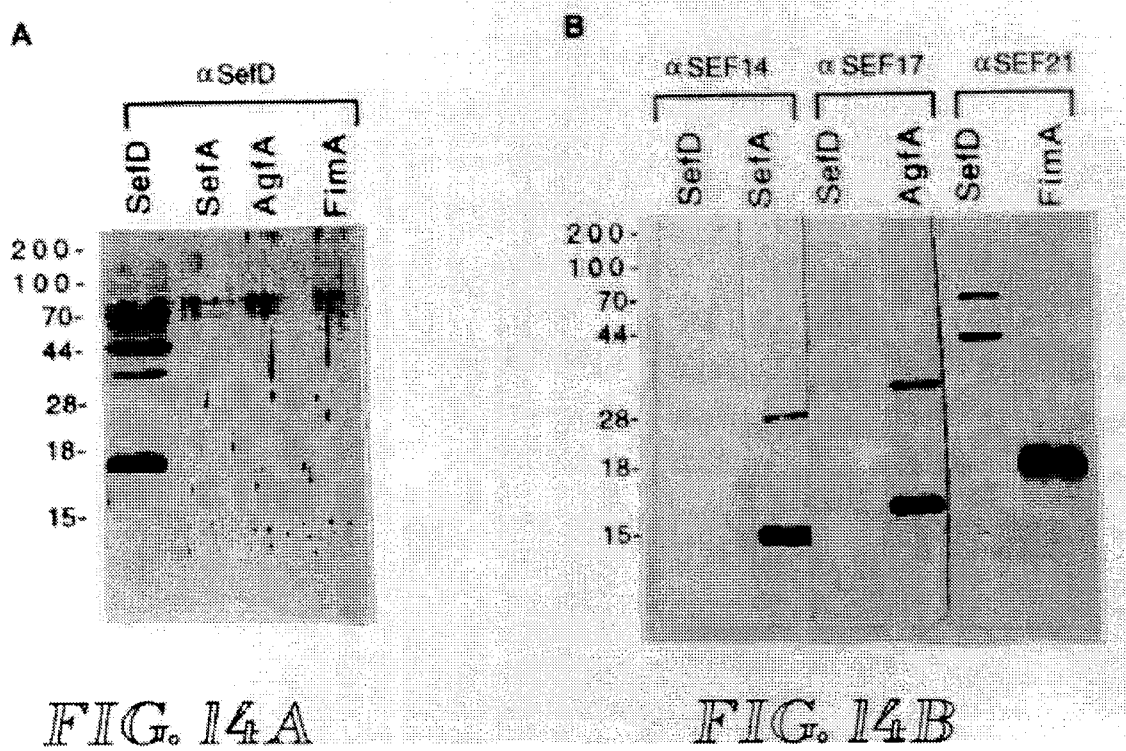
FIG. 14 depicts an analysis of the serological cross-reactivity between the four fimbfiae of *S. enteritidis* 3b and their antisera. Panel A depicts a Western blot analysis of Factor Xa cut MalE+SefD fusion (lane 1), purified SEF14 (lane 2), SEF17 (lane 3) and SEF21 (lane 4) with anti-SefD antiserum. Panel B depicts a western blot analysis of SefD with SEF14 (lanes 1 and 2), SEF17 (lanes 3 and 4) or SEF21 (lanes 5 and 6) antisera. SefA, Agfa and FimA are the subunits of SEF14, SEF17 and SEF21 fimbriae, respectively. In both panels A and B, the size (kDA) of the molecular weight markers is indicated on the left.

SefD was expressed as a MalE'-SefD fusion protein (New England Biolabs, Beverly, Mass.). Purified SefD, obtained by cleaving the fusion protein and eluting SefD from SDS polyacrylamide gels, was used to raise polyclonal antisera. Western blot analysis of SefD production in S. enteritidis revealed that the protein migrated at approximately 18,000 M$_r$ and that the protein was expressed in large quantities. This result suggested that SefD was a structural protein. Since S. enteritidis produces three other known fimbriae, SEF14, SEF17 and SEF21, further Western blot studies were performed to determine if SefD was serologically distinct from the fimbrins of these other fimbriae. Western blot analysis revealed that the purified fimbriae SEF14, SEF17, and SEF 21 did not react with polyclonal antisera raised to SefD (FIG. 14). Similarly, purified SefD did not react with immune sera raised against purified SEF14 (SefA), SEF17 (AgfA), or SEF21 (FimA). In lane 1 of FIG. 14, two high MW bands were detected in addition to the expected 18 kDa band. The anti-SefD antisera was generated using the purified 18 kDa, Factor Xa cleavage product which consisted of SefD plus 4 amino acid residues from MalE' (44 kDa) and the uncleaved MalE'-SefD fusion (70 kDa). In FIG. 14, the lanes labeled SefD contained Factor Xa cleaved MalE'-SefD. In lane 5, two bands were present due to cross-reactivity of anti-SEF21 with MalE' (44 kDa) released by the Factor Xa cleavage and with the MalE' in the fusion protein (70 kDa) that was not completely cleaved with Factor Xa. Anti-SEF21 did not cross react with SefD since an 18 kDa band was not detected.

SefD was localized to the outer cell surface by immunogold electron microscopy using polyclonal immune sera raised to affinity purified, recombinant SefD. These studies revealed filamentous, immunogold-labeled structures resembling fimbriae on the surface of S. enteritidis 3b cells. Thus, SefD was concluded to be the major subunit of these fimbriae-like structures designated SEF18 (S. enteritidis fimbriae-like proteins composed of 18,000 $M_r$ subunits). Interestingly, SEF18 was often concentrated at the junction of two adjacent cells or found between cells. Thus, SefD is serologically distinct from SefA, AgfA, and FimA and morphologically distinct from SEF14, SEF17, and SEF21. Furthermore, the SEF14 gene cluster encodes two unique fimbrin-like proteins which are assembled into two distinct cell surface structures, SEF14 and SEF18.

PCR amplified sefD gene was hybridized to DNA from a total of 73 bacterial strains represented as DNA dot blots on nylon membranes under high stringency conditions (Table 3). The sefD gene probe hybridized to all members of the family Enterobacteriaceae tested with the exception of Serratia marcescens. Strong hybridization signals were obtained with DNA isolated from S. enteritidis, S. dublin, S. pullorum, S. gallinarum, and S. berta, as well as with DNA from Klebsiella pneumoniae and Shigella sonnei. DNA isolated from various E. coli strains and the other Salmonella species hybridized to the sefD probe with moderate intensity whereas DNA isolated from Enterobacter, Citrobacter, Erwinia, Hafnia, Providencia, Proteus and Shigella sonnei hybridized weakly to the sefD probe. DNA preparations from strains of other eubacteria did not hybridize to the sefD probe (Table 3). Proteus vulgaris and Providencia rettgeri produced an immunologically cross-reactive band that migrated with an apparent MW of 17,000. Those strains negative for sefD by DNA dot blot analysis were also negative for SefD production as determined by Western blot analysis (Table 3). Subsequent immunogold EM studies indicated that SEF18 fimbriae-like structures were also produced on the surface of E. coli. The apparent morphology and distribution of the immunogold labeled structures on these strains varied from filamentous structures of variable length radiating from the cell to amorphous structures. These structures lacked the uniform length and rigid, channeled morphology of Type 1 fimbriae.

TABLE 3

The distribution of sefD and SefD among Salmonella isolates and other eubacteria

| Bacterial Species | Strains | Source[a] | Serogroup | SefD cross-reactive protein[b] | Hybridization[c] to sefD probe |
|---|---|---|---|---|---|
| Salmonella spp. | | | | | |
| S. albany | | TJT | C3 | + | ++ |
| S. anatum | | UVic | E1 | nt | ++ |
| S. arizonae | | TJT | | + | ++ |
| S. berta | 8392 | ATCC | D1 | + | ++ |
| | 89-4065 | PVL | D1 | nt | +++ |
| | 90-1271 | PVL | D1 | nt | +++ |
| S. bovis-morbificans | | TJT | C2 | + | ++ |
| S. cerro | | TJT | K | + | ++ |
| S. choleraesuis | | BBF | C1 | + | ++ |
| S. dahomey | | TJT | X | + | ++ |
| S. drypool | | UVic | E2 | + | ++ |
| S. dublin | 15480 | ATCC | D1 | + | +++ |
| | 89-3320 | PVL | D1 | nt | +++ |
| | 89-3349 | PVL | D1 | nt | +++ |
| | 89-4189 | PVL | D1 | nt | +++ |
| | 90-243 | PVL | D1 | nt | +++ |
| | 90-1176 | PVL | D1 | nt | +++ |
| S. eastbourne | | UVic | D1 | + | ++ |
| S. enteritidis | 27655-3b | TW | D1 | + | +++ |
| | 27655-3a | TW | D1 | nt | ++ |
| | 27036-211 | TW | D1 | + | +++ |
| | 809 | LCDC | D1 | nt | +++ |
| | 813 | LCDC | D1 | nt | +++ |
| | 907 | LCDC | D1 | nt | +++ |
| | 913 | LCDC | D1 | nt | +++ |
| | 914 | LCDC | D1 | nt | +++ |
| | 930 | LCDC | D1 | nt | +++ |
| | 939 | LCDC | D1 | nt | +++ |
| | 955 | LCDC | D1 | nt | +++ |
| | 972 | LCDC | D1 | nt | +++ |
| | 4931 | ATCC | D1 | + | +++ |
| | 13076 | ATCC | D1 | nt | +++ |
| | 31194 | ATCC | D1 | nt | +++ |

TABLE 3-continued

The distribution of sefD and SefD among Salmonella isolates and other eubacteria

| Bacterial Species | Strains | Source[a] | Serogroup | SefD cross-reactive protein[b] | Hybridization[c] to sefD probe |
|---|---|---|---|---|---|
| | 89-2749 | PVL | D1 | nt | +++ |
| | JTSe1 | JT | D1 | nt | +++ |
| S. florida | | TJT | H | + | +++ |
| S. gallinarum | 9184 | ATCC | D1 | + | +++ |
| S. gaminara | | TJT | G2 | + | ++ |
| S. havana | | TJT | G2 | + | ++ |
| S. infantis | JTSi1 | JT | C1 | + | ++ |
| S. javiana | 10721 | ATCC | D1 | + | nt |
| S. manhatten | | TJT | C2 | + | nt |
| S. minnesota | | TJT | L | + | ++ |
| S. newport | | TJT | C2 | + | ++ |
| S. nienstedten | | TJT | C2 | + | ++ |
| S. oranienburg | 9230 | ATCC | C1 | + | nt |
| S. pullorum | 9120 | ATCC | D1 | + | +++ |
| | 10398 | ATCC | D1 | nt | +++ |
| | 19945 | ATCC | D1 | nt | +++ |
| | 89-2331 | PVL | D1 | nt | +++ |
| | 90-1175 | PVL | D1 | nt | +++ |
| S. tennessee | | TJT | C1 | + | ++ |
| S. typhi | | UVic | D1 | + | nt |
| S. typhimurium | 962 | TJT | B | + | ++ |
| | Bowmer11 | TJT | B | + | ++ |
| | F18-1 | TJT | B | nt | ++ |
| | F112-2 | TJT | B | + | nt |
| | JTSt2 | JT | B | nt | ++ |
| | JTSt3 | JT | B | nt | ++ |
| | S736 | TJT | B | + | ++ |
| S. worthington | | TJT | G2 | + | ++ |
| Other Enterobacteriaceae | | | | | |
| Citrobacter freundii | 8090 | UVic | | + | + |
| Enterobacter aerogenes | | UVic | | + | + |
| Erwinia caratovora | | UVic | | + | + |
| Escherichia coli | 11775 | ATCC | | + | ++ |
| | C600 | ATCC | | + | nt |
| | HM101 | ATCC | | nt | ++ |
| | E1049a-13 | TJT | | + | ++ |
| | 438Hf | TJT | | + | ++ |
| | B41M | LE | | + | ++ |
| | HM1475 | LE | | + | ++ |
| | Vietnam I/1 | LE | | + | ++ |
| | Gambia G3 | LE | | + | ++ |
| | NG7c | LE | | + | ++ |
| | NG7c1 | LE | | + | ++ |
| | VietG | LE | | + | ++ |
| Hafnia alvei | | UVic | | + | + |
| Klebsiella pneumoniae | 13883 | ATCC | | + | ++ |
| Proteus vulgaris | | UVic | | +[d] | + |
| Providencia rettgeri | | UVic | | +[d] | + |
| Serratia marcescens | | UVic | | − | − |
| Shigella boydii | | UVic | | + | nt |
| Shigella dysenteriae | | UVic | | + | nt |
| Shigella flexneri | | UVic | | + | nt |
| Shigella sonnei | | UVic | | + | ++ |
| Other eubacteria | | | | | |
| Aeromonas hydrophila | | TJT | | − | − |
| Aeromonas salmonicida | | WWK | | − | − |
| Bacillus subtilis | | UVic | | − | − |
| Pseudomonas aeruginosa | | UVic | | − | − |
| Staphylococcus | | UVic | | − | nt |

[a]ATCC, American Type Culture Collection; BBF, B. B. Finlay, Biotechnology Laboratory and Departments of Biochemistry and Microbiology, University of British Columbia, Vancouver, Canada; JT, J. Tomas, Departement Microbiologie, Universitat de Barcelona, Spain; LCDC, H. Lior, National Enteric Reference Center of the Laboratory Centre for Disease Control, Ottawa, Canada; LE, L. Emödy, University Medical School, Institute of Microbiology, Pécs, Hungary; PVL, G. Thiele, Provincial Veterinary Laboratory of British Columbia, Abbotsford, Canada; TJT, T. J. Trust, Department of Biochemistry and Microbiology, University of Victoria, Canada; TW, T. Wadström, University of Lund, Sweden; UVic, Culture Collection of the Department of Biochemistry and Microbiology, University of Victoria, Canada; WWK, W. W. Kay, Department of Biochemistry and Microbiology, University of Victoria, Canada;
[b]Strains grown aerobically overnight in LB were screened for immunoreactive SefD proteins was recorded as positive (+), negative (−) or not tested (nt).
[c]Hybridization of membrane-bound bacterial DNA to the 442-bp sefD probe. The results of the hybridization are reported as weakly (+), moderately (++), or strongly (+++) positive or negative (−).
[d]The SefD immunologically cross-reactive band migrated with an apparent MW of 17,000 rather than with an apparent MW of 18,000 as observed with S. enteritidis 27655-3b SefD fimbrin.

Example 11 sefB or sefC based PCR assays for detection or *S. enteritidis, S. berta, S. dublin, S. gallinarum* and *S. pullorum*

The procedure described in Example 4 of resuspending cells in distilled water and briefly boiling them was found to be an effective method of cell lysis that permitted access to the chromosomal DNA for amplification. The primers for the PCR were a 24-met and a 21-met as follows: 5'-GATACTGCTGAACGTAGAAGG-3' (21 mer; SEQ ID No. 32); 5'-GCGTAAATCAGCATCTGCAGTAGC-3' (24 mer; SEQ ID No. 33).

Amplification was carried out in a 10 µl reaction volume containing 1 µl of heat-denatured bacterial DNA solution, 5 pmol of each primer, the four deoxynucleotide triphosphates at 0.5 mM each, and 0.4 units of Taq DNA polymerase (Stratagene, La Jolla, Calif.) in reaction buffer consisting of 50 mM Tris-HCl, pH 8.5, 20 mM KCl, 2.5 mM $MgCl_2$ and 0.5 mg/ml BSA. Thermocycling was performed on samples contained in sealed glass capillary tubes inserted in an Idaho Technology air driven thermocycler for 30 cycles of denaturation (95° C., 1 s), annealing (55° C., 1 s) and elongation (74° C., 21 s). The products of DNA amplification were separated by electrophoresis in 15% polyacrylamide gels and visualized by UV illumination following ethidium bromide staining.

The PCR assay detected less than 1 pg of target chromosomal DNA in the presence of a $10^6$ fold excess of DNA from a wide variety of other Enterobacteriaceae including strains or *E. coli*, Citrobacter, Enterobacter, Shigella and Serratia spp. This represents a detection limit of 1 to 10 cells using as an assay the visualization of PCR products by ethidium bromide staining of samples of amplified DNA electrophoresed in agarose gels (FIG. 14). The signal strength of the assay was increased by many orders of magnitude using the specific DNA probes described in Example 14 to detect the presence of amplified sefA gene fragments.

Hybridization of PCR amplified *S. enteritidis* sefB and sefC genes to DNA dot blot panels representing approximately 600 isolates of Salmonella and approximately 300 isolates of other Enterobacteriaceae (for a general list of the isolates, see Table 1) under stringent conditions showed that the distribution of the sefB and sefC genes were limited to isolates of *S. enteritidis, S. berta, S. dublin, S. gallinarum* and *S. pullorum*. PCR assays reliant upon DNA primers designed from the terminal sequences of sefB (targeting 'TTTTTTTACTTTCCGAAGA' (SEQ ID No. 34) and 'CTAATAATCTCTTATAATT' (SEQ ID No. 35)) and sefC (targeting 'AGTCGAAATTATATTGTCT' (SEQ ID No. 36) and 'TCATTTGCACACTCCATTT' (SEQ ID No. 37)) of *S. enteritidis* were conducted as outlined above. The sefB and sefC genes amplified well from *S. berta, S. dublin, S. enteritidis, S. gallinarum* or *S. pullorum*.

Example 12

Antibody-based assay for detection of SEF 17 or SEF 18

Crude IgG was first prepared by caprylic acid precipitation of extraneous serum proteins as outlined in Harlow and Lane, supra (*Antibodies; A Laboratory Manual*, Cold Spring Harbor, 1988). Pure IgG is prepared by Protein A affinity chromatography according to established methods for adsorption and elution of rabbit IgG. Purity is checked by sodium dodecyl sulfate-polyacrylamide gel electrophoresis (SDS-PAGE). The purified IgG was passively cross adsorbed against other (non-Salmonella) Enterobacteriaceae. The cross adsorbed IgG is chemically coupled to the enzyme horseradish peroxidase (HRP) by the method of Nakane and Kawaoi (*J. Histochem. Cytochem.* 22: 1084, 1974).

Twelve well microtiter strips are coated with 100 µl/well of cross-adsorbed rabbit anti-SEF17 or anti-SEF18 at a concentration of 10 µg/ml in 50 mM carbonate/bicarbonate buffer pH 9.6. The strips are incubated overnight at 4° C. or 3 hours at 37° C.

The strips are washed 5 times with 300 µl of phosphate buffered saline pH 7/0.05% (Tween 20), then blocked for 1 hour with 300 µl/well of PBS pH 7/0.05% Tween 20/5% glycine. The strips are washed as before, then washed three more times with PBS pH 7. The strips are post-coated for 10 minutes at room temperature with 5% glucosamine in $H_2O$. The strips are lyophilized overnight then sealed with cellulose acetate and stored at 4° C. in a foil pack containing a sachet of desiccant.

Test samples are enriched by inoculating growth media with the sample. Growth media is preferably either Luria broth or Modified Davis Minimal Media. Growth conditions for Luria broth (10 g/L tryptone, 5 g/L yeast extract, 10 g/L NaCl) are 18 hours at 37° C. for statistically. Growth conditions for Modified Davis Minimal Media (5.25 g/L $K_2HPO_4$, 4.28 g/L $Na_2HPO_4$, 2.25 g/L $KH_2PO_4$, 2.29 g/L $NaH_2PO_4$, 0.05 g/L $MgSO_4$, 1.0 g/L $(NH_4)_2SO_4$, 4 g/L protease peptone #3, 20 mM sodium citrate) are 37° C. for 18 hours with vigorous shaking. The test samples are then decanted and concentrated.

The test samples are first diluted in extraction buffer then boiled for 15 minutes and finally cooled on ice. 50 µl of sample is added to a well of a prepared strip. 50 µl of prediluted rabbit anti-SEF17 HRP or anti-SEF18 HRP conjugate, in PBS pH 7/0.05% Tween 20/5% glycine is added to the well that contains the sample and gently shaken. Wells are incubated at room temperature for 30 minutes, then washed 7 times with PBS pH 7/0.05% Tween 20. 100 µl of tetramethyl benzidine (TMB) is added to the wells and color development is allowed to proceed for five minutes at room temperature. Color development is stopped with the addition of 25 µl of 1M $H_3PO_4$.

Results can be read either visually or with a microplate reader at an absorbance of 405 nm.

In a preferred embodiment, the anti-SEF17 HRP or anti-SEF18 HRP conjugate are combined in a cocktail, and are further preferably combined in a cocktail with anti-SEF14 HRP conjugate, anti-SEF21 HRP conjugate, and/or anti-TctC HRP conjugate. Labels other than HRP can also be used according to the needs of the user.

Example 13

FimA-based diagnostic probes for Salmonella spp.

Purification of SEF21 fimbriae

SEF21 fimbriae were isolated from an LPS O-polysaccharide deficient, SEF17 fimbriae non-producing, TnphoA derivative of *S. enteritidis* 27655-3b, strain 3b-TnphoA-7. Serial culturing was conducted to optimize SEF21 production through selection of cells growing in the surface pellicle. Subsequently, cells were grown statically to an optical density ($OD_{600nm}$) of 10 by incubation for 90 h in 20 L of LB medium at 28° C.; a temperature restrictive for the production of SEF14 fimbriae. Approximately 95 to 100 g wet weight of cells were harvested by centrifugation (12,000×g, 15 min, 4° C.), washed with 1.2 L of 0.15M ethanolamine buffer, pH 10.5, and resuspended in 1.2 L of ethanolamine buffer. Fimbriae were sheared from the cells using a Waring blender and unbroken cells and cell membranes were removed by centrifugation. Trace amounts of SEF14 fimbriae were selectively precipitated by 18 h dialysis against two changes of 6 L of 10 mM Tris-HCl buffer, pH 7.5, containing 0.2% SDS (BRL, Gaithersburg, Md.), and harvested by centrifugation (15,000×g, 15 min, 4° C.). Residual SEF14 fimbriae were similarly pelleted following concentration of the supernatant to 30 ml by dialysis against polyethylene glycol 20,000. SEF21 fimbriae present in the supernatant were collected by centrifugation (250,000×g, 2h, 4° C.) and resuspended in 2 ml of ethanolamine buffer. Final purification was achieved by rate zonal centrifugation (60,000×g, 2.5 h, 4° C.) in a sucrose gradient (15% (w/v) to 75% (w/v) sucrose in 0.15M ethanolamine, pH 10.5, containing 0.5% deoxycholate). Peak fractions were identified by SDS-PAGE, pooled and dialyzed against 8 L of distilled water. SEF21 fimbriae were resuspended in distilled water and passed through a Detoxi-Gel (Pierce Chemical Co., Rockford, Ill.) column to remove trace levels of LPS. Samples of SEF21 fimbriae were analyzed by SDS-PAGE to confirm the absence of other proteins or LPS detectable by silver staining. The purity of the SEF21 fimbrial preparation was confirmed by Western blotting and immunoelectron microscopy.

Immunoassays

To prepare antisera to *S. enteritidis* 27655-3b SEF21, purified SEF21 fimbriae, or membrane-bound FimA structural fimbrin protein prepared by Western blotting onto Trans-Blot® nitrocellulose membrane (Bio-Rad Laboratories, Hercules, Calif.), were used to immunize New Zealand white rabbits. Polyclonal antisera to native SEF21 (titre>$10^8$) was used provided more sensitive detection of Salmonella Type 1 fimbriae and fimbrin protein than antisera to the SEF21 structural fimbrin protein, FimA (titre~$10^4$). Antibodies that were weakly reactive with *C. freundii* or *C. amalanaticus* were removed by repeated adsorption against cells of Citrobacter spp. without compromising immunodetection of Salmonella Type 1 and Type 2 fimbriae. Anti-SEF21 IgG was obtained by HPLC using a mono-Q column (Pharmacia, Uppsala, Sweden). Anti-SEF21 antibodies were purified by affinity chromatography using SEF21 fimbriae coupled to AminoLink™ Gel (Pierce Chemical Company, Rockford, Ill.).

Cross-reactive, Salmonella Type 1 fimbrin proteins were detected by Western blotting as previously described. Type 1 or Type 2 fimbriae were detected on whole cells by enzyme-linked immunosorbent assays (ELISA) performed by standard methods. Microtiter plates (Costar EIA/RIA places, Costar Corp., Cambridge, Mass.) were coated by incubation overnight at 37° C. with washed cells suspended in PBS to an $OD_{620nm}$ of 0.1. Goat, anti-rabbit, IgG-alkaline phosphatase conjugate (Cedarlane Laboratories Ltd., Hornby, ON) served as the secondary antibody. The results of the assays are set forth in Table 4.

TABLE 4

Detection of Type 1 fimbriae antigenically related to *S. enteritidis* SEF21.

| Bacterial Species | Strain | Source[a] | Serogroup | Western blot detection[b] | | | | | ELISA[c] |
|---|---|---|---|---|---|---|---|---|---|
| | | | | LB[d] | NB | PW | CFA | CFAP | |
| Salmonella spp. | | | | | | | | | |
| *S. agona* | Rosy-1 | TJT | B | ++ | + | + | + | + | 16 |
| | BTR-II-1 | TJT | B | + | + | + | + | + | nd |
| *S. albany* | | TJT | C3 | + | + | + | ++ | ++ | nd |
| *S. anatum* | | UVIC | E1 | + | + | + | + | + | nd |
| *S. arizonae* | | TJT | | + | + | + | + | + | 5 |
| *S. berta* | 8392 | ATCC | D1 | ++ | + | + | + | + | 43 |
| | 89-4065 | PVL | D1 | + | + | + | + | + | nd |
| | 90-1271 | PVL | D1 | ++ | + | + | + | ++ | nd |
| *S. bovis-morbificans* | FW22-1 | TJT | C2 | + | + | + | + | + | nd |
| *S. burnepta* | | UVIC | | + | + | − | + | + | nd |
| *S. cerro* | | TJT | K | ++ | + | + | + | ++ | 52 |
| *S. choleraesuis* | | BBF | C1 | ++ | − | − | + | + | 59 |
| *S. cubana* | WMNII-2 | TJT | G2 | + | + | − | + | + | nd |
| *S. dahomey* | | TJT | X | + | + | − | + | ++ | nd |
| *S. drypool* | | UVIC | E2 | ++ | + | + | + | ++ | nd |
| *S. dublin* | 15480 | ATCC | D1 | + | + | + | + | ++ | 39 |
| | 89-3320 | PVL | D1 | ++ | + | + | + | + | nd |
| | 89-3349 | PVL | D1 | + | + | + | + | + | nd |
| | 89-4189 | PVL | D1 | + | + | + | + | + | nd |
| | 90-243 | PVL | D1 | + | + | + | + | + | nd |
| | 90-1176 | PVL | D1 | + | + | + | + | + | nd |
| *S. eastbourne* | | UVIC | D1 | + | + | + | + | + | nd |
| *S. enteritidis* | 27655-3b | TW | D1 | +++ | ++ | ++ | +++ | +++ | 100 |
| | 27036-2I | TW | D1 | ++ | + | + | ++ | + | nd |
| | 27036-2II | TW | D1 | + | + | − | + | + | 19 |
| | 4931 | ATCC | D1 | +++ | ++ | ++ | ++ | ++ | 108 |
| | 13076 | ATCC | D1 | ++ | − | − | + | + | 67 |
| | 31194 | ATCC | D1 | + | + | + | + | + | 1 |
| | 89-2749 | PVL | D1 | ++ | ++ | + | ++ | + | 14 |
| | 801 | LCDC | D1 | ++ | ++ | ++ | ++ | ++ | 17 |
| | 809 | LCDC | D1 | ++ | + | ++ | + | ++ | nd |
| | 813 | LCDC | D1 | ++ | ++ | ++ | ++ | ++ | nd |
| | 907 | LCDC | D1 | + | + | + | ++ | ++ | nd |
| | 913 | LCDC | D1 | + | + | + | + | ++ | nd |
| | 914 | LCDC | D1 | ++ | ++ | + | ++ | + | nd |
| | 930 | LCDC | D1 | + | + | + | + | + | nd |
| | 939 | LCDC | D1 | + | + | + | + | + | nd |
| | 955 | LCDC | D1 | + | + | + | + | − | nd |

TABLE 4-continued

Detection of Type 1 fimbriae antigenically related to S. enteritidis SEF21.

| Bacterial Species | Strain | Source[a] | Serogroup | Western blot detection[b] | | | | | ELISA[c] |
|---|---|---|---|---|---|---|---|---|---|
| | | | | LB[d] | NB | PW | CFA | CFAP | |
| | 972 | LCDC | D1 | + | + | + | + | ++ | nd |
| | 989 | LCDC | D1 | − | − | − | − | − | 0 |
| | se1 | JT | D1 | + | + | + | + | + | nd |
| | se2 | JT | D1 | + | + | + | + | + | 19 |
| | se3 | JT | D1 | + | + | + | + | + | nd |
| | se4 | JT | D1 | + | + | + | + | + | nd |
| S. florida | | TJT | H | + | + | + | + | + | nd |
| S. gallinarum | 9184 | ATCC | D1 | ++ | − | − | + | + | 41 |
| S. gaminara | | TJT | I | + | − | − | + | + | nd |
| S. hadar | F9-1 | TJT | C2 | ++ | + | + | + | + | 38 |
| S. hamburg | RT1-1 | TJT | B | ++ | ++ | + | ++ | ++ | nd |
| S. havana | | TJT | G2 | + | + | + | + | + | nd |
| S. heidelberg | 8326 | ATCC | B | ++ | + | − | + | − | 43 |
| S. infantis | S41-16 | JT | C2 | ++ | + | − | + | + | 44 |
| S. infantis | si1 | JT | C2 | ++ | + | + | + | + | nd |
| S. infantis | si2 | JT | C2 | + | + | + | + | + | nd |
| S. infantis | si3 | JT | C2 | ++ | + | + | + | + | nd |
| S. infantis | si4 | JT | C2 | ++ | + | + | ++ | + | nd |
| S. javiana | 10721 | ATCC | D1 | + | | + | + | ++ | 22 |
| S. manhatten | Bowmer-6 | TJT | C2 | ++ | + | + | + | ++ | 55 |
| S. mbandaka | S108-8 | TJT | C1 | ++ | + | + | ++ | ++ | nd |
| S. mikwasima | | UVIC | C1 | + | + | + | + | + | nd |
| S. minnesota | | TJT | L | + | + | + | + | + | 12 |
| S. muenchen | Rosy-3 | TJT | C2 | + | + | + | + | + | 10 |
| S. muenchen | Bowmer-9 | TJT | C2 | + | + | ++ | + | + | nd |
| S. negev | HVRII-6 | TJT | S | + | + | + | + | − | nd |
| S. newport | | TJT | C2 | + | + | + | + | ++ | 13 |
| S. nienstedten | 5FC3 | TJT | C4 | ++ | + | + | ++ | ++ | nd |
| S. oranienburg | 9239 | ATCC | C1 | ++ | + | + | + | ++ | nd |
| S. paratyphi A | 11511 | ATCC | A | + | + | + | + | + | 2 |
| S. paratyphi B | S10-2 | ATCC | B | ++ | + | + | ++ | + | 30 |
| S. pullorum | 9120 | ATCC | D1 | + | + | + | + | + | 20 |
| | 10398 | ATCC | D1 | + | + | + | + | + | nd |
| | 19945 | ATCC | D1 | + | + | − | + | − | nd |
| | 89-2331 | PVL | D1 | + | + | − | − | + | nd |
| | 90-1175 | PVL | D1 | + | − | − | − | − | nd |
| S. saint-paul | S43-7 | TJT | B | ++ | + | + | + | + | nd |
| S. sandiego | MBL-1 | TJT | B | + | + | + | + | + | nd |
| S. schwarzengrund | S108-6 | TJT | B | ++ | + | + | ++ | + | nd |
| S. stanley | MTV-1 | TJT | B | + | + | + | + | + | nd |
| S. tennessee | | TJT | C1 | + | + | + | + | + | nd |
| S. typhi | | TJT | D1 | + | + | + | − | − | nd |
| S. typhimurium | F18-1 | TJT | B | + | + | + | + | + | 17 |
| | SU453 | TJT | B | + | + | − | + | + | 7 |
| | st1 | JT | B | + | + | + | + | + | nd |
| S. widemarsh | MonIII-6 | TJT | O | ++ | + | + | + | + | nd |
| S. worthington | | TJT | G2 | ++ | + | + | ++ | ++ | 17 |
| Other Enterobacteriaceae | | | | | | | | | |
| Citrobacter freundii | 8090 | UVIC | | − | − | − | − | − | 0 |
| Citrobacter amalanaticus | | GG | | − | − | − | − | − | 0 |
| Citrobacter diversus | | GG | | − | − | − | − | − | 0 |
| Enterobacter aerogenes | | UVIC | | − | − | − | − | − | 0 |
| Erwinia caratovora | | UVIC | | − | − | − | − | − | 0 |
| Escherichia coli | H2 | TJT | | − | − | − | − | − | 0 |
| Hafnia alvei | | UVIC | | − | − | − | − | − | 0 |
| Klebsiella pneumoniae | | UVIC | | − | − | − | − | − | 0 |
| Kluyvera cryocrescens | | GG | | − | − | − | − | − | 0 |
| Proteus vulgaris | | UVIC | | − | − | − | − | − | 0 |
| Providencia rettgeri | | UVIC | | − | − | − | − | − | 0 |
| Serratia marcescens | | UVIC | | − | − | − | − | − | 0 |
| Shigella sonnei | | UVIC | | − | − | − | − | − | 0 |
| Other eubacteria | | | | | | | | | |
| Aeromonas hydrophila | | TJT | | − | − | − | − | − | 0 |
| Aeromonas salmonicida | | WWK | | − | − | − | − | − | 0 |
| Bacillus subtilis | | UVIC | | − | − | − | − | − | 0 |
| Pseudomonas aeruginosa | | UVIC | | − | − | − | − | − | 0 |

TABLE 4-continued

Detection of Type 1 fimbriae antigenically related to S. enteritidis SEF21.

| | | | | Western blot detection[b] | | | | | |
|---|---|---|---|---|---|---|---|---|---|
| Bacterial Species | Strain | Source[a] | Serogroup | LB[d] | NB | PW | CFA | CFAP | ELISA[c] |

[a]Abbreviations of sources: ATCC, American Type Culture Collection; BBF, B. B. Finlay, Biotechnology Laboratory and Departments of Biochemistry and Microbiology, University of British Columbia, Vancouver, Canada; GG, G. Golumbeski, Promega Corporation, Madison, WI; JT, J. Tomas, Departement Microbiologie, Universitat de Barcelona, Spain; LCDC, H. Lior, National Enteric Reference Center of the Laboratory Centre for Disease Control, Ottawa, Canada; PVL, G. Thiele, Provincial Veterinary Laboratory of British Columbia, Abbotsford, Canada; TJT, T. J. Trust, Department of Biochemistry and Microbiology, University of Victoria, Canada; TW, T. Wadström, University of Lund, Sweden; UVIC, Culture Collection of the Department of Biochemistry and Microbiology, University of Victoria, Canada; WWK, W. W. Kay, Department of Biochemistry and Microbiology, University of Victoria, Canada;
[b]The results of Western blotting detection of Type 1 fimbrin protein conducted according to Müller et al. using polyclonal antisera to native SEF21 fimbriae were qualitatively compared to FimA production by S. enteritidis strain 27655-3b grown in LB broth as follows: +++ equally high level production; ++, moderate production; +, low level production; –, no detectable fimbrin band.
[c]ELISA detection of Type 1 fimbriae on whole cells was conducted by standard methods as described in Materials and Methods using polyclonal antisera to native SEF21 fimbriae. The results are presented as a percentage of the results obtained using cells of S. enteritidis 27655-3b obtained from LB broth cultures. "0" indicates an ELISA reaction equivalent to background readings. The values represent an average of three experiments. nd, not done.
[d]Abbreviations: LB, Luria-Bertani Broth; NB, Nutrient Broth; PW, Peptone-Water broth; CFA, Colonization Factor Antigen Broth; CFAP, solid CFA plate medium.

Example 14

AgfA-based diagnostic probes for Salmonella spp.

Figure 8:
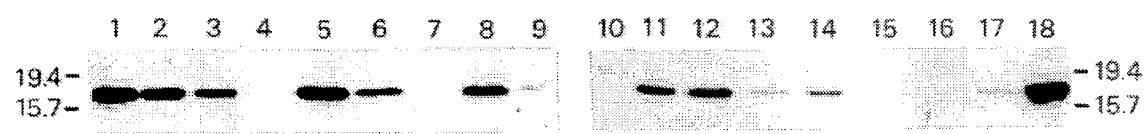
FIG. 8 depicts a Western blot identification of proteins from Salmonella strains and other members of the family Enterobacteriaceae that are immunologically cross-reactive with Agfa of *S. enteritidis* 27655-3b. Lanes: 1, *S. enteritidis* 27655-3b; 2, *S. hadar* F9-1; 3, *S. hamburg*, 4, *S. heidelberg*, 5, *S. infantis* S41-16; 6, *S. paratyphi* B; 7, *S. javiana*; 8, *S. mbandaka;* 9, *S. mikawasima;* 10, *S. typhi;* 11, *S. worthington;* 18, *S. enteritidis* 27655-3b. The molecular weights (in thousands) of comigrating, prestained protein standards (Bethesda Research Laboratories) are noted.

Aggregative fimbriae from colonies grown on T medium for 5 days were solubilized and subjected to Western blot analysis as described by Collinson et al. (8). Anti-AgfA immune serum served as the primary antibody. Visualization of proteins that were immunologically cross-reactive with Agfa was accomplished by using goat, anti-rabbit, immunoglobulin G-alkaline phosphatase conjugates (Caltag Laboratories, San Francisco, Calif.), the substrate 5-bromo-4-chloro-3-indolyl phosphate, and the enhancer Nitro Blue Tetrazolium (Sigma Chemical Co., St. Louis, Mo.). The results of the analysis, along with molecular weights (in thousands) of comigrating, prestained protein standards (Bethesda Research Laboratories) are shown in FIG. 8.

Example 15

Subcloning and Sequencing of the fimA Gene

To isolate the S enteritidis fimA gene, a genomic DNA library was prepared in a BamHI-digested, dephosphorylated cosmid cloning vector, pHC79 (Hohn and Collins, Gene 11: 291–198, 1980), using 35 to 40 kb fragments of strain 27655-3b chromosomal DNA generated by partial Sau3AI digestion (Sambrook et al., supra). Concatameric DNA was packaged in bacteriophage λ using an in vitro Gigapack® II packaging extract (Stratagene, La Jolla, Calif.) and transfected into E. coli DH5α. Following chloramphenicol amplification (Sambrook et al., supra), approximately 600 colonies were screened by hybridization to a [γ-$^{32}$P]-end labeled, 44-mer oligonucleotide fimA probe, fAII (CAGCTTTACGGCGATTGGTAATACGACTGCG-CAGGTGCC (SEQ. ID No. 38) at 63° C. (Doran et al., J. Clin. Microbial. 31: 2263–2273, 1993). A positively—hybridizing recombinant cosmid, pPB523 was purified and analyzed by Southern hybridization. A 4.4 kb EcoRI fragment encoding fimA was isolated by agarose gel electrophoresis and subcloned into pUC18 to create plasmid pJD12, which was maintained in E. coli DH5α.

To determine the sequence of both strands of S enteritidis fimA, a series of overlapping subclones were prepared by shotgun subcloning or by cloning gel-purified (Sambrook et al., supra) HinPI, HpaII, Sau3AI, or TaqI fragments into M13mp19 (Yannisch-Perron et al., supra) and propagating the recombinant bacteriophage in E. coli JM109. Appropriate recombinant plaques were identified by hybridization of the [γ-$^{32}$P]-end labeled probe fall to dot blots of recombinant M13mp19. Enzymatic DNA sequencing reactions were conducted using the T7 DNA polymerase and Taq-Track® sequencing Systems (Promega Corp., Madison, Wis.) and by cycle sequencing conducted for analysis using an ABI model 373A automated DNA sequencer (Applied Biosystems Inc., Mississauga, ON). DNA sequencing polyacrylamide gels containing 40% formamide and sequencing reactions utilizing 7-deaza-guanosine were used to resolve sequences that were fimA genes using the programs available on DNASIS (Hitachi Software Engineering Co., San Bruno, Calif.) and GeneWorks (Intelligenetics, Mountain View, Calif.).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated nucleic acid molecule comprising an isolated agfA gene Sequence I.D. No. 56 or Sequence I.D. No. 58.

2. The isolated nucleic acid molecule of claim 1 wherein said isolated nucleic acid molecule is a recombinant molecule.

3. A vector construct comprising an agfA gene Sequence I.D. No. 56 or Sequence I.D. No. 58.

4. The vector construct of claim 3 wherein said vector construct is an expression vector.

5. The vector construct of claim 3 wherein said vector construct is an expression vector able to express said gene upon introduction to a cell of a living plant or animal.

* * * * *

UNITED STATES PATENT AND TRADEMARK OFFICE
CERTIFICATE OF CORRECTION

PATENT NO.   : 5,635,617
DATED        : June 3, 1997
INVENTORS    : James L. Doran, William W. Kay and S. Karen Collinson It is certified that an error appears in the above identified patent and that said Letters Patent is hereby corrected as shown below:

On the title page : Item [75] denoting the inventors, please delete "Sharon C. Clouthier, Naniamo,".

Signed and Sealed this

Fifteenth Day of December, 1998

*Attest:*

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 61

( 2 ) INFORMATION FOR SEQ ID NO:1:

( i ) SEQUENCE CHARACTERISTICS:
        ( A ) LENGTH: 5 amino acids
        ( B ) TYPE: amino acid (D) TOPOLOGY: linear (xi) SEQUENCE DESCRIPTION: SEQ ID NO:1:

Gly Val Val Pro Gln
　　　　　　　　　　5

(2) INFORMATION FOR SEQ ID NO:2:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:2:

GGCGGAAGCT TGAATTCGTH GTHCCDCART GGGG                34

(2) INFORMATION FOR SEQ ID NO:3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:3:

GGGAAAGGTT GAATTCAGGA CGCTACTTGT G                  31

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:4:

TCCGGCCCGG ACTCAACG                                 18

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:5:

CAGCGCGGCG TTATTACCG                                19

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:6:

GGCGGCGGCA ATARTTCCGG CCCG 24

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:7:

CGGGCATCGC TTTGCAGAGG AAGCGC 26

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TGAATTAATT CCACAAGCTT TTTTTTTT 29

( 2 ) INFORMATION FOR SEQ ID NO:9:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CGACGGCCAG TGCCAAGCTT TTTTTTT 28

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:10:

GGGCGACTAT CGCGTTA 17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:11:

AGCCACTTGT AGCGGCC 17

( 2 ) INFORMATION FOR SEQ ID NO:12:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (ii) MOLECULE TYPE: Other nucleic acid (xi) SEQUENCE DESCRIPTION: SEQ ID NO:12:

GGAAGTGCAT TTTACGT                                                                17

(2) INFORMATION FOR SEQ ID NO:13:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: Other nucleic acid (xi) SEQUENCE DESCRIPTION: SEQ ID NO:13:

CATGCTGCCA AGACAGG                                                                17

(2) INFORMATION FOR SEQ ID NO:14:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: Other nucleic acid (xi) SEQUENCE DESCRIPTION: SEQ ID NO:14:

TTTGGATCTG CCAGGC                                                                 16

(2) INFORMATION FOR SEQ ID NO:15:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: Other nucleic acid (xi) SEQUENCE DESCRIPTION: SEQ ID NO:15:

GCGCCGTCAT GATCGCC                                                                17

(2) INFORMATION FOR SEQ ID NO:16:

(i) SEQUENCE CHARACTERISTICS:
    (A) LENGTH: 18 base pairss
    (B) TYPE: nucleic acid
    (C) STRANDEDNESS: single
    (D) TOPOLOGY: linear (xi) SEQUENCE DESCRIPTION: SEQ ID NO:16:

TCGGGATGCT GTTCGGCG                                                               18

(2) INFORMATION FOR SEQ ID NO:17:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:17:

CTGCCTGCGG AGTCGGC                                                                                              17

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:18:

GTCGCAAGGC CAAGACCG                                                                                             18

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:19:

GTGTATCGGC ACCACCCTG                                                                                            19

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:20:

CCCGGCGATG TTCACCG                                                                                              17

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:21:

CCAATACCGC GCCGGAG                                                                                              17

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:22:

GCGGAGGCAA TGATGAGCG                                                                                            19

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:23:

TGCCGCCATA CTCACAGCC                                                                                            19

( 2 ) INFORMATION FOR SEQ ID NO:24:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

TCTTGGCAGC ATGATGGCG                                                                                 19

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

CTGGCAATGG TCGCCCG                                                                                17

( 2 ) INFORMATION FOR SEQ ID NO:26:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

GCAATCAGCA GCGCAGC                                                                                17

( 2 ) INFORMATION FOR SEQ ID NO:27:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:27:

ATGGATACCT GGATATATCT TTCTCAGGG                                        29

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:28:

TATTTATTTA AGCCGGGTTT                                                  20

( 2 ) INFORMATION FOR SEQ ID NO:29:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:29:

GGGACTGTGG TCGCCTTTTC CGG 23

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:30:

CCGCCCTCAA AGGCAACGTA GCGC 24

( 2 ) INFORMATION FOR SEQ ID NO:31:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:31:

GTCATAGCTG TTTCCCG 17

( 2 ) INFORMATION FOR SEQ ID NO:32:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:32:

GATACTGCTG AACGTAGAAG G 21

( 2 ) INFORMATION FOR SEQ ID NO:33:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:33:

GCGTAAATCA GCATCTGCAG TAGC 24

( 2 ) INFORMATION FOR SEQ ID NO:34:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO:34:

TTTTTTTACT TTCCGAAGA 19

(2) INFORMATION FOR SEQ ID NO:35:

(i) SEQUENCE CHARACTERISTICS:
　　　　(A) LENGTH: 19 base pairs
　　　　(B) TYPE: nucleic acid
　　　　(C) STRANDEDNESS: single
　　　　(D) TOPOLOGY: linear (ii) MOLECULE TYPE: Other nucleic acid (xi) SEQUENCE DESCRIPTION: SEQ ID NO:35:

CTAATAATCT CTTATAATT        19

(2) INFORMATION FOR SEQ ID NO:36:

(i) SEQUENCE CHARACTERISTICS:
　　　　(A) LENGTH: 19 base pairs
　　　　(B) TYPE: nucleic acid
　　　　(C) STRANDEDNESS: single
　　　　(D) TOPOLOGY: linear (ii) MOLECULE TYPE: Other nucleic acid (xi) SEQUENCE DESCRIPTION: SEQ ID NO:36:

AGTCGAAATT ATATTGTCT        19

(2) INFORMATION FOR SEQ ID NO:37:

(i) SEQUENCE CHARACTERISTICS:
　　　　(A) LENGTH: 19 base pairs
　　　　(B) TYPE: nucleic acid
　　　　(C) STRANDEDNESS: single
　　　　(D) TOPOLOGY: linear (ii) MOLECULE TYPE: Other nucleic acid (xi) SEQUENCE DESCRIPTION: SEQ ID NO:37:

TCATTTGCAC ACTCCATTT        19

(2) INFORMATION FOR SEQ ID NO:38:

(i) SEQUENCE CHARACTERISTICS:
　　　　(A) LENGTH: 39 base pairs
　　　　(B) TYPE: nucleic acid
　　　　(C) STRANDEDNESS: single
　　　　(D) TOPOLOGY: linear (xi) SEQUENCE DESCRIPTION: SEQ ID NO:38:

CAGCTTTACG GCGATTGGTA ATACGACTGC GCAGGTGCC        39

(2) INFORMATION FOR SEQ ID NO:39:

(i) SEQUENCE CHARACTERISTICS:
　　　　(A) LENGTH: 4406 base pairs
　　　　(B) TYPE: nucleic acid
　　　　(C) STRANDEDNESS: double
　　　　(D) TOPOLOGY: linear (ii) MOLECULE TYPE: DNA (genomic)

(ix) FEATURE:
　　　　(A) NAME/KEY: CDS
　　　　(B) LOCATION: 136..630

(ix) FEATURE:
　　　　(A) NAME/KEY: CDS
　　　　(B) LOCATION: 755..1492

(ix) FEATURE:
　　　　(A) NAME/KEY: CDS
　　　　(B) LOCATION: 1511..3953

( i x ) FEATURE:
    ( A ) NAME/KEY: CDS
    ( B ) LOCATION: 3957..4400

( x i ) SEQUENCE DESCRIPTION: SEQ ID NO:39:

```
GGGGATGTTG TGTAAAGATA AAAAAATAGT GATCCTTGTT TTTTTCTTA AATTTTTAAA                60

ATGGCGTGAG TATATTAGCA TCCGCACAGA TAAATTGTGC GAATGCTAAT AGTTGATTTT              120

TGGAGATTTT GTAAT ATG CGT AAA TCA GCA TCT GCA GTA GCA GTT CTT GCT              171
              Met Arg Lys Ser Ala Ser Ala Val Ala Val Leu Ala
                1               5                  10

TTA ATT GCA TGT GGC AGT GCC CAC GCA GCT GGC TTT GTT GGT AAC AAA              219
Leu Ile Ala Cys Gly Ser Ala His Ala Ala Gly Phe Val Gly Asn Lys
         15                  20                  25

GCA GTG GTT CAG GCA GCG GTT ACT ATT GCA GCT CAG AAT ACA ACA TCA              267
Ala Val Val Gln Ala Ala Val Thr Ile Ala Ala Gln Asn Thr Thr Ser
     30                  35                  40

GCC AAC TGG AGT CAG GAT CCT GGC TTT ACA GGG CCT GCT GTT GCT GCT              315
Ala Asn Trp Ser Gln Asp Pro Gly Phe Thr Gly Pro Ala Val Ala Ala
 45                  50                  55                  60

GGT CAG AAA GTT GGT ACT CTC AGC ATT ACT GCT ACT GGT CCA CAT AAC              363
Gly Gln Lys Val Gly Thr Leu Ser Ile Thr Ala Thr Gly Pro His Asn
                 65                  70                  75

TCA GTA TCT ATT GCA GGT AAA GGG GCT TCG GTA TCT GGT GGT GTA GCC              411
Ser Val Ser Ile Ala Gly Lys Gly Ala Ser Val Ser Gly Gly Val Ala
             80                  85                  90

ACT GTC CCG TTC GTT GAT GGA CAA GGA CAG CCT GTT TTC CGT GGG CGT              459
Thr Val Pro Phe Val Asp Gly Gln Gly Gln Pro Val Phe Arg Gly Arg
         95                  100                 105

ATT CAG GGA GCC AAT ATT AAT GAC CAA GCA AAT ACT GGA ATT GAC GGG              507
Ile Gln Gly Ala Asn Ile Asn Asp Gln Ala Asn Thr Gly Ile Asp Gly
     110                 115                 120

CTT GCA GGT TGG CGA GTT GCC AGC TCT CAA GAA ACG CTA AAT GTC CCT              555
Leu Ala Gly Trp Arg Val Ala Ser Ser Gln Glu Thr Leu Asn Val Pro
125                 130                 135                 140

GTC ACA ACC TTT GGT AAA TCG ACC CTG CCA GCA GGT ACT TTC ACT GCG              603
Val Thr Thr Phe Gly Lys Ser Thr Leu Pro Ala Gly Thr Phe Thr Ala
                 145                 150                 155

ACC TTC TAC GTT CAG CAG TAT CAA AAC TAATTTAATT TAAACTTTAT                    650
Thr Phe Tyr Val Gln Gln Tyr Gln Asn
             160                 165

AAATGCCCTC AATATGAGGG CATTTGGATA ATTTTATTAT TTTAAAAATA TCTATTTGA              710

ATAGATAGGT TTATGCTTC CATGCAAAAA CTTAAGAGG GATT ATG TAT ATT TTG               766
                                                 Met Tyr Ile Leu
                                                  1

AAT AAA TTT ATA CGT AGA ACT GTT ATC TTT TTC TTT TTT TGC TAC CTT              814
Asn Lys Phe Ile Arg Arg Thr Val Ile Phe Phe Phe Phe Cys Tyr Leu
 5                   10                  15                  20

CCA ATT GCT TCT TCG GAA AGT AAA AAA ATT GAG CAA CCA TTA TTA ACA              862
Pro Ile Ala Ser Ser Glu Ser Lys Lys Ile Glu Gln Pro Leu Leu Thr
                 25                  30                  35

CAA AAA TAT TAT GGC CTA AGA TTG GGC ACT ACA CGT GTT ATT TAT AAA              910
Gln Lys Tyr Tyr Gly Leu Arg Leu Gly Thr Thr Arg Val Ile Tyr Lys
             40                  45                  50

GAA GAT GCT CCA TCA ACA AGT TTT TGG ATT ATG AAT GAA AAA GAA TAT              958
Glu Asp Ala Pro Ser Thr Ser Phe Trp Ile Met Asn Glu Lys Glu Tyr
 55                  60                  65

CCA ATC CTT GTT CAA ACT CAA GTA TAT AAT GAT GAT AAA TCA TCA AAA             1006
Pro Ile Leu Val Gln Thr Gln Val Tyr Asn Asp Asp Lys Ser Ser Lys
                 70                  75                  80
```

| | | | | | | | | | | | | | | | | |
|---|---|---|---|---|---|---|---|---|---|---|---|---|---|---|---|---|
| GCT | CCA | TTT | ATT | GTA | ACA | CCA | CCT | ATT | TTG | AAA | GTT | GAA | AGT | AAT | GCG | 1054 |
| Ala | Pro | Phe | Ile | Val | Thr | Pro | Pro | Ile | Leu | Lys | Val | Glu | Ser | Asn | Ala | |
| 85 | | | | 90 | | | | | 95 | | | | | | 100 | |
| CGA | ACA | AGA | TTG | AAG | GTA | ATA | CCA | ACA | AGT | AAT | CTA | TTC | AAT | AAA | AAT | 1102 |
| Arg | Thr | Arg | Leu | Lys | Val | Ile | Pro | Thr | Ser | Asn | Leu | Phe | Asn | Lys | Asn | |
| | | | | 105 | | | | | 110 | | | | | 115 | | |
| GAG | GAG | TCT | TTG | TAT | TGG | TTG | TGT | GTA | AAA | GGA | GTC | CCA | CCA | CTA | AAT | 1150 |
| Glu | Glu | Ser | Leu | Tyr | Trp | Leu | Cys | Val | Lys | Gly | Val | Pro | Pro | Leu | Asn | |
| | | | 120 | | | | | 125 | | | | | 130 | | | |
| GAT | AAT | GAA | AGC | AAT | AAT | AAA | AAC | AAC | ATA | ACT | ACG | AAT | CTT | AAT | GTG | 1198 |
| Asp | Asn | Glu | Ser | Asn | Asn | Lys | Asn | Asn | Ile | Thr | Thr | Asn | Leu | Asn | Val | |
| | | | 135 | | | | 140 | | | | | 145 | | | | |
| AAT | GTG | GTT | ACG | AAT | AGT | TGT | ATT | AAA | TTA | ATT | TAT | AGG | CCT | AAA | ACT | 1246 |
| Asn | Val | Val | Thr | Asn | Ser | Cys | Ile | Lys | Leu | Ile | Tyr | Arg | Pro | Lys | Thr | |
| | | 150 | | | | | 155 | | | | | 160 | | | | |
| ATA | GAC | TTA | ACG | ACA | ATG | GAG | ATT | GCA | GAT | AAA | TTA | AAG | TTA | GAG | AGA | 1294 |
| Ile | Asp | Leu | Thr | Thr | Met | Glu | Ile | Ala | Asp | Lys | Leu | Lys | Leu | Glu | Arg | |
| 165 | | | | | 170 | | | | | 175 | | | | | 180 | |
| AAA | GGA | AAT | AGT | ATA | GTT | ATA | AAG | AAT | CCA | ACA | TCA | TCA | TAT | GTG | AAT | 1342 |
| Lys | Gly | Asn | Ser | Ile | Val | Ile | Lys | Asn | Pro | Thr | Ser | Ser | Tyr | Val | Asn | |
| | | | | 185 | | | | | 190 | | | | | 195 | | |
| ATT | GCA | AAT | ATT | AAA | TCT | GGT | AAT | TTA | AGT | TTT | AAT | ATT | CCA | AAT | GGA | 1390 |
| Ile | Ala | Asn | Ile | Lys | Ser | Gly | Asn | Leu | Ser | Phe | Asn | Ile | Pro | Asn | Gly | |
| | | | 200 | | | | | 205 | | | | | 210 | | | |
| TAT | ATT | GAG | CCA | TTT | GGA | TAT | GCT | CAA | TTA | CCT | GGT | GGA | GTA | CAT | AGT | 1438 |
| Tyr | Ile | Glu | Pro | Phe | Gly | Tyr | Ala | Gln | Leu | Pro | Gly | Gly | Val | His | Ser | |
| | | 215 | | | | | 220 | | | | | 225 | | | | |
| AAA | ATA | ACT | TTG | ACT | ATT | TTG | GAT | GAT | AAC | GGC | GCT | GAA | ATT | ATA | AGA | 1486 |
| Lys | Ile | Thr | Leu | Thr | Ile | Leu | Asp | Asp | Asn | Gly | Ala | Glu | Ile | Ile | Arg | |
| | 230 | | | | | 235 | | | | | 240 | | | | | |
| GAT | TAT | TAGTTTAAGG | | TGTAAACAA | | ATG | AAG | AAA | ACC | ACA | ATT | ACT | CTA | TTT | | 1538 |
| Asp | Tyr | | | | | Met | Lys | Lys | Thr | Thr | Ile | Thr | Leu | Phe | | |
| 245 | | | | | | 1 | | | | 5 | | | | | | |
| GTT | TTA | ACC | AGT | GTA | TTT | CAC | TCT | GGA | AAT | GTT | TTC | TCC | AGA | CAA | TAT | 1586 |
| Val | Leu | Thr | Ser | Val | Phe | His | Ser | Gly | Asn | Val | Phe | Ser | Arg | Gln | Tyr | |
| 10 | | | | | 15 | | | | | 20 | | | | | 25 | |
| AAT | TTC | GAC | TAT | GGA | AGT | TTG | AGT | CTT | CCT | CCC | GGT | GAG | AAT | GCA | TCT | 1634 |
| Asn | Phe | Asp | Tyr | Gly | Ser | Leu | Ser | Leu | Pro | Pro | Gly | Glu | Asn | Ala | Ser | |
| | | | | 30 | | | | | 35 | | | | | 40 | | |
| TTT | CTA | AGT | GTT | GAA | ACG | CTT | CCT | GGT | AAT | TAT | GTT | GTT | GAT | GTA | TAT | 1682 |
| Phe | Leu | Ser | Val | Glu | Thr | Leu | Pro | Gly | Asn | Tyr | Val | Val | Asp | Val | Tyr | |
| | | | 45 | | | | | 50 | | | | | 55 | | | |
| TTG | AAT | AAT | CAG | TTA | AAA | GAA | ACT | ACT | GAG | TTG | TAT | TTC | AAA | TCA | ATG | 1730 |
| Leu | Asn | Asn | Gln | Leu | Lys | Glu | Thr | Thr | Glu | Leu | Tyr | Phe | Lys | Ser | Met | |
| | | | 60 | | | | | 65 | | | | | 70 | | | |
| ACT | CAG | ACT | CTA | GAA | CCA | TGC | TTA | ACA | AAA | GAA | AAA | CTT | ATA | AAG | TAT | 1778 |
| Thr | Gln | Thr | Leu | Glu | Pro | Cys | Leu | Thr | Lys | Glu | Lys | Leu | Ile | Lys | Tyr | |
| | 75 | | | | | 80 | | | | | 85 | | | | | |
| GGG | ATC | GCC | ATC | CAG | GAG | CTT | CAT | GGG | TTG | CAG | TTT | GAT | AAT | GAA | CAA | 1826 |
| Gly | Ile | Ala | Ile | Gln | Glu | Leu | His | Gly | Leu | Gln | Phe | Asp | Asn | Glu | Gln | |
| 90 | | | | | 95 | | | | | 100 | | | | | 105 | |
| TGC | GTT | CTC | TTA | GAG | CAT | TCT | CCT | CTT | AAA | TAT | ACT | TAT | AAC | GCG | GCT | 1874 |
| Cys | Val | Leu | Leu | Glu | His | Ser | Pro | Leu | Lys | Tyr | Thr | Tyr | Asn | Ala | Ala | |
| | | | | 110 | | | | | 115 | | | | | 120 | | |
| AAC | CAA | AGT | TTG | CTT | TTA | AAT | GCA | CCA | TCT | AAA | ATT | CTA | TCT | CCA | ATA | 1922 |
| Asn | Gln | Ser | Leu | Leu | Leu | Asn | Ala | Pro | Ser | Lys | Ile | Leu | Ser | Pro | Ile | |
| | | | 125 | | | | | 130 | | | | | 135 | | | |
| GAC | AGT | GAA | ATT | GCT | GAT | GAA | AAT | ATC | TGG | GAT | GAT | GGC | ATT | AAC | GCT | 1970 |
| Asp | Ser | Glu | Ile | Ala | Asp | Glu | Asn | Ile | Trp | Asp | Asp | Gly | Ile | Asn | Ala | |
| | | 140 | | | | | 145 | | | | | 150 | | | | |

| | | | | | | | | | | | | | | | | |
|---|---|---|---|---|---|---|---|---|---|---|---|---|---|---|---|---|
| TTT | CTT | TTA | AAT | TAC | AGA | GCT | AAT | TAT | TTG | CAT | TCT | AAG | GTT | GGA | GGA | 2018 |
| Phe | Leu | Leu | Asn | Tyr | Arg | Ala | Asn | Tyr | Leu | His | Ser | Lys | Val | Gly | Gly | |
| | 155 | | | | 160 | | | | | 165 | | | | | | |
| GAA | GAT | TCA | TAC | TTT | GGT | CAA | ATT | CAA | CCT | GGT | TTT | AAT | TTT | GGT | CCC | 2066 |
| Glu | Asp | Ser | Tyr | Phe | Gly | Gln | Ile | Gln | Pro | Gly | Phe | Asn | Phe | Gly | Pro | |
| 170 | | | | | 175 | | | | | 180 | | | | | 185 | |
| TGG | CGG | CTA | AGG | AAT | CTA | TCA | TCT | TGG | CAA | AAC | TTG | TCA | AGC | GAA | AAA | 2114 |
| Trp | Arg | Leu | Arg | Asn | Leu | Ser | Ser | Trp | Gln | Asn | Leu | Ser | Ser | Glu | Lys | |
| | | | | 190 | | | | | 195 | | | | | 200 | | |
| AAA | TTT | GAA | TCA | GCA | TAT | ATT | TAT | GCT | GAG | CGA | GGT | TTA | AAA | AAA | ATA | 2162 |
| Lys | Phe | Glu | Ser | Ala | Tyr | Ile | Tyr | Ala | Glu | Arg | Gly | Leu | Lys | Lys | Ile | |
| | | | | 205 | | | | | 210 | | | | | 215 | | |
| AAG | AGC | AAA | CTA | ACA | GTT | GGG | GAC | AAA | TAT | ACC | AGT | GCA | GAT | TTA | TTC | 2210 |
| Lys | Ser | Lys | Leu | Thr | Val | Gly | Asp | Lys | Tyr | Thr | Ser | Ala | Asp | Leu | Phe | |
| | | | 220 | | | | | 225 | | | | | 230 | | | |
| GAT | AGC | GTA | CCA | TTT | AGA | GGC | TTT | TCT | TTA | AAT | AAA | GAT | GAA | AGT | ATG | 2258 |
| Asp | Ser | Val | Pro | Phe | Arg | Gly | Phe | Ser | Leu | Asn | Lys | Asp | Glu | Ser | Met | |
| | | 235 | | | | | 240 | | | | | 245 | | | | |
| ATA | CCT | TTC | TCA | CAG | AGA | ACA | TAT | TAT | CCA | ACA | ATA | CGT | GGT | ATT | GCG | 2306 |
| Ile | Pro | Phe | Ser | Gln | Arg | Thr | Tyr | Tyr | Pro | Thr | Ile | Arg | Gly | Ile | Ala | |
| 250 | | | | | 255 | | | | | 260 | | | | | 265 | |
| AAA | ACC | AAT | GCG | ACT | GTA | GAA | GTA | AGA | CAA | AAT | GGA | TAC | TTG | ATA | TAT | 2354 |
| Lys | Thr | Asn | Ala | Thr | Val | Glu | Val | Arg | Gln | Asn | Gly | Tyr | Leu | Ile | Tyr | |
| | | | | 270 | | | | | 275 | | | | | 280 | | |
| TCT | ACT | TCA | GTC | CCC | CCC | GGG | CAA | TTC | GAG | ATA | GGT | AGA | GAA | CAA | ATT | 2402 |
| Ser | Thr | Ser | Val | Pro | Pro | Gly | Gln | Phe | Glu | Ile | Gly | Arg | Glu | Gln | Ile | |
| | | | 285 | | | | | 290 | | | | | 295 | | | |
| GCT | GAT | CTT | GGT | GTT | GGG | GTT | GGG | GTT | CTT | GAT | GTT | AGC | ATT | TAT | GAA | 2450 |
| Ala | Asp | Leu | Gly | Val | Gly | Val | Gly | Val | Leu | Asp | Val | Ser | Ile | Tyr | Glu | |
| | | | 300 | | | | | 305 | | | | | 310 | | | |
| AAA | AAT | GGG | CAG | GTC | CAA | AAC | TAT | ACA | GTG | CCA | TAT | TCA | ACT | CCT | GTA | 2498 |
| Lys | Asn | Gly | Gln | Val | Gln | Asn | Tyr | Thr | Val | Pro | Tyr | Ser | Thr | Pro | Val | |
| | 315 | | | | | 320 | | | | | 325 | | | | | |
| TTA | TCT | TTG | CCT | GAT | GGA | TAT | TCT | AAA | TAT | AGT | GTA | ACT | ATT | GGT | AGA | 2546 |
| Leu | Ser | Leu | Pro | Asp | Gly | Tyr | Ser | Lys | Tyr | Ser | Val | Thr | Ile | Gly | Arg | |
| 330 | | | | | 335 | | | | | 340 | | | | | 345 | |
| TAC | AGG | GAG | GTT | AAC | AAT | GAT | TAT | ATC | GAT | CCT | GTT | TTT | TTT | GAA | GGG | 2594 |
| Tyr | Arg | Glu | Val | Asn | Asn | Asp | Tyr | Ile | Asp | Pro | Val | Phe | Phe | Glu | Gly | |
| | | | | 350 | | | | | 355 | | | | | 360 | | |
| ACT | TAT | ATA | TAT | GGT | CTG | CCT | TAT | GGG | TTT | ACT | TTA | TTT | GGT | GGA | GTG | 2642 |
| Thr | Tyr | Ile | Tyr | Gly | Leu | Pro | Tyr | Gly | Phe | Thr | Leu | Phe | Gly | Gly | Val | |
| | | | 365 | | | | | 370 | | | | | 375 | | | |
| CAA | TGG | GTA | AAT | ATT | TAT | AAT | TCA | TAT | GCC | ATA | GGC | GCA | AGT | AAA | GAT | 2690 |
| Gln | Trp | Val | Asn | Ile | Tyr | Asn | Ser | Tyr | Ala | Ile | Gly | Ala | Ser | Lys | Asp | |
| | | 380 | | | | | 385 | | | | | 390 | | | | |
| ATT | GGT | GAG | TAT | GGT | GCT | CTG | TCT | TTT | GAC | TGG | AAA | ACA | TCT | GTT | TCG | 2738 |
| Ile | Gly | Glu | Tyr | Gly | Ala | Leu | Ser | Phe | Asp | Trp | Lys | Thr | Ser | Val | Ser | |
| | 395 | | | | | 400 | | | | | 405 | | | | | |
| AAG | ACT | GAT | ACA | TCC | AAT | GAA | AAT | GGT | CAT | GCA | TAT | GGG | ATT | AGA | TAC | 2786 |
| Lys | Thr | Asp | Thr | Ser | Asn | Glu | Asn | Gly | His | Ala | Tyr | Gly | Ile | Arg | Tyr | |
| 410 | | | | | 415 | | | | | 420 | | | | | 425 | |
| AAT | AAA | AAT | ATC | GCT | CAG | ACA | AAC | ACC | GAA | GTA | TCT | TTG | GCT | AGT | CAT | 2834 |
| Asn | Lys | Asn | Ile | Ala | Gln | Thr | Asn | Thr | Glu | Val | Ser | Leu | Ala | Ser | His | |
| | | | | 430 | | | | | 435 | | | | | 440 | | |
| TAC | TAT | TAT | TCG | AAA | AAT | TAT | AGA | ACT | TTT | TCT | GAA | GCA | ATT | CAT | AGT | 2882 |
| Tyr | Tyr | Tyr | Ser | Lys | Asn | Tyr | Arg | Thr | Phe | Ser | Glu | Ala | Ile | His | Ser | |
| | | | 445 | | | | | 450 | | | | | 455 | | | |
| AGC | GAG | CAT | GAT | GAA | TTT | TAC | GAT | AAA | AAT | AAG | AAA | TCA | ACA | ACC | TCT | 2930 |
| Ser | Glu | His | Asp | Glu | Phe | Tyr | Asp | Lys | Asn | Lys | Lys | Ser | Thr | Thr | Ser | |
| | | 460 | | | | | 465 | | | | | 470 | | | | |

| | | | | | | | | | | | | | | | | |
|---|---|---|---|---|---|---|---|---|---|---|---|---|---|---|---|---|
| ATG | TTA | TTA | AGT | CAG | GCA | TTA | GGA | TCT | CTG | GGT | TCT | GTT | AAC | TTA | AGC | 2978 |
| Met | Leu | Leu | Ser | Gln | Ala | Leu | Gly | Ser | Leu | Gly | Ser | Val | Asn | Leu | Ser | |
| 475 | | | | 480 | | | | | 485 | | | | | | | |
| TAC | AAT | TAT | GAT | AAA | TAT | TGG | AAA | CAT | GAA | GGT | AAA | AAA | TCA | ATA | ATT | 3026 |
| Tyr | Asn | Tyr | Asp | Lys | Tyr | Trp | Lys | His | Glu | Gly | Lys | Lys | Ser | Ile | Ile | |
| 490 | | | | 495 | | | | | 500 | | | | | | 505 | |
| GCT | AGT | TAT | GGG | AAG | AAT | TTA | AAT | GGT | GTT | TCG | TTA | TCG | CTT | TCA | TAT | 3074 |
| Ala | Ser | Tyr | Gly | Lys | Asn | Leu | Asn | Gly | Val | Ser | Leu | Ser | Leu | Ser | Tyr | |
| | | | | 510 | | | | | 515 | | | | | 520 | | |
| ACG | AAA | AGT | ACA | TCA | AAG | ATT | AGT | GAA | GAA | AAT | GAA | GAT | TTA | TTC | AGT | 3122 |
| Thr | Lys | Ser | Thr | Ser | Lys | Ile | Ser | Glu | Glu | Asn | Glu | Asp | Leu | Phe | Ser | |
| | | | 525 | | | | | 530 | | | | | 535 | | | |
| TTT | CTA | CTC | AGT | GTA | CCT | TTG | CAA | AAA | CTT | ACA | AAT | CAT | GAA | ATG | TAT | 3170 |
| Phe | Leu | Leu | Ser | Val | Pro | Leu | Gln | Lys | Leu | Thr | Asn | His | Glu | Met | Tyr | |
| | | | 540 | | | | | 545 | | | | | 550 | | | |
| GCT | ACA | TAT | CAA | AAC | TCA | TCC | TCT | TCA | AAG | CAT | GAT | ATG | AAT | CAT | GAT | 3218 |
| Ala | Thr | Tyr | Gln | Asn | Ser | Ser | Ser | Ser | Lys | His | Asp | Met | Asn | His | Asp | |
| | | 555 | | | | | 560 | | | | | 565 | | | | |
| TTA | GGT | ATT | ACT | GGT | GTG | GCA | TTT | AAT | AGC | CAA | TTG | ACA | TGG | CAA | GCA | 3266 |
| Leu | Gly | Ile | Thr | Gly | Val | Ala | Phe | Asn | Ser | Gln | Leu | Thr | Trp | Gln | Ala | |
| 570 | | | | | 575 | | | | | 580 | | | | | 585 | |
| AGA | GGG | CAA | ATA | GAA | GAT | AAA | TCG | AAA | AAT | CAA | AAG | GCT | ACA | TTT | TTA | 3314 |
| Arg | Gly | Gln | Ile | Glu | Asp | Lys | Ser | Lys | Asn | Gln | Lys | Ala | Thr | Phe | Leu | |
| | | | | 590 | | | | | 595 | | | | | 600 | | |
| AAT | GCT | TCT | TGG | CGA | GGT | ACT | TAT | GGG | GAG | ATC | GGA | GCA | AAC | TAT | AGT | 3362 |
| Asn | Ala | Ser | Trp | Arg | Gly | Thr | Tyr | Gly | Glu | Ile | Gly | Ala | Asn | Tyr | Ser | |
| | | | 605 | | | | | 610 | | | | | 615 | | | |
| CAT | AAT | GAA | ATA | AAT | CGT | GAT | ATT | GGG | ATG | AAT | GTT | TCT | GGT | GGG | GTG | 3410 |
| His | Asn | Glu | Ile | Asn | Arg | Asp | Ile | Gly | Met | Asn | Val | Ser | Gly | Gly | Val | |
| | | 620 | | | | | 625 | | | | | 630 | | | | |
| ATT | GCT | CAT | TCA | TCA | GGA | ATT | ACG | TTT | GGT | CAT | AGT | ATA | TCG | GAT | ACT | 3458 |
| Ile | Ala | His | Ser | Ser | Gly | Ile | Thr | Phe | Gly | His | Ser | Ile | Ser | Asp | Thr | |
| | 635 | | | | | 640 | | | | | 645 | | | | | |
| GCT | GCA | CTG | GTA | GAG | GCT | AAA | GGT | GTA | AGT | GGG | GCA | AAA | GTT | CTG | GGC | 3506 |
| Ala | Ala | Leu | Val | Glu | Ala | Lys | Gly | Val | Ser | Gly | Ala | Lys | Val | Leu | Gly | |
| 650 | | | | | 655 | | | | | 660 | | | | | 665 | |
| CTA | CCA | GGT | GTT | ATA | ACC | GAT | TTT | AGA | GGC | TAT | ACA | ATA | TCC | AGT | TAT | 3554 |
| Leu | Pro | Gly | Val | Ile | Thr | Asp | Phe | Arg | Gly | Tyr | Thr | Ile | Ser | Ser | Tyr | |
| | | | | 670 | | | | | 675 | | | | | 680 | | |
| CTT | ACT | CCA | TAT | ATG | AAT | AAC | TTC | ATA | TCT | ATA | GAT | CCA | ACA | ACG | TTA | 3602 |
| Leu | Thr | Pro | Tyr | Met | Asn | Asn | Phe | Ile | Ser | Ile | Asp | Pro | Thr | Thr | Leu | |
| | | | | 685 | | | | | 690 | | | | | 695 | | |
| CCA | ATA | AAT | ACG | GAT | ATT | AGG | CAA | ACT | GAT | ATT | CAA | GTA | GTT | CCT | ACC | 3650 |
| Pro | Ile | Asn | Thr | Asp | Ile | Arg | Gln | Thr | Asp | Ile | Gln | Val | Val | Pro | Thr | |
| | | 700 | | | | | 705 | | | | | 710 | | | | |
| GAA | GGT | GCT | ATT | GTA | AAA | GCT | GTA | TAT | AAA | ACA | AGC | GTG | GGT | ACT | AAT | 3698 |
| Glu | Gly | Ala | Ile | Val | Lys | Ala | Val | Tyr | Lys | Thr | Ser | Val | Gly | Thr | Asn | |
| | | 715 | | | | | 720 | | | | | 725 | | | | |
| GCA | TTA | ATT | AGA | ATT | ACA | AGA | ACA | AAT | GGA | AAG | CCA | CTA | GCT | CTT | GGC | 3746 |
| Ala | Leu | Ile | Arg | Ile | Thr | Arg | Thr | Asn | Gly | Lys | Pro | Leu | Ala | Leu | Gly | |
| 730 | | | | | 735 | | | | | 740 | | | | | 745 | |
| ACA | GTT | CTT | TCA | CTT | AAG | AAT | AAT | GAT | GGA | GTA | ATC | CAA | TCA | ACA | TCT | 3794 |
| Thr | Val | Leu | Ser | Leu | Lys | Asn | Asn | Asp | Gly | Val | Ile | Gln | Ser | Thr | Ser | |
| | | | | 750 | | | | | 755 | | | | | 760 | | |
| ATT | GTT | GGC | GAA | GAT | GGT | CAG | GCA | TAT | GTA | TCT | GGA | TTG | TCA | GGA | GTG | 3842 |
| Ile | Val | Gly | Glu | Asp | Gly | Gln | Ala | Tyr | Val | Ser | Gly | Leu | Ser | Gly | Val | |
| | | | | 765 | | | | | 770 | | | | | 775 | | |
| CAA | AAA | TTA | ATC | GCT | TCG | TGG | GGG | AAT | AAT | CCC | TCC | GAT | ACT | TGT | ACA | 3890 |
| Gln | Lys | Leu | Ile | Ala | Ser | Trp | Gly | Asn | Asn | Pro | Ser | Asp | Thr | Cys | Thr | |
| | | | 780 | | | | | 785 | | | | | 790 | | | |

| | | | | | | | | | | | | | | | | |
|---|---|---|---|---|---|---|---|---|---|---|---|---|---|---|---|---|
| GTT | TTT | TAC | TCT | CTT | CCC | GAT | AAA | AAC | AAA | GGT | CAG | ATT | AGC | TTT | TTA | 3938 |
| Val | Phe | Tyr | Ser | Leu | Pro | Asp | Lys | Asn | Lys | Gly | Gln | Ile | Ser | Phe | Leu | |
| | 795 | | | | | 800 | | | | | 805 | | | | | |
| AAT | GGA | GTG | TGC | AAA | TGA | ATG | AAT | CAG | TAT | AAT | TCG | TCA | ATA | CCT | AAG | 3986 |
| Asn | Gly | Val | Cys | Lys | | Met | Asn | Gln | Tyr | Asn | Ser | Ser | Ile | Pro | Lys | |
| 810 | | | | | | 1 | | | 5 | | | | | | 10 | |
| TTC | ATT | GTC | TCT | GTT | TTT | CTG | ATT | GTT | ACT | GGT | TTT | TTC | AGC | TCA | ACT | 4034 |
| Phe | Ile | Val | Ser | Val | Phe | Leu | Ile | Val | Thr | Gly | Phe | Phe | Ser | Ser | Thr | |
| | | | | 15 | | | | | 20 | | | | | 25 | | |
| ATT | AAA | GCA | CAA | GAA | CTT | AAA | TTA | ATG | ATT | AAA | ATA | AAT | GAG | GCT | GTT | 4082 |
| Ile | Lys | Ala | Gln | Glu | Leu | Lys | Leu | Met | Ile | Lys | Ile | Asn | Glu | Ala | Val | |
| | | | 30 | | | | | 35 | | | | | 40 | | | |
| TTT | TAT | GAC | CGT | ATT | ACA | AGT | AAT | AAA | ATA | ATA | GGT | ACG | GGG | CAT | CTA | 4130 |
| Phe | Tyr | Asp | Arg | Ile | Thr | Ser | Asn | Lys | Ile | Ile | Gly | Thr | Gly | His | Leu | |
| | | 45 | | | | | 50 | | | | | 55 | | | | |
| TTT | AAC | AGA | GAG | GGA | AAA | AAA | ATC | CTC | ATT | AGT | TCA | AGT | TTA | GAA | AAA | 4178 |
| Phe | Asn | Arg | Glu | Gly | Lys | Lys | Ile | Leu | Ile | Ser | Ser | Ser | Leu | Glu | Lys | |
| | 60 | | | | | 65 | | | | | 70 | | | | | |
| ATT | AAA | AAT | ACC | CCA | GGG | GCA | TAT | ATT | ATT | AGA | GGT | CAG | AAT | AAC | TCA | 4226 |
| Ile | Lys | Asn | Thr | Pro | Gly | Ala | Tyr | Ile | Ile | Arg | Gly | Gln | Asn | Asn | Ser | |
| 75 | | | | | 80 | | | | | 85 | | | | | 90 | |
| GCC | CAT | AAG | CTT | AGG | ATA | AGA | ATA | GGT | GGA | GAA | GAC | TGG | CAA | CCA | GAT | 4274 |
| Ala | His | Lys | Leu | Arg | Ile | Arg | Ile | Gly | Gly | Glu | Asp | Trp | Gln | Pro | Asp | |
| | | | | 95 | | | | | 100 | | | | | 105 | | |
| AAT | TCA | GGT | ATT | GGT | ATG | GTA | TCT | CAT | TCT | GAT | TTT | ACT | AAT | GAA | TTT | 4322 |
| Asn | Ser | Gly | Ile | Gly | Met | Val | Ser | His | Ser | Asp | Phe | Thr | Asn | Glu | Phe | |
| | | | 110 | | | | | 115 | | | | | 120 | | | |
| AAT | ATT | TAT | TTT | TTT | GGG | AAT | GGA | GAC | ATT | CCT | GTT | GAC | ACA | TAT | TTA | 4370 |
| Asn | Ile | Tyr | Phe | Phe | Gly | Asn | Gly | Asp | Ile | Pro | Val | Asp | Thr | Tyr | Leu | |
| | | 125 | | | | | 130 | | | | | 135 | | | | |
| ATA | AGC | ATA | TAT | GCG | ACA | GAA | ATT | GAA | TTA | TAATAA | | | | | | 4406 |
| Ile | Ser | Ile | Tyr | Ala | Thr | Glu | Ile | Glu | Leu | | | | | | | |
| 140 | | | | | 145 | | | | | | | | | | | |

( 2 ) INFORMATION FOR SEQ ID NO:40:

( i ) SEQUENCE CHARACTERISTICS:
        ( A ) LENGTH: 165 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 40:

| | | | | | | | | | | | | | | | |
|---|---|---|---|---|---|---|---|---|---|---|---|---|---|---|---|
| Met | Arg | Lys | Ser | Ala | Ser | Ala | Val | Ala | Val | Leu | Ala | Leu | Ile | Ala | Cys |
| 1 | | | | 5 | | | | | 10 | | | | | 15 | |
| Gly | Ser | Ala | His | Ala | Ala | Gly | Phe | Val | Gly | Asn | Lys | Ala | Val | Val | Gln |
| | | | 20 | | | | | 25 | | | | | 30 | | |
| Ala | Ala | Val | Thr | Ile | Ala | Ala | Gln | Asn | Thr | Thr | Ser | Ala | Asn | Trp | Ser |
| | | | 35 | | | | 40 | | | | | 45 | | | |
| Gln | Asp | Pro | Gly | Phe | Thr | Gly | Pro | Ala | Val | Ala | Ala | Gly | Gln | Lys | Val |
| | | 50 | | | | 55 | | | | | 60 | | | | |
| Gly | Thr | Leu | Ser | Ile | Thr | Ala | Thr | Gly | Pro | His | Asn | Ser | Val | Ser | Ile |
| 65 | | | | | 70 | | | | 75 | | | | | | 80 |
| Ala | Gly | Lys | Gly | Ala | Ser | Val | Ser | Gly | Gly | Val | Ala | Thr | Val | Pro | Phe |
| | | | | 85 | | | | | 90 | | | | | 95 | |
| Val | Asp | Gly | Gln | Gly | Gln | Pro | Val | Phe | Arg | Gly | Arg | Ile | Gln | Gly | Ala |
| | | | 100 | | | | | 105 | | | | | 110 | | |
| Asn | Ile | Asn | Asp | Gln | Ala | Asn | Thr | Gly | Ile | Asp | Gly | Leu | Ala | Gly | Trp |
| | | 115 | | | | | 120 | | | | | 125 | | | |

```
Arg  Val  Ala  Ser  Ser  Gln  Glu  Thr  Leu  Asn  Val  Pro  Val  Thr  Thr  Phe
     130                 135                      140

Gly  Lys  Ser  Thr  Leu  Pro  Ala  Gly  Thr  Phe  Thr  Ala  Thr  Phe  Tyr  Val
145                      150                      155                      160

Gln  Gln  Tyr  Gln  Asn
                    165
```

( 2 ) INFORMATION FOR SEQ ID NO:41:

( i ) SEQUENCE CHARACTERISTICS:
        ( A ) LENGTH: 246 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 41:

```
Met  Tyr  Ile  Leu  Asn  Lys  Phe  Ile  Arg  Arg  Thr  Val  Ile  Phe  Phe  Phe
 1              5                        10                       15

Phe  Cys  Tyr  Leu  Pro  Ile  Ala  Ser  Ser  Glu  Ser  Lys  Lys  Ile  Glu  Gln
               20                      25                       30

Pro  Leu  Leu  Thr  Gln  Lys  Tyr  Tyr  Gly  Leu  Arg  Leu  Gly  Thr  Thr  Arg
          35                      40                       45

Val  Ile  Tyr  Lys  Glu  Asp  Ala  Pro  Ser  Thr  Ser  Phe  Trp  Ile  Met  Asn
     50                      55                       60

Glu  Lys  Glu  Tyr  Pro  Ile  Leu  Val  Gln  Thr  Gln  Val  Tyr  Asn  Asp  Asp
65                            70                       75                       80

Lys  Ser  Ser  Lys  Ala  Pro  Phe  Ile  Val  Thr  Pro  Pro  Ile  Leu  Lys  Val
                    85                       90                       95

Glu  Ser  Asn  Ala  Arg  Thr  Arg  Leu  Lys  Val  Ile  Pro  Thr  Ser  Asn  Leu
               100                      105                      110

Phe  Asn  Lys  Asn  Glu  Glu  Ser  Leu  Tyr  Trp  Leu  Cys  Val  Lys  Gly  Val
          115                      120                      125

Pro  Pro  Leu  Asn  Asp  Asn  Glu  Ser  Asn  Asn  Lys  Asn  Asn  Ile  Thr  Thr
     130                      135                      140

Asn  Leu  Asn  Val  Asn  Val  Val  Thr  Asn  Ser  Cys  Ile  Lys  Leu  Ile  Thr
145                      150                      155                      160

Arg  Pro  Lys  Thr  Ile  Asp  Leu  Thr  Thr  Met  Glu  Ile  Ala  Asp  Lys  Leu
                    165                      170                      175

Lys  Leu  Glu  Arg  Lys  Gly  Asn  Ser  Ile  Val  Ile  Lys  Asn  Pro  Thr  Ser
               180                      185                      190

Ser  Tyr  Val  Asn  Ile  Ala  Asn  Ile  Lys  Ser  Gly  Asn  Leu  Ser  Phe  Asn
          195                      200                      205

Ile  Pro  Asn  Gly  Tyr  Ile  Glu  Pro  Phe  Gly  Tyr  Ala  Gln  Leu  Pro  Gly
     210                      215                      220

Gly  Val  His  Ser  Lys  Ile  Thr  Leu  Thr  Ile  Leu  Asp  Asp  Asn  Gly  Ala
225                      230                      235                      240

Glu  Ile  Ile  Arg  Asp  Tyr
                    245
```

( 2 ) INFORMATION FOR SEQ ID NO:42:

( i ) SEQUENCE CHARACTERISTICS:
        ( A ) LENGTH: 814 amino acids
        ( B ) TYPE: amino acid
        ( D ) TOPOLOGY: linear ( i i ) MOLECULE TYPE: protein ( x i ) SEQUENCE DESCRIPTION: SEQ ID NO:42:

| | | | | | | | | | | | | | | | |
|---|---|---|---|---|---|---|---|---|---|---|---|---|---|---|---|
| Met<br>1 | Lys | Lys | Thr | Thr<br>5 | Ile | Thr | Leu | Phe | Val<br>10 | Leu | Thr | Ser | Val | Phe<br>15 | His |
| Ser | Gly | Asn | Val<br>20 | Phe | Ser | Arg | Gln | Tyr<br>25 | Asn | Phe | Asp | Tyr | Gly<br>30 | Ser | Leu |
| Ser | Leu | Pro<br>35 | Pro | Gly | Glu | Asn | Ala<br>40 | Ser | Phe | Leu | Ser | Val<br>45 | Glu | Thr | Leu |
| Pro | Gly<br>50 | Asn | Tyr | Val | Val | Asp<br>55 | Val | Tyr | Leu | Asn | Asn<br>60 | Gln | Leu | Lys | Glu |
| Thr<br>65 | Thr | Glu | Leu | Tyr | Phe<br>70 | Lys | Ser | Met | Thr | Gln<br>75 | Thr | Leu | Glu | Pro | Cys<br>80 |
| Leu | Thr | Lys | Glu | Lys<br>85 | Leu | Ile | Lys | Tyr | Gly<br>90 | Ile | Ala | Ile | Gln | Glu<br>95 | Leu |
| His | Gly | Leu | Gln<br>100 | Phe | Asp | Asn | Glu | Gln<br>105 | Cys | Val | Leu | Leu | Glu<br>110 | His | Ser |
| Pro | Leu | Lys<br>115 | Tyr | Thr | Tyr | Asn | Ala<br>120 | Ala | Asn | Gln | Ser | Leu<br>125 | Leu | Leu | Asn |
| Ala | Pro<br>130 | Ser | Lys | Ile | Leu | Ser<br>135 | Pro | Ile | Asp | Ser | Glu<br>140 | Ile | Ala | Asp | Glu |
| Asn<br>145 | Ile | Trp | Asp | Asp | Gly<br>150 | Ile | Asn | Ala | Phe | Leu<br>155 | Leu | Asn | Tyr | Arg | Ala<br>160 |
| Asn | Tyr | Leu | His | Ser<br>165 | Lys | Val | Gly | Gly | Glu<br>170 | Asp | Ser | Tyr | Phe | Gly<br>175 | Gln |
| Ile | Gln | Pro | Gly<br>180 | Phe | Asn | Phe | Gly | Pro<br>185 | Trp | Arg | Leu | Arg | Asn<br>190 | Leu | Ser |
| Ser | Trp | Gln<br>195 | Asn | Leu | Ser | Ser | Glu<br>200 | Lys | Lys | Phe | Glu | Ser<br>205 | Ala | Tyr | Ile |
| Tyr | Ala<br>210 | Glu | Arg | Gly | Leu | Lys<br>215 | Lys | Ile | Lys | Ser | Lys<br>220 | Leu | Thr | Val | Gly |
| Asp<br>225 | Lys | Tyr | Thr | Ser | Ala<br>230 | Asp | Leu | Phe | Asp | Ser<br>235 | Val | Pro | Phe | Arg | Gly<br>240 |
| Phe | Ser | Leu | Asn | Lys<br>245 | Asp | Glu | Ser | Met | Ile<br>250 | Pro | Phe | Ser | Gln | Arg<br>255 | Thr |
| Tyr | Tyr | Pro | Thr<br>260 | Ile | Arg | Gly | Ile | Ala<br>265 | Lys | Thr | Asn | Ala | Thr<br>270 | Val | Glu |
| Val | Arg | Gln<br>275 | Asn | Gly | Tyr | Leu | Ile<br>280 | Tyr | Ser | Thr | Ser | Val<br>285 | Pro | Pro | Gly |
| Gln | Phe<br>290 | Glu | Ile | Gly | Arg | Glu<br>295 | Gln | Ile | Ala | Asp | Leu<br>300 | Gly | Val | Gly | Val |
| Gly<br>305 | Val | Leu | Asp | Val | Ser<br>310 | Ile | Tyr | Glu | Lys | Asn<br>315 | Gly | Gln | Val | Gln | Asn<br>320 |
| Tyr | Thr | Val | Pro | Tyr<br>325 | Ser | Thr | Pro | Val | Leu<br>330 | Ser | Leu | Pro | Asp | Gly<br>335 | Tyr |
| Ser | Lys | Tyr | Ser<br>340 | Val | Thr | Ile | Gly | Arg<br>345 | Tyr | Arg | Glu | Val | Asn<br>350 | Asn | Asp |
| Tyr | Ile | Asp<br>355 | Pro | Val | Phe | Phe | Glu<br>360 | Gly | Thr | Tyr | Ile | Tyr<br>365 | Gly | Leu | Pro<br>368 |
| Tyr | Gly<br>370 | Phe | Thr | Leu | Phe | Gly<br>375 | Gly | Val | Gln | Trp | Val<br>380 | Asn | Ile | Tyr | Asn |
| Ser<br>385 | Tyr | Ala | Ile | Gly | Ala<br>390 | Ser | Lys | Asp | Ile | Gly<br>395 | Glu | Tyr | Gly | Ala | Leu<br>400 |
| Ser | Phe | Asp | Trp | Lys<br>405 | Thr | Ser | Val | Ser | Lys<br>410 | Thr | Asp | Thr | Ser | Asn<br>415 | Glu |

```
Asn Gly His Ala Tyr Gly Ile Arg Tyr Asn Lys Asn Ile Ala Gln Thr
            420             425             430

Asn Thr Glu Val Ser Leu Ala Ser His Tyr Tyr Tyr Ser Lys Asn Tyr
        435             440             445

Arg Thr Phe Ser Glu Ala Ile His Ser Ser Glu His Asp Glu Phe Tyr
    450             455             460

Asp Lys Asn Lys Lys Ser Thr Thr Ser Met Leu Leu Ser Gln Ala Leu
465             470             475                         480

Gly Ser Leu Gly Ser Val Asn Leu Ser Tyr Asn Tyr Asp Lys Tyr Trp
            485             490             495

Lys His Glu Gly Lys Lys Ser Ile Ile Ala Ser Tyr Gly Lys Asn Leu
        500             505             510

Asn Gly Val Ser Leu Ser Leu Ser Tyr Thr Lys Ser Thr Ser Lys Ile
        515             520             525

Ser Glu Glu Asn Glu Asp Leu Phe Ser Phe Leu Leu Ser Val Pro Leu
        530             535             540

Gln Lys Leu Thr Asn His Glu Met Tyr Ala Thr Tyr Gln Asn Ser Ser
545             550             555                         560

Ser Ser Lys His Asp Met Asn His Asp Leu Gly Ile Thr Gly Val Ala
                565             570             575

Phe Asn Ser Gln Leu Thr Trp Gln Ala Arg Gly Gln Ile Glu Asp Lys
            580             585             590

Ser Lys Asn Gln Lys Ala Thr Phe Leu Asn Ala Ser Trp Arg Gly Thr
        595             600             605

Tyr Gly Glu Ile Gly Ala Asn Tyr Ser His Asn Glu Ile Asn Arg Asp
        610             615             620

Ile Gly Met Asn Val Ser Gly Gly Val Ile Ala His Ser Ser Gly Ile
625             630             635                         640

Thr Phe Gly His Ser Ile Ser Asp Thr Ala Ala Leu Val Glu Ala Lys
                645             650             655

Gly Val Ser Gly Ala Lys Val Leu Gly Leu Pro Gly Val Ile Thr Asp
            660             665             670

Phe Arg Gly Tyr Thr Ile Ser Ser Tyr Leu Thr Pro Tyr Met Asn Asn
        675             680             685

Phe Ile Ser Ile Asp Pro Thr Thr Leu Pro Ile Asn Thr Asp Ile Arg
    690             695             700

Gln Thr Asp Ile Gln Val Val Pro Thr Glu Gly Ala Ile Val Lys Ala
705             710             715             720

Val Tyr Lys Thr Ser Val Gly Thr Asn Ala Leu Ile Arg Ile Thr Arg
            725             730             735

Thr Asn Gly Lys Pro Leu Ala Leu Gly Thr Val Leu Ser Leu Lys Asn
        740             745             750

Asn Asp Gly Val Ile Gln Ser Thr Ser Ile Val Gly Glu Asp Gly Gln
        755             760             765

Ala Tyr Val Ser Gly Leu Ser Gly Val Gln Lys Leu Ile Ala Ser Trp
    770             775             780

Gly Asn Asn Pro Ser Asp Thr Cys Thr Val Phe Tyr Ser Leu Pro Asp
785             790             795             800

Lys Asn Lys Gly Gln Ile Ser Phe Leu Asn Gly Val Cys Lys
                805             810
```

( 2 ) INFORMATION FOR SEQ ID NO:43:

( i ) SEQUENCE CHARACTERISTICS:
        ( A ) LENGTH: 148 amino acids ( B ) TYPE: amino acid
( D ) TOPOLOGY: linear ( i i ) MOLECULE TYPE: protein ( x i ) SEQUENCE DESCRIPTION: SEQ ID NO:43:

```
Met Asn Gln Tyr Asn Ser Ser Ile Pro Lys Phe Ile Val Ser Val Phe
 1               5                  10                 15

Leu Ile Val Thr Gly Phe Phe Ser Ser Thr Ile Lys Ala Gln Glu Leu
            20                  25                 30

Lys Leu Met Ile Lys Ile Asn Glu Ala Val Phe Tyr Asp Arg Ile Thr
        35                  40                 45

Ser Asn Lys Ile Ile Gly Thr Gly His Leu Phe Asn Arg Glu Gly Lys
    50                  55                 60

Lys Ile Leu Ile Ser Ser Ser Leu Glu Lys Ile Lys Asn Thr Pro Gly
65                  70                 75                  80

Ala Tyr Ile Ile Arg Gly Gln Asn Asn Ser Ala His Lys Leu Arg Ile
                85                  90                 95

Arg Ile Gly Gly Glu Asp Trp Gln Pro Asp Asn Ser Gly Ile Gly Met
            100                 105                110

Val Ser His Ser Asp Phe Thr Asn Glu Phe Asn Ile Tyr Phe Phe Gly
        115                 120                125

Asn Gly Asp Ile Pro Val Asp Thr Tyr Leu Ile Ser Ile Tyr Ala Thr
    130                 135                140

Glu Ile Glu Leu
145
```

( 2 ) INFORMATION FOR SEQ ID NO:44:

( i ) SEQUENCE CHARACTERISTICS:
( A ) LENGTH: 675 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 106..672

( x i ) SEQUENCE DESCRIPTION: SEQ ID NO:44:

```
TCACCCACCC ATTTCTGATT CGGGCCACTG GCGTAAAAGC CCTGCTTCAG CAGATTCTCT           60

GGACTGGCAG ACCATGTTCG CGGTAACTGA CTGGACTGAT CTTCC GTG AAG CTT              114
                                                 Val Lys Leu
                                                  1

TCG CCC GCA GCA CTG CCG GCG CAG GCT GGC CGC TAC GGT TTT TAT GTT            162
Ser Pro Ala Ala Leu Pro Ala Gln Ala Gly Arg Tyr Gly Phe Tyr Val
     5               10                 15

ATA CAC CCG TCC CTG AGC ACG AAG CTC ATC CGT CAG GCG TGG CGT ACC            210
Ile His Pro Ser Leu Ser Thr Lys Leu Ile Arg Gln Ala Trp Arg Thr
 20              25                  30                 35

GTA GCG CTG TTT TGC GTC ACT GAA TGC CTC CCG TAC GAC GTT ATC ACA            258
Val Ala Leu Phe Cys Val Thr Glu Cys Leu Pro Tyr Asp Val Ile Thr
             40                  45                 50

GAC AAG TCG GAA CTG CTG ACG CCG GAC GTA CCA GCT GTT ACG GGC AAC            306
Asp Lys Ser Glu Leu Leu Thr Pro Asp Val Pro Ala Val Thr Gly Asn
         55                  60                 65

CTG AAG TAC ACG GCA TAT GGC TTT GAT ACT GAA CTC AGC CTG ATG TTT            354
Leu Lys Tyr Thr Ala Tyr Gly Phe Asp Thr Glu Leu Ser Leu Met Phe
     70                  75                 80

TTC GAT GAA GAC ATA CTT CAT TTC AGG CGT TTC GCG AAG TAT GTC GCG            402
Phe Asp Glu Asp Ile Leu His Phe Arg Arg Phe Ala Lys Tyr Val Ala
```

|     |     |     |     |     | 85  |     |     |     |     | 90  |     |     |     |     | 95  |     |     |
|-----|-----|-----|-----|-----|-----|-----|-----|-----|-----|-----|-----|-----|-----|-----|-----|-----|-----|
| ACC | ATT | CTG | GAG | AAT | GGT | CAG | TTC | CTC | ATC | CCG | TTC | TGC | CAG | TTG | ACG | | 450 |
| Thr | Ile | Leu | Glu | Asn | Gly | Gln | Phe | Leu | Ile | Pro | Phe | Cys | Gln | Leu | Thr | | |
| 100 |     |     |     |     | 105 |     |     |     |     | 110 |     |     |     |     | 115 | | |
| CTT | CAG | ACG | GAC | GAT | TTC | TGC | GGA | CAT | CTC | CTG | TTC | GCG | TTC | AGA | AGA | | 498 |
| Leu | Gln | Thr | Asp | Asp | Phe | Cys | Gly | His | Leu | Leu | Phe | Ala | Phe | Arg | Arg | | |
|     |     |     | 120 |     |     |     |     |     | 125 |     |     |     |     | 130 |     | | |
| AGA | GAG | CTG | ATT | TTG | CTG | TTT | GCT | TCG | CCA | GTT | GTA | GAG | CTG | CGA | TTC | | 546 |
| Arg | Glu | Leu | Ile | Leu | Leu | Phe | Ala | Ser | Pro | Val | Val | Glu | Leu | Arg | Phe | | |
|     |     |     | 135 |     |     |     |     | 140 |     |     |     |     | 145 |     |     | | |
| ATA | CAG | GTT | AAG | CTC | GCT | GGT | AGC | CGC | AGC | CAT | CCC | AAT | GCG | TTA | GCC | | 594 |
| Ile | Gln | Val | Lys | Leu | Ala | Gly | Ser | Arg | Ser | His | Pro | Asn | Ala | Leu | Ala | | |
|     |     | 150 |     |     |     |     | 155 |     |     |     |     | 160 |     |     |     | | |
| AGT | TTC | AAG | GCT | TCG | TCG | CGA | AAT | TCA | GGC | GTA | TGT | TGC | TTG | CAT | GGC | | 642 |
| Ser | Phe | Lys | Ala | Ser | Ser | Arg | Asn | Ser | Gly | Val | Cys | Cys | Leu | His | Gly | | |
|     | 165 |     |     |     |     | 170 |     |     |     |     | 175 |     |     |     |     | | |
| TTT | TTG | GTG | GTT | GAT | GCT | GCT | TTT | GTC | ATG | TGA |     |     |     |     |     | | 675 |
| Phe | Leu | Val | Val | Asp | Ala | Ala | Phe | Val | Met |     |     |     |     |     |     | | |
| 180 |     |     |     |     | 185 |     |     |     |     |     |     |     |     |     |     | | |

( 2 ) INFORMATION FOR SEQ ID NO:45:

( i ) SEQUENCE CHARACTERISTICS:
        ( A ) LENGTH: 189 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

| Val | Lys | Leu | Ser | Pro | Ala | Ala | Leu | Pro | Ala | Gln | Ala | Gly | Arg | Tyr | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Phe | Tyr | Val | Ile | His | Pro | Ser | Leu | Ser | Thr | Lys | Leu | Ile | Arg | Gln | Ala |
|     |     |     | 20  |     |     |     |     | 25  |     |     |     |     | 30  |     |     |
| Trp | Arg | Thr | Val | Ala | Leu | Phe | Cys | Val | Thr | Glu | Cys | Leu | Pro | Tyr | Asp |
|     |     | 35  |     |     |     |     | 40  |     |     |     |     | 45  |     |     |     |
| Val | Ile | Thr | Asp | Lys | Ser | Glu | Leu | Leu | Thr | Pro | Asp | Val | Pro | Ala | Val |
|     | 50  |     |     |     |     | 55  |     |     |     |     | 60  |     |     |     |     |
| Thr | Gly | Asn | Leu | Lys | Tyr | Thr | Ala | Tyr | Gly | Phe | Asp | Thr | Glu | Leu | Ser |
| 65  |     |     |     |     | 70  |     |     |     |     | 75  |     |     |     |     | 80  |
| Leu | Met | Phe | Phe | Asp | Glu | Asp | Ile | Leu | His | Phe | Arg | Arg | Phe | Ala | Lys |
|     |     |     |     | 85  |     |     |     |     | 90  |     |     |     |     | 95  |     |
| Tyr | Val | Ala | Thr | Ile | Leu | Gln | Asn | Gly | Gln | Phe | Leu | Ile | Pro | Phe | Cys |
|     |     |     | 100 |     |     |     |     | 105 |     |     |     |     | 110 |     |     |
| Gln | Leu | Thr | Leu | Gln | Thr | Asp | Asp | Phe | Cys | Gly | His | Leu | Leu | Phe | Ala |
|     |     | 115 |     |     |     |     | 120 |     |     |     |     | 125 |     |     |     |
| Phe | Arg | Arg | Arg | Glu | Leu | Ile | Leu | Leu | Phe | Ala | Ser | Pro | Val | Val | Glu |
|     | 130 |     |     |     |     | 135 |     |     |     |     | 140 |     |     |     |     |
| Leu | Arg | Phe | Ile | Gln | Val | Lys | Leu | Ala | Gly | Ser | Arg | Ser | His | Pro | Asn |
| 145 |     |     |     |     | 150 |     |     |     |     | 155 |     |     |     |     | 160 |
| Ala | Leu | Ala | Ser | Phe | Lys | Ala | Ser | Ser | Arg | Asn | Ser | Gly | Val | Cys | Cys |
|     |     |     |     | 165 |     |     |     |     | 170 |     |     |     |     | 175 |     |
| Leu | His | Gly | Phe | Leu | Val | Val | Asp | Ala | Ala | Phe | Val | Met |     |     |     |
|     |     |     | 180 |     |     |     |     | 185 |     |     |     |     |     |     |     |

( 2 ) INFORMATION FOR SEQ ID NO:46:

( i ) SEQUENCE CHARACTERISTICS:
        ( A ) LENGTH: 675 base pairs
        ( B ) TYPE: nucleic acid ( C ) STRANDEDNESS: single
( D ) TOPOLOGY: linear ( i x ) FEATURE:
( A ) NAME/KEY: CDS
( B ) LOCATION: 97..673

( x i ) SEQUENCE DESCRIPTION: SEQ ID NO:46:

```
TCACATGACA AAAGCAGCAT CAACCACCAA AAAGCCATGC AAGCAACATA CGCCTGAATT                60

TCGCGACGAA GCCTTGAAAC TGGCTAACGC ATTGGG ATG GCT GCG GCT ACC AGC                 114
                                        Met Ala Ala Ala Thr Ser
                                        1               5

GAG CTT AAC CTG TAT GAA TCG CAG CTC TAC AAC TGG CGA AGC AAA CAG                 162
Glu Leu Asn Leu Tyr Glu Ser Gln Leu Tyr Asn Trp Arg Ser Lys Gln
            10                  15                  20

CAA AAT CAG CTC TCT TCT TCT GAA CGC GAA CAG GAG ATG TCC GCA GAA                 210
Gln Asn Gln Leu Ser Ser Ser Glu Arg Glu Gln Glu Met Ser Ala Glu
        25                  30                  35

ATC GTC CGT CTG AAG CGT CAA CTG GCA GAA CGG GAT GAG GAA CTG ACC                 258
Ile Val Arg Leu Lys Arg Gln Leu Ala Glu Arg Asp Glu Glu Leu Thr
    40                  45                  50

ATT CTC CAG AAT GGT CGC GAC ATA CTT CGC GAA ACG CCT GAA ATG AAG                 306
Ile Leu Gln Asn Gly Arg Asp Ile Leu Arg Glu Thr Pro Glu Met Lys
55                  60                  65                  70

TAT GTC TTC ATC AAA AAA CAT CAG GCT GAG TTC AGT ATC AAA GCC ATA                 354
Tyr Val Phe Ile Lys Lys His Gln Ala Glu Phe Ser Ile Lys Ala Ile
                75                  80                  85

TGC CGT GTA CTT CAG GTT GCC CGT AAC AGC TGG TAC GTC CGG CGT CAG                 402
Cys Arg Val Leu Gln Val Ala Arg Asn Ser Trp Tyr Val Arg Arg Gln
            90                  95                  100

CAG TTC CGA CTT GTC TGT GAT AAC GTC GTA CGG GAG GCA TTC AGT GAC                 450
Gln Phe Arg Leu Val Cys Asp Asn Val Val Arg Glu Ala Phe Ser Asp
        105                 110                 115

GCA AAA CAG CGC TAC GGT ACG CCA CGC CTG ACG GAT GAG GTT CGT GCT                 498
Ala Lys Gln Arg Tyr Gly Thr Pro Arg Leu Thr Asp Glu Val Arg Ala
    120                 125                 130

CAG GGA CGG GTG TAT AAC ATA AAA ACC GTA GCG GCC AGC CTG CGC CGG                 546
Gln Gly Arg Val Tyr Asn Ile Lys Thr Val Ala Ala Ser Leu Arg Arg
135                 140                 145                 150

CAG TGC TGC GGG CGA AAG CTT CAC GGA AGA TCA GTC CAG TCA GTT ACC                 594
Gln Cys Cys Gly Arg Lys Leu His Gly Arg Ser Val Gln Ser Val Thr
            155                 160                 165

GCG AAC ATG GTC TGC CAG TCC AGA GAA TCT GCT GAA GCA GGG CTT TTA                 642
Ala Asn Met Val Cys Gln Ser Arg Glu Ser Ala Glu Ala Gly Leu Leu
        170                 175                 180

CGC CAG TGG CCC GAA TCA GAA ATG GGT GGG T GA                                    675
Arg Gln Trp Pro Glu Ser Glu Met Gly Gly
    185                 190
```

( 2 ) INFORMATION FOR SEQ ID NO:47:

( i ) SEQUENCE CHARACTERISTICS:
( A ) LENGTH: 192 amino acids
( B ) TYPE: amino acid
( D ) TOPOLOGY: linear ( i i ) MOLECULE TYPE: protein ( x i ) SEQUENCE DESCRIPTION: SEQ ID NO:47:

```
Met Ala Ala Ala Thr Ser Glu Leu Asn Leu Tyr Glu Ser Gln Leu Tyr
1               5                   10                  15

Asn Trp Arg Ser Lys Gln Gln Asn Gln Leu Ser Ser Ser Glu Arg Glu
            20                  25                  30
```

| | | | | | | | | | | | | | | | |
|---|---|---|---|---|---|---|---|---|---|---|---|---|---|---|---|
|Gln|Glu|Met|Ser|Ala|Glu|Ile|Val|Arg|Leu|Lys|Arg|Gln|Leu|Ala|Glu|
| | |35| | | |40| | | |45| | | | | |
|Arg|Asp|Glu|Glu|Leu|Thr|Ile|Leu|Gln|Asn|Gly|Arg|Asp|Ile|Leu|Arg|
| |50| | | | |55| | | |60| | | | | |
|Glu|Thr|Pro|Glu|Met|Lys|Tyr|Val|Phe|Ile|Glu|Lys|His|Gln|Ala|Glu|
|65| | | | |70| | | |75| | | | | |80|
|Phe|Ser|Ile|Lys|Ala|Ile|Cys|Arg|Val|Leu|Gln|Val|Ala|Arg|Asn|Ser|
| | | | |85| | | | |90| | | | |95| |
|Trp|Tyr|Val|Arg|Arg|Gln|Gln|Phe|Arg|Leu|Val|Cys|Asp|Asn|Val|Val|
| | | |100| | | | |105| | | | |110| | |
|Arg|Glu|Ala|Phe|Ser|Asp|Ala|Lys|Gln|Arg|Tyr|Gly|Thr|Pro|Arg|Leu|
| | |115| | | | |120| | | | |125| | | |
|Thr|Asp|Glu|Val|Arg|Ala|Gln|Gly|Arg|Val|Tyr|Asn|Ile|Lys|Thr|Val|
| |130| | | | |135| | | | |140| | | | |
|Ala|Ala|Ser|Leu|Arg|Arg|Gln|Cys|Cys|Gly|Arg|Lys|Leu|His|Gly|Arg|
|145| | | | |150| | | | |155| | | | |160|
|Ser|Val|Gln|Ser|Val|Thr|Ala|Asn|Met|Val|Cys|Gln|Ser|Arg|Glu|Ser|
| | | | |165| | | | |170| | | | |175| |
|Ala|Glu|Ala|Gly|Leu|Leu|Arg|Gln|Trp|Pro|Glu|Ser|Glu|Met|Gly|Gly|
| | | |180| | | | |185| | | | |190| | |

( 2 ) INFORMATION FOR SEQ ID NO:48:

( i ) SEQUENCE CHARACTERISTICS:
        ( A ) LENGTH: 1126 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: join(3..23, 27..944, 948..1124)

( x i ) SEQUENCE DESCRIPTION: SEQ ID NO:48:

| | | | | | | | | | | | | | | | | |
|---|---|---|---|---|---|---|---|---|---|---|---|---|---|---|---|---|
|AC|CGG|GGT|TTA|TCG|CTT|TAC|CTT|TGA|CAG|CGT|TCA|TCT|TTC|CGA|CGG|47|
| |Arg|Gly|Leu|Ser|Leu|Tyr|Leu| |Gln|Arg|Ser|Ser|Phe|Arg|Arg| |
| |1| | | |5| | | |1| | | |5| | | |
|CGT|ACA|GTT|TAT|CGT|CGT|GGT|GAT|CGG|CCT|GTT|CTC|GGT|ATC|AGA|AAT|95|
|Arg|Thr|Val|Tyr|Arg|Arg|Gly|Asp|Arg|Pro|Val|Leu|Gly|Ile|Arg|Asn| |
| | |10| | | | |15| | | | |20| | | | |
|ACT|TTT|AAT|GCT|GGA|ACA|TAC|CAG|CAG|CGG|GCA|AAC|AAT|GGT|CCG|CAA|143|
|Thr|Phe|Asn|Ala|Gly|Thr|Tyr|Gln|Gln|Arg|Ala|Asn|Asn|Gly|Pro|Gln| |
| | |25| | | | |30| | | | |35| | | | |
|AAC|GGG|TCG|AAT|GTT|GTT|CAA|CCT|GAA|AGA|AGG|CGC|GCA|GTG|TAT|CGG|191|
|Asn|Gly|Ser|Asn|Val|Val|Gln|Pro|Glu|Arg|Arg|Arg|Ala|Val|Tyr|Arg| |
|40| | | | |45| | | | |50| | | | |55| |
|CAC|CAC|CCT|GCG|TTC|TTC|GGT|AAT|CGG|CTT|TTT|TGT|CGG|CGT|ATT|GCC|239|
|His|His|Pro|Ala|Phe|Phe|Gly|Asn|Arg|Leu|Phe|Cys|Arg|Arg|Ile|Ala| |
| | | | |60| | | | |65| | | | |70| | |
|CGG|CGC|CGG|GCG|ACC|ATT|GCC|AGC|GCC|ATT|ACC|TAT|ATG|ACC|GAG|AAA|287|
|Arg|Arg|Arg|Ala|Thr|Ile|Ala|Ser|Ala|Ile|Thr|Tyr|Met|Thr|Glu|Lys| |
| | | |75| | | | |80| | | | |85| | | |
|AAA|CTC|AGC|GGC|AAC|AGC|GAT|AGC|TTC|GGC|AAA|GGG|GAT|ATT|CGC|GGC|335|
|Lys|Leu|Ser|Gly|Asn|Ser|Asp|Ser|Phe|Gly|Lys|Gly|Asp|Ile|Arg|Gly| |
| | |90| | | | |95| | | | |100| | | | |
|GTC|GCG|GCG|CCG|GAG|GCG|GCA|AAC|AAC|GCC|TCT|GCC|TGC|GGC|TCC|TTC|383|
|Val|Ala|Ala|Pro|Glu|Ala|Ala|Asn|Asn|Ala|Ser|Ala|Cys|Gly|Ser|Phe| |
| |105| | | | |110| | | | |115| | | | | |

| | | | | | | | | | | | | | | | | |
|---|---|---|---|---|---|---|---|---|---|---|---|---|---|---|---|---|
| ATC | CCG | ATG | CTG | ACG | CTG | GGC | GTT | CCC | GGT | TCC | GGC | ACT | ACG | GCA | GTG | 431 |
| Ile | Pro | Met | Leu | Thr | Leu | Gly | Val | Pro | Gly | Ser | Gly | Thr | Thr | Ala | Val | |
| 120 | | | | 125 | | | | | 130 | | | | | | 135 | |
| ATG | ATG | GGG | GCG | CTG | ACG | CTG | TAC | AAC | ATC | ACG | CCA | GGC | CCG | GCG | ATG | 479 |
| Met | Met | Gly | Ala | Leu | Thr | Leu | Tyr | Asn | Ile | Thr | Pro | Gly | Pro | Ala | Met | |
| | | | | 140 | | | | | 145 | | | | | 150 | | |
| TTC | ACC | GAA | CAG | CCG | GAT | ATC | GTC | TGG | GGA | CTC | ATC | GCT | GCG | CTG | CTG | 527 |
| Phe | Tyr | Glu | Gln | Pro | Asp | Ile | Val | Trp | Gly | Leu | Ile | Ala | Ala | Leu | Leu | |
| | | | 155 | | | | | 160 | | | | | 165 | | | |
| ATT | GCG | AAC | GTG | ATG | CTG | CTG | ATC | ATG | AAT | ATC | CCG | TTG | ATC | GGT | CTG | 575 |
| Ile | Ala | Asn | Val | Met | Leu | Leu | Ile | Met | Asn | Ile | Pro | Leu | Ile | Gly | Leu | |
| | | 170 | | | | | 175 | | | | | 180 | | | | |
| TTC | ACC | CGT | ATG | CTC | ACC | ATT | CCG | CTG | TGG | TTC | CTG | GTA | CCC | GCC | ATC | 623 |
| Phe | Thr | Arg | Met | Leu | Thr | Ile | Pro | Leu | Trp | Phe | Leu | Val | Pro | Ala | Ile | |
| | 185 | | | | | 190 | | | | | 195 | | | | | |
| GCT | GCC | GTA | TCG | GCG | GTG | GGG | GTG | TAT | GCG | GTA | CAC | AGC | ACC | ACC | TTC | 671 |
| Ala | Ala | Val | Ser | Ala | Val | Gly | Val | Tyr | Ala | Val | His | Ser | Thr | Thr | Phe | |
| 200 | | | | | 205 | | | | | 210 | | | | | 215 | |
| GAT | CTG | GTG | CTG | ATG | GTC | GCG | CTC | GGC | GTG | TTA | GGG | TAC | ATT | TTA | CGT | 719 |
| Asp | Leu | Val | Leu | Met | Val | Ala | Leu | Gly | Val | Leu | Gly | Tyr | Ile | Leu | Arg | |
| | | | | 220 | | | | | 225 | | | | | 230 | | |
| AAA | ATG | CAC | TTC | CCC | ATG | TCA | CCG | CTG | ATC | CTG | GGG | TTC | GTA | CTG | GGG | 767 |
| Lys | Met | His | Phe | Pro | Met | Ser | Pro | Leu | Ile | Leu | Gly | Phe | Val | Leu | Gly | |
| | | | 235 | | | | | 240 | | | | | 245 | | | |
| GAA | ATG | CTG | GAG | CAG | AAC | CTG | CGT | CGC | GCA | CTC | TCC | ATC | AGT | AAC | GGC | 815 |
| Glu | Met | Leu | Glu | Gln | Asn | Leu | Arg | Arg | Ala | Leu | Ser | Ile | Ser | Asn | Gly | |
| | | 250 | | | | | 255 | | | | | 260 | | | | |
| AAT | ATG | GCG | ATT | TTG | TGG | CAA | AGC | GGC | GTT | GCC | AAA | GCC | CTG | CTG | ATC | 863 |
| Asn | Met | Ala | Ile | Leu | Trp | Gln | Ser | Gly | Val | Ala | Lys | Ala | Leu | Leu | Ile | |
| | 265 | | | | | 270 | | | | | 275 | | | | | |
| ATG | GCG | ATC | ATG | GTC | ATT | GTC | GTA | CCG | CCA | GTG | TTA | CGT | CTG | CTC | CGT | 911 |
| Met | Ala | Ile | Met | Val | Ile | Val | Val | Pro | Pro | Val | Leu | Arg | Leu | Leu | Arg | |
| 280 | | | | | 285 | | | | | 290 | | | | | 295 | |
| AAA | CAC | AGC | CGT | AAA | CCG | CAG | GTT | GAC | GCC | GGT | TAA | TTG | ACT | GCT | GAA | 959 |
| Lys | His | Ser | Arg | Lys | Pro | Gln | Val | Asp | Ala | Gly | | Leu | Thr | Ala | Glu | |
| | | | 300 | | | | | 305 | | | | 1 | | | | |
| ATA | CGT | TGT | ACT | TGT | CCG | GCC | TAC | GCG | CTC | ATG | TGT | CAG | GCC | GGG | CAC | 1007 |
| Ile | Arg | Cys | Thr | Cys | Pro | Ala | Tyr | Ala | Leu | Met | Cys | Gln | Ala | Gly | His | |
| 5 | | | | | 10 | | | | | 15 | | | | | 20 | |
| ATC | CCC | GCC | AGC | ATT | CAC | TTT | CCC | CAT | AAC | GCC | TCT | CAT | TTT | ACA | CCC | 1055 |
| Ile | Pro | Ala | Ser | Ile | His | Phe | Pro | His | Asn | Ala | Ser | His | Phe | Thr | Pro | |
| | | | | 25 | | | | | 30 | | | | | 35 | | |
| CTT | CTT | GCC | GTT | GTC | AGG | CTC | GTG | GCG | CCG | TTA | ACC | TCA | CCC | TTT | GCA | 1103 |
| Leu | Leu | Ala | Val | Val | Arg | Leu | Val | Ala | Pro | Leu | Thr | Ser | Pro | Phe | Ala | |
| | | | 40 | | | | | 45 | | | | 50 | | | | |
| TTG | TTA | AAT | ATT | TGT | TGT | TTT | TG | | | | | | | | | 1126 |
| Leu | Leu | Asn | Ile | Cys | Cys | Phe | | | | | | | | | | |
| | | 55 | | | | | | | | | | | | | | |

( 2 ) INFORMATION FOR SEQ ID NO:49:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:49:

Arg  Gly  Leu  Ser  Leu  Tyr  Leu
1                    5

(2) INFORMATION FOR SEQ ID NO:50:

(i) SEQUENCE CHARACTERISTICS:
        (A) LENGTH: 306 amino acids
        (B) TYPE: amino acid
        (D) TOPOLOGY: linear (ii) MOLECULE TYPE: protein (xi) SEQUENCE DESCRIPTION: SEQ ID NO:50:

```
Gln Arg Ser Ser Phe Arg Arg Arg Thr Val Tyr Arg Arg Gly Asp Arg
 1               5                  10                  15
Pro Val Leu Gly Ile Arg Asn Thr Phe Asn Ala Gly Thr Tyr Gln Gln
                20                  25                  30
Arg Ala Asn Asn Gly Pro Gln Asn Gly Ser Asn Val Val Gln Pro Glu
            35                  40                  45
Arg Arg Arg Ala Val Tyr Arg His His Pro Ala Phe Phe Gly Asn Arg
        50                  55                  60
Leu Phe Cys Arg Arg Ile Ala Arg Arg Arg Ala Thr Ile Ala Ser Ala
 65                  70                  75                  80
Ile Thr Tyr Met Thr Glu Lys Lys Leu Ser Gly Asn Ser Asp Ser Phe
                85                  90                  95
Gly Lys Gly Asp Ile Arg Gly Val Ala Ala Pro Glu Ala Ala Asn Asn
                100                 105                 110
Ala Ser Ala Cys Gly Ser Phe Ile Pro Met Leu Thr Leu Gly Val Pro
            115                 120                 125
Gly Ser Gly Thr Thr Ala Val Met Met Gly Ala Leu Thr Leu Tyr Asn
        130                 135                 140
Ile Thr Pro Gly Pro Ala Met Phe Tyr Glu Gln Pro Asp Ile Val Trp
145                 150                 155                 160
Gly Leu Ile Ala Ala Leu Leu Ile Ala Asn Val Met Leu Leu Ile Met
                165                 170                 175
Asn Ile Pro Leu Ile Gly Leu Phe Thr Arg Met Leu Thr Ile Pro Leu
                180                 185                 190
Trp Phe Leu Val Pro Ala Ile Ala Ala Val Ser Ala Val Gly Val Tyr
            195                 200                 205
Ala Val His Ser Thr Thr Phe Asp Leu Val Leu Met Val Ala Leu Gly
        210                 215                 220
Val Leu Gly Tyr Ile Leu Arg Lys Met His Phe Pro Met Ser Pro Leu
225                 230                 235                 240
Ile Leu Gly Phe Val Leu Gly Glu Met Leu Glu Gln Asn Leu Arg Arg
                245                 250                 255
Ala Leu Ser Ile Ser Asn Gly Asn Met Ala Ile Leu Trp Gln Ser Gly
                260                 265                 270
Val Ala Lys Ala Leu Leu Ile Met Ala Ile Met Val Ile Val Val Pro
            275                 280                 285
Pro Val Leu Arg Leu Leu Arg Lys His Ser Arg Lys Pro Gln Val Asp
        290                 295                 300
Ala Gly
305
```

(2) INFORMATION FOR SEQ ID NO:51:

(i) SEQUENCE CHARACTERISTICS:
        (A) LENGTH: 59 amino acids
        (B) TYPE: amino acid
        (D) TOPOLOGY: linear (ii) MOLECULE TYPE: protein ( x i ) SEQUENCE DESCRIPTION: SEQ ID NO:51:

| Leu | Thr | Ala | Glu | Ile | Arg | Cys | Thr | Cys | Pro | Ala | Tyr | Ala | Leu | Met | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gln | Ala | Gly | His | Ile | Pro | Ala | Ser | Ile | His | Phe | Pro | His | Asn | Ala | Ser |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| His | Phe | Thr | Pro | Leu | Leu | Ala | Val | Val | Arg | Leu | Val | Ala | Pro | Leu | Thr |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ser | Pro | Phe | Ala | Leu | Leu | Asn | Ile | Cys | Cys | Phe |
|-----|-----|-----|-----|-----|-----|-----|-----|-----|-----|-----|
|     | 50  |     |     |     |     | 55  |     |     |     |     |

( 2 ) INFORMATION FOR SEQ ID NO:52:

( i ) SEQUENCE CHARACTERISTICS:
        ( A ) LENGTH: 510 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..507

( x i ) SEQUENCE DESCRIPTION: SEQ ID NO:52:

| ATG | GAT | ACC | TGG | ATA | TAT | CTT | TCT | CAG | GGC | TTT | GCG | GTG | GCG | ATG | ACG | 48 |
| Met | Asp | Thr | Trp | Ile | Tyr | Leu | Ser | Gln | Gly | Phe | Ala | Val | Ala | Met | Thr |    |
| 1   |     |     |     | 5   |     |     |     |     | 10  |     |     |     |     | 15  |     |    |

| CCG | GAA | AAC | CTG | GTT | ATC | GCG | TTG | ATT | GGC | TGC | TTC | GTG | GGC | ACG | ATC | 96 |
| Pro | Glu | Asn | Leu | Val | Ile | Ala | Leu | Ile | Gly | Cys | Phe | Val | Gly | Thr | Ile |    |
|     |     |     | 20  |     |     |     |     | 25  |     |     |     |     | 30  |     |     |    |

| GTC | GGT | CTG | CTG | CCG | GGT | CTG | GGA | CCG | ATC | AAC | GGC | GTG | GCA | ATC | TTA | 144 |
| Val | Gly | Leu | Leu | Pro | Gly | Leu | Gly | Pro | Ile | Asn | Gly | Val | Ala | Ile | Leu |     |
|     |     | 35  |     |     |     |     | 40  |     |     |     |     | 45  |     |     |     |     |

| CTG | CCG | CTG | GCC | TTT | GCG | TTG | CAT | CTG | CCT | GCG | GAG | TCG | GCG | CTA | ATT | 192 |
| Leu | Pro | Leu | Ala | Phe | Ala | Leu | His | Leu | Pro | Ala | Glu | Ser | Ala | Leu | Ile |     |
|     | 50  |     |     |     |     | 55  |     |     |     |     | 60  |     |     |     |     |     |

| CTG | CTG | GCG | ACG | GTG | TAC | ATT | GGC | TGT | GAG | TAT | GGC | GGC | AGG | ATC | TCC | 240 |
| Leu | Leu | Ala | Thr | Val | Tyr | Ile | Gly | Cys | Glu | Tyr | Gly | Gly | Arg | Ile | Ser |     |
| 65  |     |     |     |     | 70  |     |     |     |     | 75  |     |     |     |     | 80  |     |

| TCC | ATA | TTG | CTC | AAC | GTC | CCC | GGC | GAT | GCG | GCG | GCG | ATC | ATG | ACG | GCG | 288 |
| Ser | Ile | Leu | Leu | Asn | Val | Pro | Gly | Asp | Ala | Ala | Ala | Ile | Met | Thr | Ala |     |
|     |     |     |     | 85  |     |     |     |     | 90  |     |     |     |     | 95  |     |     |

| CTG | GAC | GGT | TAC | CCG | ATG | GCG | CAG | CAA | GGG | AAA | GGC | GGC | GTA | GCG | CTG | 336 |
| Leu | Asp | Gly | Tyr | Pro | Met | Ala | Gln | Gln | Gly | Lys | Gly | Gly | Val | Ala | Leu |     |
|     |     |     | 100 |     |     |     |     | 105 |     |     |     |     | 110 |     |     |     |

| TCG | ATT | TCC | GCA | GTC | AGC | TCA | TTT | TTC | GGT | TCA | TTA | ATC | GCT | ATC | GGC | 384 |
| Ser | Ile | Ser | Ala | Val | Ser | Ser | Phe | Phe | Gly | Ser | Leu | Ile | Ala | Ile | Gly |     |
|     |     | 115 |     |     |     |     | 120 |     |     |     |     | 125 |     |     |     |     |

| GGC | ATC | ATT | CTG | TTC | GCC | CCT | TTA | CTG | GCG | CAA | TGG | TCG | CTG | GCC | TTT | 432 |
| Gly | Ile | Ile | Leu | Phe | Ala | Pro | Leu | Leu | Ala | Gln | Trp | Ser | Leu | Ala | Phe |     |
|     | 130 |     |     |     |     | 135 |     |     |     |     | 140 |     |     |     |     |     |

| GGG | CCG | GCG | GAA | TAT | TTC | GCC | TTA | ATG | GTT | TTT | GCC | ATC | GCC | TGT | CTT | 480 |
| Gly | Pro | Ala | Glu | Tyr | Phe | Ala | Leu | Met | Val | Phe | Ala | Ile | Ala | Cys | Leu |     |
| 145 |     |     |     |     | 150 |     |     |     |     | 155 |     |     |     |     | 160 |     |

| GGC | AGC | ATG | ATG | GCG | CAA | AAC | CCG | GCT | TAA | 510 |
| Gly | Ser | Met | Met | Ala | Gln | Asn | Pro | Ala |     |     |
|     |     |     |     | 165 |     |     |     |     |     |     |

( 2 ) INFORMATION FOR SEQ ID NO:53:

( i ) SEQUENCE CHARACTERISTICS:

(A) LENGTH: 169 amino acids
(B) TYPE: amino acid
(D) TOPOLOGY: linear (ii) MOLECULE TYPE: protein (xi) SEQUENCE DESCRIPTION: SEQ ID NO:53:

| Met | Asp | Thr | Trp | Ile | Tyr | Leu | Ser | Gln | Gly | Phe | Ala | Val | Ala | Met | Thr |
|---|---|---|---|---|---|---|---|---|---|---|---|---|---|---|---|
| 1 | | | | 5 | | | | | 10 | | | | | 15 | |

| Pro | Glu | Asn | Leu | Val | Ile | Ala | Leu | Ile | Gly | Cys | Phe | Val | Gly | Thr | Ile |
|---|---|---|---|---|---|---|---|---|---|---|---|---|---|---|---|
| | | | 20 | | | | | 25 | | | | | 30 | | |

| Val | Gly | Leu | Leu | Pro | Gly | Leu | Gly | Pro | Ile | Asn | Gly | Val | Ala | Ile | Leu |
|---|---|---|---|---|---|---|---|---|---|---|---|---|---|---|---|
| | | 35 | | | | | 40 | | | | | 45 | | | |

| Leu | Pro | Leu | Ala | Phe | Ala | Leu | His | Leu | Pro | Ala | Glu | Ser | Ala | Leu | Ile |
|---|---|---|---|---|---|---|---|---|---|---|---|---|---|---|---|
| | 50 | | | | | 55 | | | | | 60 | | | | |

| Leu | Leu | Ala | Thr | Val | Tyr | Ile | Gly | Cys | Glu | Tyr | Gly | Gly | Arg | Ile | Ser |
|---|---|---|---|---|---|---|---|---|---|---|---|---|---|---|---|
| 65 | | | | | 70 | | | | | 75 | | | | | 80 |

| Ser | Ile | Leu | Leu | Asn | Val | Pro | Gly | Asp | Ala | Ala | Ala | Ile | Met | Thr | Ala |
|---|---|---|---|---|---|---|---|---|---|---|---|---|---|---|---|
| | | | | 85 | | | | | 90 | | | | | 95 | |

| Leu | Asp | Gly | Tyr | Pro | Met | Ala | Gln | Gln | Gly | Lys | Gly | Gly | Val | Ala | Leu |
|---|---|---|---|---|---|---|---|---|---|---|---|---|---|---|---|
| | | | | 100 | | | | | 105 | | | | | 110 | |

| Ser | Ile | Ser | Ala | Val | Ser | Ser | Phe | Phe | Gly | Ser | Leu | Ile | Ala | Ile | Gly |
|---|---|---|---|---|---|---|---|---|---|---|---|---|---|---|---|
| | | 115 | | | | | 120 | | | | | 125 | | | |

| Gly | Ile | Ile | Leu | Phe | Ala | Pro | Leu | Leu | Ala | Gln | Trp | Ser | Leu | Ala | Phe |
|---|---|---|---|---|---|---|---|---|---|---|---|---|---|---|---|
| | 130 | | | | | 135 | | | | | 140 | | | | |

| Gly | Pro | Ala | Glu | Tyr | Phe | Ala | Leu | Met | Val | Phe | Ala | Ile | Ala | Cys | Leu |
|---|---|---|---|---|---|---|---|---|---|---|---|---|---|---|---|
| 145 | | | | | 150 | | | | | 155 | | | | | 160 |

| Gly | Ser | Met | Met | Ala | Gln | Asn | Pro | Ala |
|---|---|---|---|---|---|---|---|---|
| | | | | 165 | | | | |

(2) INFORMATION FOR SEQ ID NO:54:

(i) SEQUENCE CHARACTERISTICS:
(A) LENGTH: 978 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..975

(xi) SEQUENCE DESCRIPTION: SEQ ID NO:54:

```
ATG AAA AAA CAA TTA CTT CGT ACC CTT ACT GCA AGC ATT TTA TTA ATG     48
Met Lys Lys Gln Leu Leu Arg Thr Leu Thr Ala Ser Ile Leu Leu Met
 1               5                  10                  15

AGT ACC TCT GTT CTG GCG CAG GAG GCG CCG TCG CGA ACG GAA TGT ATC     96
Ser Thr Ser Val Leu Ala Gln Glu Ala Pro Ser Arg Thr Glu Cys Ile
                20                  25                  30

GCG CCA GCC AAA CCT GGC GGC GGT TTC GAC CTC ACC TGT AAG CTG ATT    144
Ala Pro Ala Lys Pro Gly Gly Gly Phe Asp Leu Thr Cys Lys Leu Ile
                35                  40                  45

CAG GTG AGT TTG CTG GAG ACT GGC GCT ATC GAG AAA CCC ATG CGG GTA    192
Gln Val Ser Leu Leu Glu Thr Gly Ala Ile Glu Lys Pro Met Arg Val
        50                  55                  60

ACG TAT ATG CCC GGC GGC GTC GGC GCT GTG GCC TAT AAC GCG ATA GTC    240
Thr Tyr Met Pro Gly Gly Val Gly Ala Val Ala Tyr Asn Ala Ile Val
 65                  70                  75                  80

GCC CAA CGC CCT GGC GAA CCC GGG ACT GTG GTC GCC TTT TCC GGC GGT    288
Ala Gln Arg Pro Gly Glu Pro Gly Thr Val Val Ala Phe Ser Gly Gly
```

|   |   |   |   |   |   |   |   |   |   |   |   |   |   |   |   |   |
|---|---|---|---|---|---|---|---|---|---|---|---|---|---|---|---|---|
| | | | | 85 | | | | | 90 | | | | | 95 | | |
| TCG | CTG | CTC | AAC | CTG | TCG | CAG | GGG | AAA | TTT | GGT | CGC | TAC | GGC | GTG | GAT | 336 |
| Ser | Leu | Leu | Asn<br>100 | Leu | Ser | Gln | Gly | Lys<br>105 | Phe | Gly | Arg | Tyr | Gly<br>110 | Val | Asp | |
| GAT | GTG | CGC | TGG | CTG | GCA | AGC | GTG | GGC | ACT | GAT | TAC | GGC | ATG | ATC | GCC | 384 |
| Asp | Val | Arg<br>115 | Trp | Leu | Ala | Ser | Val<br>120 | Gly | Thr | Asp | Tyr | Gly<br>125 | Met | Ile | Ala | |
| GTG | CGT | GCG | GAT | TCT | CCG | TGG | AAA | ACG | CTG | AAA | GAT | CTG | ATG | ACG | GCG | 432 |
| Val | Arg<br>130 | Ala | Asp | Ser | Pro | Trp<br>135 | Lys | Thr | Leu | Lys | Asp<br>140 | Leu | Met | Thr | Ala | |
| ATG | GAA | AAA | GAT | CCC | AAC | AGC | GTG | GTC | ATT | GGC | GCT | GGC | GCC | TCT | ATT | 480 |
| Met<br>145 | Glu | Lys | Asp | Pro | Asn<br>150 | Ser | Val | Val | Ile | Gly<br>155 | Ala | Gly | Ala | Ser | Ile<br>160 | |
| GGC | AGC | CAG | GAC | TGG | ATG | AAG | TCG | GCA | TTG | CTG | GCG | CAA | AAG | GCG | AAC | 528 |
| Gly | Ser | Gln | Asp | Trp<br>165 | Met | Lys | Ser | Ala | Leu<br>170 | Leu | Ala | Gln | Lys | Ala<br>175 | Asn | |
| GTC | GAC | CCG | CAC | AAG | ATG | CGC | TAC | GTT | GCC | TTT | GAG | GGC | GGC | GGC | GAG | 576 |
| Val | Asp | Pro | His<br>180 | Lys | Met | Arg | Tyr | Val<br>185 | Ala | Phe | Glu | Gly | Gly<br>190 | Gly | Glu | |
| CCG | GTG | ACG | GCA | TTA | ATG | GGC | AAC | CAT | GTT | CAG | GTT | GTC | TCC | GGC | GAT | 624 |
| Pro | Val | Thr<br>195 | Ala | Leu | Met | Gly | Asn<br>200 | His | Val | Gln | Val | Val<br>205 | Ser | Gly | Asp | |
| CTC | AGT | GAA | ATG | GTG | CCT | TAT | CTG | GGC | GGC | GAC | AAA | ATC | CGC | GTG | CTT | 672 |
| Leu | Ser<br>210 | Glu | Met | Val | Pro | Tyr<br>215 | Leu | Gly | Gly | Asp | Lys<br>220 | Ile | Arg | Val | Leu | |
| GCC | GTC | TTT | TCA | GAA | AAT | CGT | CTG | CCG | GGC | CAG | CTT | GCC | AAT | ATC | CCT | 720 |
| Ala<br>225 | Val | Phe | Ser | Glu | Asn<br>230 | Arg | Leu | Pro | Gly | Gln<br>235 | Leu | Ala | Asn | Ile | Pro<br>240 | |
| ACC | GCT | AAA | GAA | CAG | GGG | TAC | GAC | CTG | GTG | TGG | CCG | ATT | ATT | CGC | GGC | 768 |
| Thr | Ala | Lys | Glu | Gln<br>245 | Gly | Tyr | Asp | Leu | Val<br>250 | Trp | Pro | Ile | Ile | Arg<br>255 | Gly | |
| TTC | TAC | GTC | GGG | CCC | AAA | GTC | AGC | GAT | GCC | GAT | TAC | CAG | TGG | TGG | GTG | 816 |
| Phe | Tyr | Val | Gly<br>260 | Pro | Lys | Val | Ser | Asp<br>265 | Ala | Asp | Tyr | Gln | Trp<br>270 | Trp | Val | |
| GAT | ACC | TTC | AAG | AAG | CTC | CAG | CAA | ACC | GAC | GAG | TTT | AAA | AAG | CAG | CGC | 864 |
| Asp | Thr | Phe<br>275 | Lys | Lys | Leu | Gln | Gln<br>280 | Thr | Asp | Glu | Phe | Lys<br>285 | Lys | Gln | Arg | |
| GAT | CTG | CGC | GGC | CTG | TTT | GAG | TTC | GAC | ATG | ACC | GGC | CAG | CAG | CTC | GAT | 912 |
| Asp | Leu | Arg<br>290 | Gly | Leu | Phe | Glu<br>295 | Phe | Asp | Met | Thr | Gly<br>300 | Gln | Gln | Leu | Asp | |
| GAC | TAC | GTG | AAA | AAA | CAG | GTT | ACT | GAT | TAC | CGT | GAA | CAG | GCG | AAA | GCC | 960 |
| Asp<br>305 | Tyr | Val | Lys | Lys<br>310 | Gln | Val | Thr | Asp | Tyr<br>315 | Arg | Glu | Gln | Ala | Lys<br>320 | Ala | |
| TTC | GGA | CTC | GCG | AAA | TAA | | | | | | | | | | | 978 |
| Phe | Gly | Leu | Ala | Lys<br>325 | | | | | | | | | | | | |

( 2 ) INFORMATION FOR SEQ ID NO:55:

( i ) SEQUENCE CHARACTERISTICS:
        ( A ) LENGTH: 325 amino acids
        ( B ) TYPE: amino acid
        ( D ) TOPOLOGY: linear ( i i ) MOLECULE TYPE: protein ( x i ) SEQUENCE DESCRIPTION: SEQ ID NO:55:

|   |   |   |   |   |   |   |   |   |   |   |   |   |   |   |
|---|---|---|---|---|---|---|---|---|---|---|---|---|---|---|
| Met<br>1 | Lys | Lys | Gln | Leu<br>5 | Leu | Arg | Thr | Leu | Thr<br>10 | Ala | Ser | Ile | Leu | Leu Met<br>15 |
| Ser | Thr | Ser | Val<br>20 | Leu | Ala | Gln | Glu | Ala<br>25 | Pro | Ser | Arg | Thr | Glu<br>30 | Cys Ile |

```
Ala  Pro  Ala  Lys  Pro  Gly  Gly  Gly  Phe  Asp  Leu  Thr  Cys  Lys  Leu  Ile
          35                  40                      45

Gln  Val  Ser  Leu  Leu  Glu  Thr  Gly  Ala  Ile  Glu  Lys  Pro  Met  Arg  Val
     50                       55                      60

Thr  Tyr  Met  Pro  Gly  Gly  Val  Gly  Ala  Val  Ala  Tyr  Asn  Ala  Ile  Val
65                       70                      75                            80

Ala  Gln  Arg  Pro  Gly  Glu  Pro  Gly  Thr  Val  Val  Ala  Phe  Ser  Gly  Gly
                    85                       90                      95

Ser  Leu  Leu  Asn  Leu  Ser  Gln  Gly  Lys  Phe  Gly  Arg  Tyr  Gly  Val  Asp
               100                      105                     110

Asp  Val  Arg  Trp  Leu  Ala  Ser  Val  Gly  Thr  Asp  Tyr  Gly  Met  Ile  Ala
          115                      120                     125

Val  Arg  Ala  Asp  Ser  Pro  Trp  Lys  Thr  Leu  Lys  Asp  Leu  Met  Thr  Ala
     130                      135                     140

Met  Glu  Lys  Asp  Pro  Asn  Ser  Val  Val  Ile  Gly  Ala  Gly  Ala  Ser  Ile
145                           150                     155                      160

Gly  Ser  Gln  Asp  Trp  Met  Lys  Ser  Ala  Leu  Leu  Ala  Gln  Lys  Ala  Asn
                    165                      170                     175

Val  Asp  Pro  His  Lys  Met  Arg  Tyr  Val  Ala  Phe  Glu  Gly  Gly  Gly  Glu
               180                      185                     190

Pro  Val  Thr  Ala  Leu  Met  Gly  Asn  His  Val  Gln  Val  Val  Ser  Gly  Asp
          195                      200                     205

Leu  Ser  Glu  Met  Val  Pro  Tyr  Leu  Gly  Gly  Asp  Lys  Ile  Arg  Val  Leu
     210                      215                     220

Ala  Val  Phe  Ser  Glu  Asn  Arg  Leu  Pro  Gly  Gln  Leu  Ala  Asn  Ile  Pro
225                           230                     235                      240

Thr  Ala  Lys  Glu  Gln  Gly  Tyr  Asp  Leu  Val  Trp  Pro  Ile  Ile  Arg  Gly
                    245                      250                     255

Phe  Tyr  Val  Gly  Pro  Lys  Val  Ser  Asp  Ala  Asp  Tyr  Gln  Trp  Trp  Val
               260                      265                     270

Asp  Thr  Phe  Lys  Lys  Leu  Gln  Gln  Thr  Asp  Glu  Phe  Lys  Lys  Gln  Arg
          275                      280                     285

Asp  Leu  Arg  Gly  Leu  Phe  Glu  Phe  Asp  Met  Thr  Gly  Gln  Gln  Leu  Asp
     290                      295                     300

Asp  Tyr  Val  Lys  Lys  Gln  Val  Thr  Asp  Tyr  Arg  Glu  Gln  Ala  Lys  Ala
                    310                      315                     320

Phe  Gly  Leu  Ala  Lys
                    325
```

( 2 ) INFORMATION FOR SEQ ID NO:56:

( i ) SEQUENCE CHARACTERISTICS:
        ( A ) LENGTH: 361 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..357

( x i ) SEQUENCE DESCRIPTION: SEQ ID NO:56:

```
GTC  GTA  CCA  CAG  TGG  GGC  GGC  GGC  GGT  AAT  CAT  AAC  GGC  GGC  GGC  AAT     48
Val  Val  Pro  Gln  Trp  Gly  Gly  Gly  Gly  Asn  His  Asn  Gly  Gly  Gly  Asn
1                        5                       10                      15

AGT  TCC  GGC  CCG  GAC  TCA  ACG  TTG  AGC  ATT  TAT  CAG  TAC  GGT  TCC  GCT     96
Ser  Ser  Gly  Pro  Asp  Ser  Thr  Leu  Ser  Ile  Tyr  Gln  Tyr  Gly  Ser  Ala
```

```
              20                          25                         30
AAC  GCT  GCG  CTT  GCT  CTG  CAA  AGC  GAT  GCC  CGT  AAA  TCT  GAA  ACG  ACC     144
Asn  Ala  Ala  Leu  Ala  Leu  Gln  Ser  Asp  Ala  Arg  Lys  Ser  Glu  Thr  Thr
          35                       40                       45

ATT  ACC  CAG  AGC  GGT  TAT  GGT  AAC  GGC  GCC  GAT  GTA  GGC  CAG  GGT  GCG     192
Ile  Thr  Gln  Ser  Gly  Tyr  Gly  Asn  Gly  Ala  Asp  Val  Gly  Gln  Gly  Ala
     50                       55                       60

GAT  AAT  AGT  ACT  ATT  GAA  CTG  ACT  CAG  AAT  GGT  TTC  AGA  AAT  AAT  GCC     240
Asp  Asn  Ser  Thr  Ile  Glu  Leu  Thr  Gln  Asn  Gly  Phe  Arg  Asn  Asn  Ala
65                       70                       75                       80

ACC  ATC  GAC  CAG  TGG  AAC  GCT  AAA  AAC  TCC  GAT  ATT  ACT  GTC  GGC  CAA     288
Thr  Ile  Asp  Gln  Trp  Asn  Ala  Lys  Asn  Ser  Asp  Ile  Thr  Val  Gly  Gln
               85                       90                       95

TAC  GGC  GGT  AAT  AAC  GCC  GCG  CTG  GTT  AAT  CAG  ACC  GCA  TCT  GAT  TCT     336
Tyr  Gly  Gly  Asn  Asn  Ala  Ala  Leu  Val  Asn  Gln  Thr  Ala  Ser  Asp  Ser
               100                      105                      110

GAC  TCT  TAT  ACA  CAA  GTA  GCG  TCCT                                            361
Asp  Ser  Tyr  Thr  Gln  Val  Ala
               115
```

( 2 ) INFORMATION FOR SEQ ID NO:57:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:57:

```
Val  Val  Pro  Gln  Trp  Gly  Gly  Gly  Gly  Asn  His  Asn  Gly  Gly  Gly  Asn
1                        5                        10                       15

Ser  Ser  Gly  Pro  Asp  Ser  Thr  Leu  Ser  Ile  Tyr  Gln  Tyr  Gly  Ser  Ala
               20                       25                       30

Asn  Ala  Ala  Leu  Ala  Leu  Gln  Ser  Asp  Ala  Arg  Lys  Ser  Glu  Thr  Thr
               35                       40                       45

Ile  Thr  Gln  Ser  Gly  Tyr  Gly  Asn  Gly  Ala  Asp  Val  Gly  Gln  Gly  Ala
     50                       55                       60

Asp  Asn  Ser  Thr  Ile  Glu  Leu  Thr  Gln  Asn  Gly  Phe  Arg  Asn  Asn  Ala
65                       70                       75                       80

Thr  Ile  Asp  Gln  Trp  Asn  Ala  Lys  Asn  Ser  Asp  Ile  Thr  Val  Gly  Gln
               85                       90                       95

Tyr  Gly  Gly  Asn  Asn  Ala  Ala  Leu  Val  Asn  Gln  Thr  Ala  Ser  Asp  Ser
               100                      105                      110

Asp  Ser  Tyr  Thr  Gln  Val  Ala  Ser
               115                      120
```

( 2 ) INFORMATION FOR SEQ ID NO:58:

( i ) SEQUENCE CHARACTERISTICS:
        ( A ) LENGTH: 456 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..456

( x i ) SEQUENCE DESCRIPTION: SEQ ID NO:58:

```
ATG  AAA  CTT  TTA  AAA  GTG  GCA  GCA  TTC  GCA  GCA  ATC  GTA  GTT  TCT  GGC     48
Met  Lys  Leu  Leu  Lys  Val  Ala  Ala  Phe  Ala  Ala  Ile  Val  Val  Ser  Gly
1                        5                        10                       15
```

| | | | | | | | | | | | | | | | | |
|---|---|---|---|---|---|---|---|---|---|---|---|---|---|---|---|---|
| AGT | GCT | CTG | GCT | GGC | GTC | GTT | CCA | CAA | TGG | GGC | GGC | GGC | GGT | AAT | CAT | 96 |
| Ser | Ala | Leu | Ala<br>20 | Gly | Val | Val | Pro | Gln<br>25 | Trp | Gly | Gly | Gly | Gly<br>30 | Asn | His | |
| AAC | GGC | GGC | GGC | AAT | AGT | TCC | GGC | CCG | GAC | TCA | ACG | TTG | AGC | ATT | TAT | 144 |
| Asn | Gly | Gly<br>35 | Gly | Asn | Ser | Ser | Gly | Pro<br>40 | Asp | Ser | Thr | Leu<br>45 | Ser | Ile | Tyr | |
| CAG | TAC | GGT | TCC | GCT | AAC | GCT | GCG | CTT | GCT | CTG | CAA | AGC | GAT | GCC | CGT | 192 |
| Gln | Tyr<br>50 | Gly | Ser | Ala | Asn | Ala<br>55 | Ala | Leu | Ala | Leu | Gln<br>60 | Ser | Asp | Ala | Arg | |
| AAA | TCT | GAA | ACG | ACC | ATT | ACC | CAG | AGC | GGT | TAT | GGT | AAC | GGC | GCC | GAT | 240 |
| Lys<br>65 | Ser | Glu | Thr | Thr | Ile<br>70 | Thr | Gln | Ser | Gly | Tyr<br>75 | Gly | Asn | Gly | Ala | Asp<br>80 | |
| GTA | GGC | CAG | GGT | GCG | GAT | AAT | AGT | ACT | ATT | GAA | CTG | ACT | CAG | AAT | GGT | 288 |
| Val | Gly | Gln | Gly | Ala<br>85 | Asp | Asn | Ser | Thr | Ile<br>90 | Glu | Leu | Thr | Gln | Asn<br>95 | Gly | |
| TTC | AGA | AAT | AAT | GCC | ACC | ATC | GAC | CAG | TGG | AAC | GCT | AAA | AAC | TCC | GAT | 336 |
| Phe | Arg | Asn | Asn<br>100 | Ala | Thr | Ile | Asp | Gln<br>105 | Trp | Asn | Ala | Lys | Asn<br>110 | Ser | Asp | |
| ATT | ACT | GTC | GGC | CAA | TAC | GGC | GGT | AAT | AAC | GCC | GCG | CTG | GTT | AAT | CAG | 384 |
| Ile | Thr | Val<br>115 | Gly | Gln | Tyr | Gly | Gly<br>120 | Asn | Asn | Ala | Ala | Leu<br>125 | Val | Asn | Gln | |
| ACC | GCA | TCT | GAT | TCC | AGC | GTA | ATG | GTG | CGT | CAG | GTT | GGT | TTT | GGC | AAC | 432 |
| Thr | Ala<br>130 | Ser | Asp | Ser | Ser | Val<br>135 | Met | Val | Arg | Gln | Val<br>140 | Gly | Phe | Gly | Asn | |
| AAC | GCC | ACG | GCT | AAC | CAG | TAT | TAA | | | | | | | | | 456 |
| Asn<br>145 | Ala | Thr | Ala | Asn | Gln<br>150 | Tyr | | | | | | | | | | |

( 2 ) INFORMATION FOR SEQ ID NO:59:

( i ) SEQUENCE CHARACTERISTICS:
        ( A ) LENGTH: 151 amino acids
        ( B ) TYPE: amino acid
        ( D ) TOPOLOGY: linear ( i i ) MOLECULE TYPE: protein ( x i ) SEQUENCE DESCRIPTION: SEQ ID NO:59:

| | | | | | | | | | | | | | | | |
|---|---|---|---|---|---|---|---|---|---|---|---|---|---|---|---|
| Met<br>1 | Lys | Leu | Leu | Lys<br>5 | Val | Ala | Ala | Phe | Ala<br>10 | Ala | Ile | Val | Val | Ser<br>15 | Gly |
| Ser | Ala | Leu | Ala<br>20 | Gly | Val | Val | Pro | Gln<br>25 | Trp | Gly | Gly | Gly | Gly<br>30 | Asn | His |
| Asn | Gly | Gly<br>35 | Gly | Asn | Ser | Ser | Gly<br>40 | Pro | Asp | Ser | Thr | Leu<br>45 | Ser | Ile | Tyr |
| Gln | Tyr<br>50 | Gly | Ser | Ala | Asn | Ala<br>55 | Ala | Leu | Ala | Leu | Gln<br>60 | Ser | Asp | Ala | Arg |
| Lys<br>65 | Ser | Glu | Thr | Thr | Ile<br>70 | Thr | Gln | Ser | Gly | Tyr<br>75 | Gly | Asn | Gly | Ala | Asp<br>80 |
| Val | Gly | Gln | Gly | Ala<br>85 | Asp | Asn | Ser | Thr | Ile<br>90 | Glu | Leu | Thr | Gln | Asn<br>95 | Gly |
| Phe | Arg | Asn | Asn<br>100 | Ala | Thr | Ile | Asp | Gln<br>105 | Trp | Asn | Ala | Lys | Asn<br>110 | Ser | Asp |
| Ile | Thr | Val<br>115 | Gly | Gln | Tyr | Gly | Gly<br>120 | Asn | Asn | Pro | Ala | Leu<br>125 | Val | Asn | Gln |
| Thr | Ala<br>130 | Ser | Asp | Ser | Ser | Val<br>135 | Met | Val | Arg | Gln | Val<br>140 | Gly | Phe | Gly | Asn |
| Asn<br>145 | Ala | Thr | Ala | Asn | Gln<br>150 | Tyr | | | | | | | | | |

( 2 ) INFORMATION FOR SEQ ID NO:60:

( i ) SEQUENCE CHARACTERISTICS:
        ( A ) LENGTH: 558 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..555

( x i ) SEQUENCE DESCRIPTION: SEQ ID NO:60:

```
ATG AAA CAT AAA TTA ATG ACC TCT ACT ATT GCG AGT CTG ATG TTT GTC      48
Met Lys His Lys Leu Met Thr Ser Thr Ile Ala Ser Leu Met Phe Val
 1               5                  10                  15

GCT GGC GCA GCG GTT GCG GCT GAT CCT ACT CCG GTG AGC GTG AGT GGC      96
Ala Gly Ala Ala Val Ala Ala Asp Pro Thr Pro Val Ser Val Ser Gly
              20                  25                  30

GGT ACT ATT CAT TTC GAA GGT AAA CTG GTT AAT GCA GCC TGT GCC GTT     144
Gly Thr Ile His Phe Glu Gly Lys Leu Val Asn Ala Ala Cys Ala Val
         35                  40                  45

AGC ACT AAA TCC GCC GAT CAA ACG GTG ACG CTG GGT CAA TAC CGT ACC     192
Ser Thr Lys Ser Ala Asp Gln Thr Val Thr Leu Gly Gln Tyr Arg Thr
     50                  55                  60

GCC AGC TTT ACG GCG ATT GGT AAT ACG ACT GCG CAG GTG CCT TTC TCC     240
Ala Ser Phe Thr Ala Ile Gly Asn Thr Thr Ala Gln Val Pro Phe Ser
 65                  70                  75                  80

ATC GTC CTG AAT GAC TGC GAT CCG AAA GTG GCG GCC ACC GCT GCC GTG     288
Ile Val Leu Asn Asp Cys Asp Pro Lys Val Ala Ala Thr Ala Ala Val
                 85                  90                  95

GCT TTC TCT GGT CAG GCA GAT AAC ACC AAC CCT AAT TTG CTG GCT GTC     336
Ala Phe Ser Gly Gln Ala Asp Asn Thr Asn Pro Asn Leu Leu Ala Val
            100                 105                 110

TCC TCT GCG GAC AAT AGC ACC ACC GCA ACC GGC GTC GGG ATT GAG ATT     384
Ser Ser Ala Asp Asn Ser Thr Thr Ala Thr Gly Val Gly Ile Glu Ile
        115                 120                 125

CTT GAT AAT ACC TCT TCA CCG TTG AAG CCG GAC GGC GCG ACC TTC TCG     432
Leu Asp Asn Thr Ser Ser Pro Leu Lys Pro Asp Gly Ala Thr Phe Ser
    130                 135                 140

GCG AAG CAG GCG CTG GTT GAA GGC ACC AAT ACG CTG CGT TTT ACC GCA     480
Ala Lys Gln Ala Leu Val Glu Gly Thr Asn Thr Leu Arg Phe Thr Ala
145                 150                 155                 160

CGC TAT AAG GCA ACC GCC ACC GCC ACG ACG CCA GGC CAG GCT AAT GCC     528
Arg Tyr Lys Ala Thr Ala Thr Ala Thr Thr Pro Gly Gln Ala Asn Ala
                165                 170                 175

GAC GCC ACC TTT ATC ATG AAA TAC GAA TAA                             558
Asp Ala Thr Phe Ile Met Lys Tyr Glu
                180                 185
```

( 2 ) INFORMATION FOR SEQ ID NO:61:

( i ) SEQUENCE CHARACTERISTICS:
        ( A ) LENGTH: 185 amino acids
        ( B ) TYPE: amino acid
        ( D ) TOPOLOGY: linear ( i i ) MOLECULE TYPE: protein ( x i ) SEQUENCE DESCRIPTION: SEQ ID NO:61:

```
Met Lys His Lys Leu Met Thr Ser Thr Ile Ala Ser Leu Met Phe Val
 1               5                  10                  15

Ala Gly Ala Ala Val Ala Ala Asp Pro Thr Pro Val Ser Val Ser Gly
              20                  25                  30
```

-continued

| | | | | | | | | | | | | | | |
|---|---|---|---|---|---|---|---|---|---|---|---|---|---|---|
| Gly | Thr | Ile 35 | His | Phe | Glu | Gly | Lys 40 | Leu | Val | Asn | Ala | Ala 45 | Cys | Ala | Val |
| Ser | Thr 50 | Lys | Ser | Ala | Asp | Gln 55 | Thr | Val | Thr | Leu | Gly 60 | Gln | Tyr | Arg | Thr |
| Ala 65 | Ser | Phe | Thr | Ala | Ile 70 | Gly | Asn | Thr | Thr | Ala 75 | Gln | Val | Pro | Phe | Ser 80 |
| Ile | Val | Leu | Asn | Asp 85 | Cys | Asp | Pro | Lys | Val 90 | Ala | Ala | Thr | Ala | Ala 95 | Val |
| Ala | Phe | Ser | Gly 100 | Gln | Ala | Asp | Asn | Thr 105 | Asn | Pro | Asn | Leu | Leu 110 | Ala | Val |
| Ser | Ser | Ala 115 | Asp | Asn | Ser | Thr | Thr 120 | Ala | Thr | Gly | Val | Gly 125 | Ile | Glu | Ile |
| Leu | Asp 130 | Asn | Thr | Ser | Ser | Pro 135 | Leu | Lys | Pro | Asp | Gly 140 | Ala | Thr | Phe | Ser |
| Ala 145 | Lys | Gln | Ala | Leu | Val 150 | Glu | Gly | Thr | Asn | Thr 155 | Leu | Arg | Phe | Thr | Ala 160 |
| Arg | Tyr | Lys | Ala | Thr 165 | Ala | Thr | Ala | Thr | Thr 170 | Pro | Gly | Gln | Ala | Asn 175 | Ala |
| Asp | Ala | Thr | Phe 180 | Ile | Met | Lys | Tyr | Glu 185 | | | | | | | |